US011709165B2

(12) United States Patent
Oka et al.

(10) Patent No.: US 11,709,165 B2
(45) Date of Patent: Jul. 25, 2023

(54) EXAMINATION METHOD FOR PREDICTION OF EFFECT OF TREATMENT OF CANCER BASED ON DETECTION OF CANCER/TESTIS ANTIBODIES

(71) Applicant: KAWASAKI GAKUEN EDUCATIONAL FOUNDATION, Kurashiki (JP)

(72) Inventors: Mikio Oka, Kurashiki (JP); Eiichi Nakayama, Kurashiki (JP); Yoshihiro Ohue, New York, NY (US); Koji Kurose, Kurashiki (JP)

(73) Assignee: KAWASAKI GAKUEN EDUCATIONAL FOUNDATION, Kurashiki (JP)

( * ) Notice: Subject to any disclaimer, the term of this patent is extended or adjusted under 35 U.S.C. 154(b) by 224 days.

(21) Appl. No.: 16/611,947

(22) PCT Filed: May 10, 2018

(86) PCT No.: PCT/JP2018/018083
§ 371 (c)(1),
(2) Date: Nov. 8, 2019

(87) PCT Pub. No.: WO2018/207866
PCT Pub. Date: Nov. 15, 2018

(65) Prior Publication Data
US 2021/0148927 A1    May 20, 2021

(30) Foreign Application Priority Data

May 11, 2017    (JP) .............................. JP2017-094986

(51) Int. Cl.
| | |
|---|---|
| G01N 33/68 | (2006.01) |
| A61K 39/00 | (2006.01) |
| C07K 14/82 | (2006.01) |
| C12N 5/0783 | (2010.01) |
| G01N 33/574 | (2006.01) |
| A61K 38/00 | (2006.01) |
| A61P 35/00 | (2006.01) |

(52) U.S. Cl.
CPC ............ *G01N 33/6854* (2013.01); *A61K 39/001184* (2018.08); *A61P 35/00* (2018.01); *C07K 14/82* (2013.01); *C12N 5/0636* (2013.01); *G01N 33/57407* (2013.01); *A61K 38/00* (2013.01); *A61K 2039/892* (2018.08); *C12N 2501/505* (2013.01); *G01N 2800/344* (2013.01); *G01N 2800/52* (2013.01)

(58) Field of Classification Search
CPC ................................................. G01N 33/6854
See application file for complete search history.

(56) References Cited

U.S. PATENT DOCUMENTS

| | | | | |
|---|---|---|---|---|
| 2008/0139464 A1* | 6/2008 | Gnjatic | .............. | C07K 14/4748 514/19.3 |
| 2015/0118244 A1* | 4/2015 | Shahabi | ............. | C07K 16/2818 424/142.1 |

FOREIGN PATENT DOCUMENTS

| | | |
|---|---|---|
| JP | 5709108 | 4/2015 |
| WO | 2013/147233 | 10/2013 |
| WO | 2014/077725 A1 | 5/2014 |
| WO | 2015/172843 A1 | 11/2015 |
| WO | 2016/181912 | 11/2016 |

OTHER PUBLICATIONS

Allison JP. Checkpoint Blockade in Tumor Immunotherapy: New Insights and Opportunities. J. Immunother. 32, 986, 2009. (Year: 2009).*
Yuan et al., Integrated NY-ESO-1 antibody and CD8+ T-cell responses correlate with clinical benefit in advanced melanoma patients treated with ipilimumab. PNAS, 108, 16723-16728, 2011. (Year: 2011).*
Extended European Search Report for corresponding European Application No. 18797663.4 dated Mar. 9, 2021, 11 pgs.
Chapman, C. J., et al: "Autoantibodies in lung cancer: possibilities for early detection and subsequent cure", Thorax, BMJ Publishing Group, GB, vol. 63, No. 3, Mar. 1, 2008 (Mar. 1, 2008), pp. 228-233, XP008130047, ISSN: 0040-6376, DOI: 10.1136/THX. 2007.083592.
Ohue et al., "Antibody response to cancer/testis (CT) antigens: A prognostic marker in cancer patients", Oncoimmunology, vol. 3, No. 11, Nov. 2, 2014 (Nov. 2, 2014), p. e970032, XP055747495 DOI: 10.4161/21624011.2014.970032.
International Search Report for PCT/JP2018/018083, dated Aug. 7, 2018, 10 pages.
Shimada, "Development and Clinical Significance of Serum p53 Antibodies", Modern media, Gastroenterological Surgery, Chiba Cancer Center, 2008, vol. 54, No. 8, pp. 233-237.
Ohue et al., "Prolongation of Overall Survival in Advanced Lung Adenocarcinoma Patients with the XAGE1 (GAGED2a) Antibody", Clinical Cancer Research, Oct. 1, 2014, vol. 20, (19), pp. 5052-5063.

(Continued)

*Primary Examiner* — Elly-Gerald Stoica
(74) *Attorney, Agent, or Firm* — FisherBroyles, LLP; Joseph Hyosuk Kim

(57) ABSTRACT

[Object] To provide a novel examination method for a cancer treatment effect, screening method for a peptide for a cancer vaccine, and peptide and composition for inducing an immune response against cancer. [Solving Means] Provided are an examination method for a cancer treatment effect and a screening method for a peptide for a cancer vaccine each including detecting an antibody against a cancer/testis antigen or an anti-p53 antibody in a sample. It is suitable that an anti-XAGE1 antibody (IgG and/or IgA) be detected, or an anti-NY-ESO-1 antibody (IgG) be detected. Also provided are a novel peptide and novel composition for inducing immune responses against cancer.

17 Claims, 34 Drawing Sheets

Specification includes a Sequence Listing.

(56) References Cited

OTHER PUBLICATIONS

Beeton-Kempen et al., "Development of a novel, quantitative protein microarray platform for the multiplexed serological analysis of autoantibodies to cancer-testis antigens", International Journal of Cancer, 2014, vol. 135, pp. 1842-1851.

* cited by examiner

| Antigen spreading | Responder | non-responder | p-value |
|---|---|---|---|
| MAGE-B3 | 6/8 | 0/6 | 0.01 |
| SSX4 | 5/8 | 0/6 | 0.03 |

EXAMINATION METHOD FOR PREDICTION OF EFFECT OF TREATMENT OF CANCER BASED ON DETECTION OF CANCER/TESTIS ANTIBODIES

This application is the U.S. national phase of International Application No. PCT/JP2018/018083 filed 10 May 2018, which designated the U.S. and claims priority to JP Patent Application No. 2017-094986 filed 11 May 2017, the entire contents of each of which are hereby incorporated by reference.

TECHNICAL FIELD

The present invention relates to examination for prediction of an effect of cancer treatment or prognosis prediction, and to utilization of an immune response-inducing peptide.

BACKGROUND ART

In Japan, 110,000 people are affected with lung cancer, which ranks first in number of deaths among major cancer sites in 2013. Its histologic types are broadly classified into small-cell lung cancer (10%) and non-small-cell lung cancer (NSCLC) (90%), and lung adenocarcinomas account for from 70% to 80% of the non-small-cell lung cancers. As treatment of lung cancer, surgical therapy, radiotherapy, and chemotherapy are well known. As chemotherapy, combination chemotherapy mainly using tyrosine kinase inhibitors or platinum agents has been performed. Median survival times (MSTs) for the small-cell and the non-small-cell lung cancer are approximately 12 and 30 months, respectively.

In recent years, in first-line and second-line treatment of advanced NSCLC, therapy with an anti-PD-1 antibody (nivolumab or pembrolizumab) of immune checkpoint inhibitors has been found to provide a significantly high response rate or a prolonged overall survival as compared to standard treatment. At present, anti-PD-1 antibody therapy is generally performed in Japan, the United States, and the European Union.

A useful biomarker for responded patients to immune checkpoint inhibitors is a PD-L1 molecule expressed in tumors and immunocompetent cells in tumors. However, a response rate of even a PD-L1 high expression group is from approximately 30% to 40%. Furthermore, immune checkpoint inhibitors are extremely expensive. Accordingly, a novel biomarker predicting responses is desired.

Furthermore, it is desired that novel treatment methods having a more potent antitumor effect other than immune checkpoint inhibitors are developed.

Hitherto, we have identified XAGE1 cancer/testis antigen expressed in lung adenocarcinoma, which is the most common lung cancer. We have revealed that: the XAGE1 antigen is expressed in 40% to 50% of advanced lung adenocarcinomas; an antibody (IgG) against XAGE1 is observed in about a half of patients expressing XAGE1 antigen; and patients positive for antibody (IgG) against XAGE1 have a prolonged prognosis (Non-Patent Literatures 1 and 2).

XAGE1 antigen is one of cancer/testis antigens (CT antigen), which are expressed in many cancers but only in testes among normal tissues (Non-Patent Literatures 3 and 4).

Response rates in CheckMate-017 trial, which was a phase III clinical trial comparing nivolumab and docetaxel for previously treated squamous-cell lung cancer, were 36% and 31% in a nivolumab group and a docetaxel group, respectively. Median survival times (referred to as MSTs) of primary outcome were 9.2 and 6.0 months in nivolumab and docetaxel group, respectively, showing significant prolongation. In addition, response rates in the similar CheckMate-057 trial comparing nivolumab and docetaxel for previously treated non-squamous non-small-cell lung cancer were 19% and 12% in nivolumab and a docetaxel group, respectively. MST of primary outcome was 12.2 and 9.4 months in nivolumab and docetaxel group, respectively, showing significant prolongation. Thus, a single agent of nivolumab was more effective as compared to docetaxel in unresectable or metastatic non-small-cell lung cancer treated previously.

In disease progression rate, although nivolumab was not significant as compared to the docetaxel in CheckMate-017 or CheckMate-057 trial, the rates in CheckMate-017 trial were 33% and 30% in nivolumab and docetaxel group, respectively, and the rates in CheckMate-057 trial were 44% and 29% in nivolumab and the docetaxel group, respectively.

In addition, as a biomarker research, a relationship between tumor PD-L1 expression and MST was investigated, resulted that a low or negative tumor PD-L1 expression showed poor MST.

Usefulness of pembrolizumab of another anti-PD-1 antibody was investigated in KEYNOTE-001 and KEYNOTE-010 trials for previously treated non-small-cell lung cancer. In KEYNOTE-001 trial, an overall response rate was from 18% to 20%, and the response rate was 19% to 23% in PD-L1-positive tumors and 9% to 13% even in PD-L1-negative tumors. In KEYNOTE-010 trial, which was a phase III clinical trial comparing pembrolizumab and docetaxel in a tumor PD-L1 expression of 1% or more, response rates were from 18.0% to 18.5%, and 9.3% in pembrolizumab and a docetaxel group, respectively. MSTs were from 10.4 to 12.7 months, and 8.5 months in pembrolizumab and docetaxel group, respectively, and hence a significant MST prolongation was found in pembrolizumab group as compared to docetaxel group. No significant difference in progression-free survival (PFS) was found as compared to docetaxel group. For patients with a tumor PD-L1 expression of 50% or more, a response rate in pembrolizumab group was from 29.1% to 30.2%, whereas that in docetaxel group was 7.9%. The MST was from 14.9 to 17.3 months in pembrolizumab group. In a patient population with a tumor PD-L1 expression of 50% or more, PFS was also significantly improved as compared to docetaxel group. Thus, it was revealed that, in a tumor PD-L1 highly expressing tumor, pembrolizumab provided a high antitumor effect and a prolonged prognosis.

An anti-PD-L1 antibody atezolizumab also showed a significant prolongation effect in previously treated non-small-cell lung cancer as with nivolumab and pembrolizumab, in BIRCH trial, in which an effect of single-agent administration was examined, and POPLAR trial, which was a phase II clinical trial comparing atezolizumab and docetaxel, in which MSTs were 12.6 and 9.7 months in an atezolizumab and a docetaxel group, respectively. Further, when PD-L1 was expressed in a tumor or tumor-infiltrating immune cells in a cancer immune microenvironment, the MST was from 15.1 to 15.5 months, demonstrating that the prognosis was further prolonged. In addition, a response rate of an atezolizumab group highly expressing PD-L1 in the cancer immune microenvironment was 38%, and that of a docetaxel group expressing no PD-L1 in the cancer immune microenvironment was only about 15%. Also in OAK trial, which was a phase III trial comparing atezolizumab and docetaxel in previously treated non-small-cell lung cancer, resulted in similar to those of POPLAR trial.

As described above, tumor PD-L1 expression in or immunocompetent cells is considered to be useful as a biomarker for responses to immune checkpoint inhibitors at present. However, even when PD-L1 is highly expressed (1% or more or 50% or more), response rates of immune checkpoint inhibitors are from 30% to 40%. In addition, approximately 10% of even PD-L1 low expressing or PD-L1-negative patients have responses.

Further, for each of immune checkpoint inhibitors (nivolumab, pembrolizumab, and atezolizumab), its own companion diagnostic method (PD-L1 expression analysis) is carried out, causing confusion in clinical settings.

CITATION LIST

Patent Literature

[PTL 1] JP 5709108 B2
[PTL 2] WO 2016/181912 A1

Non-Patent Literature

[NPL 1] Ohue Y, et al. Clin Cancer Res. 20(19), 5052-5063 (2014)
[NPL 2] Ohue Y, et al. Cancer Immunol Res. 4(12), 1049-1060 (2016)
[NPL 3] Hofmann O, et al. Proc Natl Acad Sci USA. 2008 Dec. 23; 105(51), 20422-7 (2008)
[NPL 4] Wang C, et al. Nat Commun. 2016 Jan. 27; 7: 10499

SUMMARY OF INVENTION

Technical Problem

An object of the present invention is to provide an examination method that can accurately predict the effect of cancer treatment or enables accurate prognosis prediction. Another object of the present invention is to provide a novel peptide and novel composition for inducing an immune response against cancer, and a screening method for the peptide.

Solution to Problem

The inventors of the present invention have made extensive investigations in order to achieve the above-mentioned objects, and as a result, have found that a treatment effect on cancer can be predicted or confirmed by detecting antibodies against cancer/testis antigens or an anti-p53 antibody. The inventors have found that IgG-type XAGE1 antibody (XAGE1-IgG) and IgA-type XAGE1 antibody (XAGE1-IgA), or IgG-type anti-NY-ESO-1 antibody (NY-ESO-1-IgG) suitably serves as an indicator for predicting effect of cancer treatment and prognosis prediction before cancer treatment. The inventors have also found a novel peptide for a cancer vaccine and a composition thereof. The inventors have also found a screening method for a peptide for a cancer vaccine. That is, the present invention encompasses the following aspects.

1. An examination method for cancer treatment effect, including detecting antibodies against cancer/testis antigens in clinical samples.
2. The method according to the above-mentioned item 1, wherein the cancer/testis antigens are at least one cancer/testis antigen selected from XAGE1, NY-ESO-1, MAEL, BAGE, BORIS, MAGE-B3, and SS4.
3. The examination method according to the above-mentioned item 1 or 2, wherein the detecting includes detecting an IgG-type antibody and an IgA-type antibody.
4. The method according to any one of the above-mentioned items 1 to 3, wherein the sample is a sample collected from a test subject before cancer treatment, and wherein the method includes examination for predicting an effect of the cancer treatment.
5. An examination method for a cancer treatment effect, including detecting an anti-p53 antibody in a sample.
6. The method according to any one of the above-mentioned items 1 to 5, further including judging that cancer treatment has an effect in at least one case selected from the group consisting of the following cases 1) to 4):
   1) antibodies against cancer/testis antigens or an anti-p53 antibody are positive;
   2) IgG-type antibodies against cancer/testis antigens or anti-p53 antibody are positive;
   3) IgG-type antibodies against cancer/testis antigens or anti-p53 antibody are positive, and IgA-type antibodies against cancer/testis antigens or anti-p53 antibody are negative; and
   4) antibodies against a plurality of cancer/testis antigens are positive.
7. A reagent kit for examining a cancer treatment effect, including: a support having immobilized thereon at least one selected from cancer/testis antigens, a peptide formed of part of a cancer/testis antigen, p53, and a peptide formed of part of p53; a reagent containing an anti-human IgG antibody; and a reagent containing an anti-human IgA antibody.
8. At least one peptide selected from the group consisting of the following items a) to f):
   a) a peptide formed of part of XAGE1 formed of an amino acid sequence set forth in SEQ ID NO: 3, the peptide having an amino acid sequence that allows extension and/or deletion of up to five amino acids at an N-terminal side and/or a C-terminal side of an amino acid sequence set forth in SEQ ID NO: 1;
   b) a peptide having an amino acid sequence obtained by conservatively substituting one or two amino acids in the amino acid sequence of the peptide of the item a);
   c) a pharmaceutically acceptable salt or solvate of the peptide of the item a) or b);
   d) a peptide formed of part of XAGE1 formed of the amino acid sequence set forth in SEQ ID NO: 3, the peptide having an amino acid sequence that allows extension and/or deletion of up to five amino acids at an N-terminal side and/or a C-terminal side of an amino acid sequence set forth in SEQ ID NO: 2;
   e) a peptide having an amino acid sequence obtained by conservatively substituting one or two amino acids in the amino acid sequence of the peptide of the item d); and
   f) a pharmaceutically acceptable salt or solvate of the peptide of the item d) or e).
9. A composition for inducing an immune response against cancer, including: at least one peptide selected from the group consisting of the items a) to c) of the above-mentioned item 8; and at least one peptide selected from the group consisting of the items d) to f) of the above-mentioned item 8.
10. The composition according to the above-mentioned item 9, wherein the cancer is XAGE1-positive lung cancer, liver cancer, prostate cancer, stomach cancer, malignant melanoma, breast cancer, esophageal cancer, kidney cancer, or bladder cancer.

11. The composition according to the above-mentioned item 9 or 10, wherein the composition is administered before immunotherapy or chemotherapy.

12. An agent for enhancing an effect of immunotherapy or chemotherapy on cancer, including: at least one peptide selected from the group consisting of the items a) to c) of the above-mentioned item 8; and at least one peptide selected from the group consisting of the items d) to f) of the above-mentioned item 8.

13. A screening method for a peptide for a cancer vaccine, including detecting an antibody against a cancer/testis antigen or an anti-p53 antibody in clinical samples.

14. The method according to the above-mentioned item 13, wherein the sample is a sample collected from a liquid containing B-cells subjected to stimulated culture with a candidate peptide for a cancer vaccine.

15. A method of preparing activated CD4-positive T-cells or activated CD8-positive T-cells, including a step of subjecting CD4-positive T-cells or CD8-positive T-cells obtained from peripheral blood to stimulated culture with SLP1 having an amino acid sequence set forth in SEQ ID NO: 1 and SLP2 having an amino acid sequence set forth in SEQ ID NO: 2.

16. A method of inducing an immune response, including using at least one peptide selected from the items a) to c) of the above-mentioned item 8 and at least one peptide selected from the items d) to f) of the above-mentioned item 8.

17. A method of augmenting an effect of immunotherapy or chemotherapy, including administering at least one peptide selected from the items a) to c) of the above-mentioned item 8 and at least one peptide selected from the items d) to f) of the above-mentioned item 8 before start of the immunotherapy or the chemotherapy.

18. A method of leading immunotherapy to a responder case, including increasing an antibody titer when it is not judged by the examination method of claim 1 that cancer treatment has an effect.

Advantageous Effects of Invention

The examination method of the present invention can accurately predict the effect and patient prognosis before cancer treatment. In addition, effect of cancer treatment can be confirmed after cancer treatment. More specifically, effects of chemotherapy (effect of an anticancer drug), immunotherapy, and immune checkpoint inhibitors can be accurately predicted. In particular, it becomes possible, without the use of PD-L1 expression, to determine whether or not cancer patients respond to immune checkpoint inhibitors. It is innovative that it has become possible to predict an effect even on a patient for whom the effect has not been able to be predicted on the basis of PD-L1 expression.

Immune checkpoint inhibitors are extremely expensive, and besides, there is at present no effective biomarker indicating the end of treatment therewith. In addition, there is a concern that, unlike conventional chemotherapy, immune checkpoint inhibitors, though effective in some patients, may also cause serious adverse events, specifically development of systemic autoimmune diseases. The examination method of the present invention enables prediction even for a patient on which the treatment effect is low, and the treatment may be stopped in consideration of balance with side effects. In view of the foregoing, the fact that the present invention allows selection of markedly responsive patients to immune checkpoint inhibitors is innovative also in medical costs including, for example, treatment cost and cost required for evaluating side effects.

The novel peptide, and the composition for inducing an immune response containing the novel peptide, of the present invention can each serve as a cancer therapeutic drug (cancer vaccine) by actively inducing XAGE1 immunity to induce an immune response against cancer. The novel peptide and composition for inducing an immune response of the present invention can induce an XAGE1-specific antibody, in particular, an IgG-type anti-XAGE1 antibody, and can also induce antigen-specific T-cells.

The novel peptide of the present invention and the composition for inducing an immune response of the present invention enable such innovative treatment as to lead non-responder patients or poor prognosis group of each of chemotherapy, immunotherapy, and treatment with immune checkpoint inhibitors to a treatment-responsive and favorable prognosis group by actively inducing XAGE1 immunity. Further, the peptide and the composition enable potent cancer immunotherapy through combined use with an existing treatment method or a novel treatment method. Further, the composition for inducing an immune response of the present invention is also excellent in safety.

The novel peptide of the present invention is a long-chain peptide unlike an epitope vaccine to be recognized by T-cells. Accordingly, the peptide contains various epitopes, and can induce a more potent immune response than a related-art epitope vaccine. Further, the combination of at least one peptide selected from the above-mentioned items a) to c) and at least one peptide selected from the above-mentioned items d) to f) can induce a still more potent immune response.

The screening method of the present invention enables the selection of a peptide suitable for a cancer vaccine.

The activated CD4-positive T-cells or activated CD8-positive T-cells obtained by the method of preparing activated CD4-positive T-cells or activated CD8-positive T-cells of the present invention can be used for cell therapy, such as adoptive immunity (T-cell) therapy.

BRIEF DESCRIPTION OF DRAWINGS

In FIGS. 5A and 5B, Tumor Infiltrate Lymphocytes (TIL) accumulation is shown. IgA-positive B-cells are increased in tumor as compared to peripheral blood. FIG. 5C shows high IgA-positive B-cell infiltration account for approximately 30%. FIG. 5D shows that tumor regulatory T-cells are increased in tumors with high IgA-positive B-cell infiltration. FIG. 5E shows that, in TIL as compared to peripheral blood, the production of an immunosuppressive cytokine IL-10 is found, and B-cells as well as T-cells produce IL-10. FIG. 5F shows that the IL-10-producing tumor-infiltrating B-cells shown in FIG. 5E are IgA-positive.

FIG. 15B shows that the spreading of immune responses against MAGE-B3 and SSX4 antigen was found at a high frequency in responders to anti-PD-1 antibody therapy, and was not found in non-responders.

DESCRIPTION OF EMBODIMENTS

Figure 1:
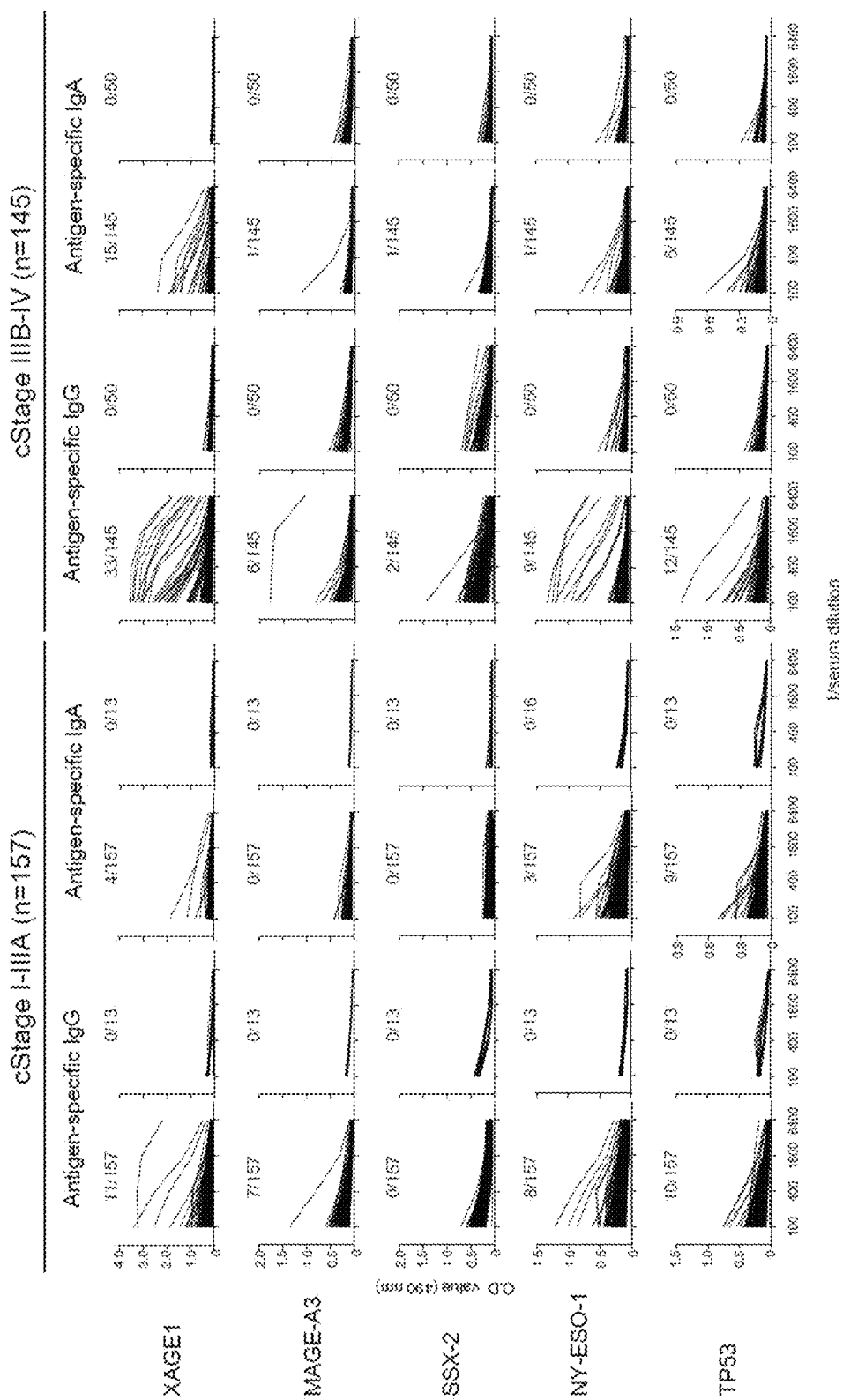
FIG. 1 shows the results of detection of antigen-specific IgG and antigen-specific IgA against cancer-associated antigens XAGE1, MAGE-A3, SSX-2, NY-ESO-1, and TP53 for sera collected from 157 early or locally advanced lung adenocarcinoma (cStage I-IIIA) patients and 145 advanced (cStage IIIB-IV) lung adenocarcinoma patients.

An examination method of the present invention includes detecting antibodies against cancer/testis antigens or an anti-p53 antibody in clinical samples. In addition, a screening method for a peptide for a cancer vaccine of the present invention also includes detecting antibodies against cancer/testis antigens or an anti-p53 antibody in clinical samples.

Cancer/testis antigens (CT antigen) in each of the examination method and screening method of the present invention is not particularly limited, and is an antigen expressed in cancer cells and expressed only in testis among normal tissues. The present invention includes detecting antibodies against CT antigens, and preferred examples of CT antigens include XAGE1, NY-ESO-1, MAEL, BAGE, BORIS, MAGE-B3, and SSX4. More preferred examples of CT antigens include XAGE1 and NY-ESO-1.

In each of the examination method and screening method of the present invention, an IgG-type antibodies against CT antigens or anti-p53 antibody is preferably detected. Preferred examples of antibodies against CT antigens include anti-XAGE1, anti-NY-ESO-1, anti-MAEL, anti-BAGE, anti-BORIS, anti-MAGE-B3, and anti-SSX4 antibodies. Each of those antibodies is preferably of an IgG type. More preferred examples of the antibody include IgG-type anti-XAGE1 and IgG-type anti-NY-ESO-1 antibody.

It is still more preferred that an IgA-type antibodies against CT antigens be detected in addition to the IgG-type antibodies against CT antigens. A suitable example of the IgA-type antibodies against CT antigens is an IgA-type anti-XAGE1 antibody. It is preferred that the IgG-type anti-XAGE1 antibody and the IgA-type anti-XAGE1 antibody be detected.

As used herein, the term "cancer vaccine" means a pharmaceutical composition capable of inducing immune responses against cancer antigens, and immune response induction includes humoral and/or cell-mediated immunity induction.

In examination methods according to one embodiment of the present invention, antibodies against CT antigens or an anti-p53 antibody in clinical samples collected from patients before cancer treatment is detected. In addition, in examination methods according to one embodiment of the present invention, antibodies against CT antigens or an anti-p53 antibody in clinical samples collected from patients after cancer treatment is detected.

When antibodies against CT antigens or the anti-p53 antibody in clinical samples collected from patients before cancer treatment is detected, effect and prognosis of cancer treatment can be predicted before cancer treatment.

When antibodies against CT antigens or the anti-p53 antibody in clinical samples collected from patients after cancer treatment is detected, effect of the cancer treatment can be confirmed and prognosis thereof can be predicted after cancer treatment. Further, effect and prognosis of subsequent treatment can be predicted.

The examination methods of the present invention are suited to prediction and confirmation of effects of various cancer treatments, and prediction of prognoses thereof, and are suited to prediction and confirmation of effect of chemotherapy or immunotherapy, and prediction of prognoses thereof. The examination methods of the present invention are more suited to prediction of effect of immunotherapy, and is particularly suited to prediction of effect of immune checkpoint inhibitors.

Chemotherapy encompasses administration of various anticancer drugs, such as platinum agents. Immunotherapy encompasses immunosuppression-inhibiting therapy (treatment with immune checkpoint inhibitors), cytokine (e.g., IL-2) therapy, BRM therapy (e.g., immunostimulator), cancer vaccine, and the like. Immune checkpoint inhibitors encompass PD-1 inhibitors (e.g., nivolumab), CTLA-4 inhibitors (e.g., ipilimumab), and the like.

In an examination method according to one embodiment of the present invention, clinical samples collected from patients before cancer treatment is used as an object to be examined. As used herein, the phrase "before cancer treatment" means before start of cancer treatment whose effect is to be predicted. That is, "before cancer treatment" in the present invention includes: before cancer treatment is newly started; before administration of pharmaceutical agents for cancer treatment; before administration of pharmaceutical agents during ongoing cancer treatment; before changing pharmaceutical agents for cancer treatment; before changing cancer treatment plans; and during a period of investigation as to whether or not cancer treatment is stopped.

In an examination method according to one embodiment of the present invention, clinical samples collected from patients after cancer treatment is used as an object to be examined. As used herein, the phrase "after cancer treatment" means a stage of confirming, after a certain period from start of cancer treatment for which a particular cancer therapeutic drug has been chosen, effect of cancer therapeutic drugs. That is, the "after cancer treatment" in the present invention includes: before administration of additional pharmaceutical agents during ongoing cancer treatment; before changing pharmaceutical agents for cancer treatment; before changing cancer treatment plans; and a stage of investigation as to whether or not cancer treatment is stopped.

The "clinical samples" in the screening method of the present invention is preferably clinical samples collected from a liquid containing B-cells subjected to stimulated culture with a candidate peptide fora cancer vaccine. For example, a supernatant of a culture medium after stimulated culture of a mononuclear cell-containing fraction or a B-cell-containing fraction obtained from human blood with a candidate peptide for a cancer vaccine in the presence of CD4-positive T-cells and CD8-positive T-cells may be used.

As used herein, the concept "treatment effect" encompasses suppression of pathological progression of cancer, regression of cancer, disappearance of cancer, suppression of recurrence, suppression of metastasis, prolongation of a survival time, and the like. Treatment effect is represented in terms of response rate, survival rate, survival time, or the like.

The cancer in the "cancer treatment" in the examination method of the present invention is not particularly limited, and may be any cancer. A suitable example of the cancer is XAGE1-positive or NY-ESO-1-positive cancer. In addition, the cancer in the "peptide for a cancer vaccine" to be obtained by screening methods of the present invention is not particularly limited, and may be any cancer. A suitable example of the cancer is XAGE1-positive cancer. Examples of cancer in each of examination methods of the present invention and the screening methods of the present invention include lung cancer, liver cancer, prostate cancer, stomach cancer, malignant melanoma, breast cancer, esophageal cancer, kidney cancer, and bladder cancer. A suitable example of cancer is lung cancer, and a particularly suitable example thereof is non-small-cell lung cancer. Further, the examination of the present invention is suited to prediction of effect of intractable advanced non-small-cell lung cancer treatment or advanced lung adenocarcinoma treatment.

XAGE1 (X Antigen Family, Member 1) is a known cancer/testis antigen encoded by an XAGE1 gene and also known as cancer/testis antigen 12.1 (CT12.1). Five kinds of genes, i.e., XAGE1a to XAGE1e have heretofore been identified. It is known that the associated protein is GAGED2, and there are two kinds of isoforms, i.e., GAGED2a and GAGED2d. In addition, four kinds of alternative splice variants, i.e., XAGE1a, XAGE1b, XAGE1c, and XAGE1d have heretofore been identified (Sato et al., Cancer Immunity, vol. 7, page 5 (2007)). XAGE1a and XAGE1b encode an XAGE1 (GAGED2a) protein formed of 81 amino acids, and XAGE1d encodes an XAGE1 (GAGED2d) protein formed of 69 amino acids.

The amino acid sequences of XAGE1 for various animal species are known. For example, the sequence of human XAGE1 (GAGED2a) is available as NCBI Reference Sequence: NP_001091073.2 and NP_001091063.2, and the sequence of human XAGE1 (GAGED2d) is available as NCBI Reference Sequence: NP 001091074.1.

```
Human XAGE1 (GAGED2a):
                                        (SEQ ID NO: 3)
mespkkknqq lkvgilhlgs rqkkiriqlr sqcatwkvic kscisqtpgi nldlgsgvkv kiipkeehck mpeageeqpq v
```

The anti-XAGE1 antibody measured in the examination method or screening method of the present invention is an antibody against XAGE1 (GAGED2a) (hereinafter referred to simply as XAGE1).

A method of detecting the anti-XAGE1 antibody detected in the examination method or screening method of the present invention is not particularly limited, but an example thereof is a method involving detecting binding to an antigen. The antigen for the binding may be full-length XAGE1, or may be a partial peptide formed of part of the amino acid sequence thereof. Full-length XAGE1 is preferably used.

In an examination method or screening method according to one embodiment of the present invention, an IgG-type anti-XAGE1 antibody is detected. It is preferred that the IgG-type anti-XAGE1 antibody (XAGE1-IgG) and an IgA-type anti-XAGE1 antibody (XAGE1-IgA) be detected. A detection method for the IgG-type antibody is not particularly limited, but for example, a labeled anti-human IgG antibody may be used. In addition, a detection method for the IgA-type antibody is also not particularly limited, but for example, a labeled anti-human IgA antibody may be used.

An examination method or screening method according to one embodiment of the present invention includes a step of detecting XAGE1-IgG and/or XAGE1-IgA. XAGE1-IgG is a biomarker indicating that an immune response against an autologous tumor is enhanced, and XAGE1-IgA is a biomarker indicating that the immune response against an autologous tumor is reduced (suppressed). It has been found for the first time that such markers are applicable to prediction of treatment effect of cancer therapeutic drugs.

NY-ESO-1 is also a known cancer/testis antigen. NY-ESO-1 is expressed in various tumors, including malignant melanoma, at various levels ranging from 5% to 40%, but is expressed only in testes among normal tissues. NY-ESO-1 protein is formed of 180 amino acids, and its sequence is available as GenBank: CAA05908.1.

```
Human NY-ESO-1:
                                        (SEQ ID NO: 4)
mqaegrgtgg stgdadgpgg pgipdgpggn aggpgeagat ggrgprgaga arasgpggga prgphggaas glngccrcga rgpesrllef ylampfatpm eaelarrsla qdapplpvpg vllkeftvsg niltirltaa dhrqlqlsis sclqqlsllm witqcflpvf laqppsgqrr
```

A method of detecting the anti-NY-ESO-1 antibody serving as an object to be detected in the examination method or screening method of the present invention is not limited, but an example thereof is a method involving detecting binding to an antigen. The antigen for the binding may be full-length NY-ESO-1, or may be a partial peptide formed of part of the amino acid sequence thereof. Full-length NY-ESO-1 is preferably used.

In an examination method or screening method according to one embodiment of the present invention, an IgG-type anti-NY-ESO-1 antibody is detected. Further, an IgA-type anti-NY-ESO-1 antibody may be detected. A detection method for the IgG-type antibody is not particularly limited. For example, a labeled anti-human IgG antibody may be used. In addition, a detection method for the IgA-type antibody is also not particularly limited, but for example, a labeled anti-human IgA antibody may be used.

MAEL, BAGE, BORIS, MAGE-B3, and SSX4 are also known cancer/testis antigens. These antigens are expressed in various tumors at various levels, but are expressed only in testes among normal tissues. p53 is known as a cancer suppressor protein.

A method of detecting the anti-MAEL antibody, the anti-BAGE antibody, the anti-BORIS antibody, the anti-MAGE-B3 antibody, the anti-SSX4 antibody, and the anti-p53 antibody each serving as an object to be detected in the examination method or screening method of the present invention is not limited, but an example thereof is a method involving detecting binding to an antigen. The antigen for the binding may be a full-length one, or may be a partial peptide formed of part of the amino acid sequence thereof.

In the examination method or screening method of the present invention, an IgG-type anti-MAEL antibody, an IgG-type anti-BADE antibody, an IgG-type anti-BORIS antibody, an IgG-type anti-MAGE-B3 antibody, an IgG-type anti-SSX4 antibody, and an IgG-type anti-p53 antibody are detected. Further, an IgA-type antibody may be detected. A detection method for the IgG-type antibody is not particularly limited, but for example, a labeled anti-human IgG antibody may be used. In addition, a detection method for the IgA-type antibody is also not particularly limited, but for example, a labeled anti-human IgA antibody may be used.

A method of detecting the antibody against each CT antigen or the anti-p53 antibody is not particularly limited as long as the amount, concentration, or antibody titer of the antibody can be measured by the method, and measurement may be performed using a technique known in the art. For example, measurement may be performed by an ELISA method, radioimmunoassay, an immunoprecipitation method, an affinity column method, or the like.

The "test subject" in the examination method of the present invention is not particularly limited, and widely encompasses mammals in general (e.g., humans, mice, rats, monkeys, dogs, cats, cattle, horses, pigs, sheep, goats, rabbits, and hamsters). Of those, humans are preferred. When the test subject is a human, not only a cancer patient or a patient suspected of having cancer, but also a healthy individual may serve as the test subject. The sex, age, and the like of the test subject are not particularly limited.

Examples of the "clinical samples" in the examination method of the present invention may include blood (e.g., serum, plasma, or blood cells), urine, feces, sputum, pleural/ascitic fluid, bronchoalveolar lavage fluid, peritoneal lavage fluid, a biopsy tissue, and surgically resected specimens. A preferred example of the sample is serum.

In an examination method or screening method according to a preferred embodiment of the present invention, it is judged that cancer treatment has an effect in at least one patient selected from the group consisting of the following patients 1) to 4):

1) antibodies against cancer/testis antigens or an anti-p53 antibody are positive;
2) IgG-type antibodies against cancer/testis antigens or anti-p53 antibody are positive;
3) IgG-type antibodies against cancer/testis antigens or anti-p53 antibody are positive, and IgA-type antibodies against cancer/testis antigens or anti-p53 antibody are negative; and
4) antibodies against a plurality of cancer/testis antigens are positive.

In an examination method or screening method according to a preferred embodiment of the present invention, it is judged that cancer treatment has an effect in patients where antibodies against CT antigens or the anti-p53 antibody are positive. Preferred specific examples thereof include anti-XAGE1 antibody, anti-NY-ESO-1 antibody, anti-MAEL antibody, anti-BADE antibody, anti-BORIS antibody, anti-MAGE-B3 antibody, anti-SSX4 antibody, and anti-p53 antibody. Antibodies against CT antigens or anti-p53 antibody are still more preferably IgG-type antibodies. A preferred specific example thereof is XAGE1-IgG or NY-ESO-1-IgG.

In addition, in a preferred embodiment, it is judged that cancer treatment has effect in patients where an IgG-type antibodies against CT antigens or anti-p53 antibody are positive and IgA-type antibodies against CT antigens or anti-p53 antibody are negative. A preferred specific example thereof is a patient in which XAGE1-IgG or NY-ESO-1-IgG is positive and XAGE1-IgA is negative, and a particularly preferred specific example thereof is a patient in which XAGE1-IgG is positive and XAGE1-IgA is negative.

Patient in which antibodies against CT antigens or anti-p53 antibody are positive is a patient in which amount, concentration, or antibody titer of antibodies against CT antigens or anti-p53 antibody is equal to or higher than cutoff value. Patient in which antibodies against CT antigens or anti-p53 antibody is negative is a patient in which amount, concentration, or antibody titer of antibodies against CT antigens or anti-p53 antibody is equal to or lower than cutoff value. The cutoff value may be, for example, a 10-to 1,000-fold antibody titer, a 20- to 500-fold antibody titer, a 50- to 200-fold antibody titer, or a 100-fold antibody titer with respect to antibody titer of healthy individuals. In addition, cutoff value may be set to be a mean+3SD of 50 or more sera of healthy adults, or the like. Preferably, it is judged that cancer treatment has effect in patient where amount, concentration, or antibody titer of XAGE1-IgG or NY-ESO-1-IgG is equal to or higher than cutoff value.

An examination method according to one embodiment of the present invention includes a step of detecting an antibodies against CT antigen or anti-p53 antibody in clinical samples. The samples are preferably clinical samples collected from patients before cancer treatment. Specific examples of antibodies against CT antigens include anti-XAGE1 antibody and anti-NY-ESO-1 antibody. More preferred specific examples thereof include: XAGE1-IgG; a combination of XAGE1-IgG and XAGE1-IgA; NY-ESO-1-IgG; and a combination of NY-ESO-1-IgG and XAGE1-IgA.

An examination method according to one embodiment of the present invention includes the steps of: detecting an amount, concentration, or antibody titer of XAGE1-IgG in clinical samples collected from patients; and detecting an amount, concentration, or antibody titer of XAGE1-IgA in the same clinical sample. The presence of XAGE1-IgA indicates that immunity is suppressed, and hence it can be judged that cancer treatment has an effect in the case where the amount, concentration, or antibody titer of XAGE1-IgG is equal to or higher than cutoff value, and that of XAGE1-IgA is equal to or lower than cutoff value.

XAGE1-IgG is a biomarker indicating that an immune response against an autologous tumor is enhanced. Meanwhile, it has been found that IgA-positive regulatory B-cells are increased in cancer locally, and hence XAGE1-IgA serves as a biomarker indicating that immune responses against autologous tumor is reduced. In about a half of patients having XAGE1-IgG, XAGE1-IgA response is observed.

The screening method of the present invention includes, for example, the steps of: subjecting B-cells separated from human blood to stimulated culture with a candidate peptide for a vaccine; and detecting antibodies against CT antigens or an anti-p53 antibody in a culture supernatant.

The screening method preferably further includes a step of judging that the candidate peptide has a cancer treatment effect in patients where antibodies against CT antigens or anti-p53 antibody are positive. The screening method suitably includes a step of judging that the candidate peptide has cancer treatment effect in patients where XAGE1-IgA is negative and XAGE1-IgG or NY-ESO-1-IgG is positive.

In addition, in an examination method or screening method according to a preferred other embodiment of the present invention, it is judged that cancer treatment has an effect in patients where antibodies against a plurality of CT antigens are positive. In this embodiment, the examination method or the screening method includes the steps of: detecting an amount, concentration, or antibody titer of antibodies against CT antigens in a sample collected from patients; and detecting an amount, concentration, or antibody titer of antibodies against another CT antigens different from the foregoing CT antigen in the same sample. The antibodies against CT antigens to be examined are not particularly limited, but preferably include anti-XAGE1 antibody, anti-NY-ESO-1 antibody, anti-MAEL antibody, anti-BADE antibody, anti-BORIS antibody, anti-MAGE-B3 antibody, or anti-SSX4 antibody. A patient in which antibodies against a plurality of CT antigens are detected has immune responses against multiple antigens and is in an immune-activated state, thereby being responsive to cancer treatment, such as immunotherapy. The plurality needs to be 2 or more, and is preferably 3 or more. The upper limit thereof is not limited, but is specifically, for example, 50 or less, 40 or less, 30 or less, 20 or less, or 10 or less from the viewpoint of the complexity of the examination.

It has become possible to accurately predict a cancer treatment effect by using antibodies against anti-CT antigens or anti-p53 antibody as an indicator (by detecting immune responses against CT antigens or p53), preferably using anti-XAGE1 antibody or anti-NY-ESO-1 antibody as indicators (detecting immune responses against XAGE1 or NY-ESO-1). Positivity for anti-XAGE1 antibody or anti-NY-ESO-1 antibody more clearly determines effect of anti-PD-1 antibody therapy than a known biomarker. In particular, it has become possible to clearly determine responder patients to immune checkpoint inhibitors. The response rate is 30% even when PD-L1 expression is positive, and 10% of even negative patients are responder patients. Therefore, it is innovative that responder patients can be clearly determined with those biomarkers.

When it is judged by the examination method of the present invention that cancer treatment has an effect, immunotherapy or chemotherapy may be performed. When it is not judged by the examination methods of the present invention that cancer treatment has an effect, the antibody titer may be increased to lead immunotherapy or chemotherapy to responder patients. In one embodiment, a method of increasing the antibody titer is, for example, administration of vaccines. The vaccine is preferably a vaccine containing a CT antigen, more preferably a vaccine containing at least one CT antigen selected from the group consisting of XAGE1, NY-ESO-1, MAEL, BAGE, BORIS, MAGE-B3, and SSX4, or a peptide formed of part of any such antigen.

The present application also encompasses an invention directed to a reagent kit. The invention directed to a reagent kit is directed to a reagent kit for examining cancer treatment effects including: a support having immobilized thereon at least one selected from the group consisting of a CT antigen, a peptide formed of part of a CT antigen, p53, and a peptide formed of part of p53; a reagent containing an anti-human IgG antibody; and a reagent containing an anti-human IgA antibody.

A preferred embodiment is a reagent kit for examining a cancer treatment effect including: a support having immobilized thereon at least one peptide selected from the group consisting of XAGE1, a peptide formed of part of XAGE1, NY-ESO-1, and a peptide formed of part of NY-ESO-1; a reagent containing an anti-human IgG antibody; and a reagent containing an anti-human IgA antibody. This kit is a reagent kit for examining the effect of cancer treatment.

The peptide formed of part of XAGE1 is a peptide having a sequence formed of part of the amino acid sequence set forth in SEQ ID NO: 3. It is preferred that the peptide contain 10 or more amino acids and contain one or more epitopes. The peptide formed of part of NY-ESO-1 is a peptide having an amino acid sequence formed of part of the amino acid sequence set forth in SEQ ID NO: 4. It is preferred that the peptide contain 10 or more amino acids and contain one or more epitopes.

The support having a peptide immobilized thereon included in the reagent kit of the present invention has immobilized thereon at least one selected from the group consisting of a CT antigen, a peptide formed of part of a CT antigen, p53, and a peptide formed of part of p53. It is preferred that at least one selected from the group consisting of XAGE1, a peptide formed of part of XAGE1, NY-ESO-1, and part of NY-ESO-1 be immobilized. The support is not particularly limited, and examples thereof include a plate and a stick.

The reagent kit of the present invention includes the reagent containing an anti-human IgG antibody and the reagent containing an anti-human IgA antibody in addition to the support having immobilized thereon a peptide. Those antibodies are preferably labeled. In addition, the kit of the present invention may contain a reagent for causing a reaction with a label, a diluent or the like, an additional reagent, and an instrument for examination.

An invention directed to a peptide of the present application is directed to at least one peptide selected from the group consisting of the following items a) to f):

a) a peptide formed of part of XAGE1 formed of an amino acid sequence set forth in SEQ ID NO: 3, the peptide having an amino acid sequence that allows extension and/or deletion of up to five amino acids at an N-terminal side and/or a C-terminal side of an amino acid sequence set forth in SEQ ID NO: 1;

b) a peptide having an amino acid sequence obtained by conservatively substituting one or two amino acids in the amino acid sequence of the peptide of the item a);

c) a pharmaceutically acceptable salt or solvate of the peptide of the item a) or b);

d) a peptide formed of part of XAGE1 formed of the amino acid sequence set forth in SEQ ID NO: 3, the peptide having an amino acid sequence that allows extension and/or deletion of up to five amino acids at an N-terminal side and/or a C-terminal side of an amino acid sequence set forth in SEQ ID NO: 2;

e) a peptide having an amino acid sequence obtained by conservatively substituting one or two amino acids in the amino acid sequence of the peptide of the item d); and f) a pharmaceutically acceptable salt or solvate of the peptide of the item d) or e).

The amino acid sequence of the peptide of the present invention is designed on the basis of the sequences of SEQ ID NO: 1, SEQ ID NO: 2, and SEQ ID NO: 3, and the peptide may be synthesized by a general method. The number of amino acids of the peptide preferably falls within the range of from 20 to 30. In addition, the peptide of the present invention is a peptide that may be selected by the above-mentioned screening method for a peptide for a cancer vaccine.

In the conservative substitution, for example, one amino acid is substituted with an amino acid having a similar structure or similar characteristics like the substitution of a hydrophobic amino acid with another hydrophobic amino acid. Further, one amino acid is replaced with an amino acid identical or similar thereto in size and chemical properties like the substitution of leucine with isoleucine. In research into sequence diversity in a naturally occurring homologous protein family, some kinds of amino acid substitutions are more acceptable than other amino acid substitutions in many cases. In the more acceptable amino acid substitutions, correlations of being similar in size, charge, polarity, and hydrophobicity are often exhibited between original amino acids and substitutes therefor. This is the basis for the definition of the "conservative substitution". The conservative substitution may be herein defined as replacement within one of the following five groups: Group 1—aliphatic, nonpolar or slightly polar residues each having a small molecular weight (Ala, Ser, Thr, Pro, and Gly); Group 2—polar, negatively charged residues and amides thereof (Asp, Asn, Glu, and Gln); Group 3—polar, positively charged residues (His, Arg, and Lys); Group 4—aliphatic nonpolar residues each having a large molecular weight (Met, Leu, Ile, Val, and Cys); and Group 5—aromatic residues each having a large molecular weight (Phe, Tyr, and Trp).

The C-terminus of the peptide of the present invention may be an amide or an ester. In addition, an amino group at the N-terminus or, for example, OH, $NH_2$, or SH on the side chain of an amino acid inside the molecule may be protected with an appropriate protecting group (e.g., a $C_{1-6}$ acyl group, such as a formyl group or an acetyl group). In addition, the peptide of the present invention also encompasses a so-called glycopeptide having a glycan linked thereto and the like. In addition, some of the amino acids may be D-amino acids.

As a salt of the peptide of the present invention, there is given, for example, a physiologically acceptable acid addition salt, in particular. The peptide of the present invention may be in the form of a solvate. A solvent is not particularly limited as long as the solvent is pharmaceutically acceptable, and examples thereof include water, ethanol, glycerol, and acetic acid. The peptide of the present invention may be converted into a prodrug. The prodrug may be designed to be converted into the peptide of the present invention under a physiological condition in vivo.

The peptide of the present invention may be produced in accordance with a known synthesis method for a peptide. The synthesis method for a peptide may be based on, for example, any of a solid-phase synthesis method and a liquid-phase synthesis method. That is, the target peptide may be produced by: condensing a partial peptide or amino acids that may constitute the peptide of the present invention with the remaining portion; and when the product has a protecting group, removing the protecting group as required.

In the peptide as defined in the above-mentioned item a), the number of amino acids in the extension and/or deletion is up to 5, preferably 4, more preferably 3, more preferably 2, still more preferably 1, most preferably 0.

In the peptide as defined in the above-mentioned item b), the number of amino acids to be conservatively substituted is 2 or 1, more preferably 1.

In the peptide as defined in the above-mentioned item d), the number of amino acids in the extension and/or deletion is up to 5, preferably 4, more preferably 3, more preferably 2, still more preferably 1, most preferably 0.

In the peptide as defined in the above-mentioned item e), the number of amino acids to be conservatively substituted is 2 or 1, more preferably 1.

A preferred example of the peptide of the present invention is at least one peptide selected from the group consisting of the following items a1) to f1):

a1) a peptide formed of part of XAGE1 formed of an amino acid sequence set forth in SEQ ID NO: 3, the peptide having an amino acid sequence that allows extension and/or deletion of up to three amino acids at an N-terminal side and/or a C-terminal side of an amino acid sequence set forth in SEQ ID NO: 1;

b1) a peptide having an amino acid sequence obtained by conservatively substituting one amino acid in the amino acid sequence of the peptide of the item a1);

c1) a pharmaceutically acceptable salt or solvate of the peptide of the item a1) or b1);

d1) a peptide formed of part of XAGE1 formed of the amino acid sequence set forth in SEQ ID NO: 3, the peptide having an amino acid sequence that allows extension and/or deletion of up to three amino acids at an N-terminal side and/or a C-terminal side of an amino acid sequence set forth in SEQ ID NO: 2;

e1) a peptide having an amino acid sequence obtained by conservatively substituting one amino acid in the amino acid sequence of the peptide of the item d); and f1) a pharmaceutically acceptable salt or solvate of the peptide of the item d) or e).

Most preferred examples of the peptide of the present invention include SLP1 and SLP2. SLP1 and SLP2 are each a long-chain peptide having 25 amino acid residues. SLP1 has the amino acid sequence set forth in SEQ ID NO: 1, and SLP2 has the amino acid sequence set forth in SEQ ID NO: 2.

```
SLP1:
                                       (SEQ ID NO: 1)
NQQLKVGILHLGSRQKKIRIQLRSQ

SLP2:
                                       (SEQ ID NO: 2)
ISQTPGINLDLGSGVKVKIIPKEEH
```

SLP1 has an amino acid sequence of amino acids 8 to 32 of XAGE1 (SEQ ID NO: 3), and SLP2 has an amino acid sequence of amino acids 44 to 68 of XAGE1.

An invention directed to a composition for inducing an immune response against cancer of the present application contains at least one peptide selected from the above-mentioned items a) to c) and at least one peptide selected from the above-mentioned items d) to f). The composition more preferably contains at least one peptide selected from the above-mentioned items a1) to c1) and at least one peptide selected from the above-mentioned items d1) to f1). The composition still more preferably contains SLP1 and SLP2. Through the combined use of those peptides, an effect that has not been able to be achieved with one of the peptides alone has been achieved.

An invention directed to an agent for enhancing an effect of immunotherapy or chemotherapy on cancer of the present application contains at least one peptide selected from the group consisting of the above-mentioned items a) to c) and at least one peptide selected from the group consisting of the above-mentioned items d) to f). The agent more preferably contains at least one peptide selected from the above-mentioned items a1) to c1) and at least one peptide selected from the above-mentioned items d1) to f1). The agent still more preferably contains SLP1 and SLP2. Through the combined use of those peptides, an effect that has not been able to be achieved with one of the peptides alone has been achieved.

The composition for inducing an immune response of the present invention and the effect-enhancing agent of the present invention may each also be called a cancer vaccine.

The composition for inducing an immune response of the present invention is used for inducing immune responses of mammals (e.g., mice, rats, hamsters, rabbits, cats, dogs, cattle, sheep, monkeys, and humans).

The composition for inducing an immune response of the present invention activates humoral immunity or cell-mediated immunity to enhance an immune response against cancer, and can be used for the treatment of cancer. In addition, the composition for inducing an immune response of the present invention can augment the effect of chemotherapy, immunotherapy, or cancer treatment with an immune checkpoint inhibitor. Further, the composition for inducing an immune response of the present invention can lead a non-responder case or poor prognosis group of each of chemotherapy, immunotherapy, and treatment with an immune checkpoint inhibitors to a treatment-responsive and favorable prognosis group by actively inducing XAGE1 immunity. In addition, the composition for inducing an immune response of the present invention is also excellent in safety.

The composition of the present invention can induce an immune response against cancer expressing XAGE1, and can be used for the treatment of the cancer, and in addition, can enhance a treatment effect on the cancer. In addition, the composition can lead a non-responder case or poor prognosis group of the treatment of the cancer to a treatment-responsive and favorable prognosis group by actively inducing XAGE1 immunity. Examples of the cancer to be treated may include lung cancer, liver cancer, prostate cancer, stomach cancer, malignant melanoma, breast cancer, esophageal cancer, kidney cancer, and bladder cancer. Lung cancer is given as the cancer to which the composition is particularly suited, and among lung cancers, the composition is suited to the induction of an immune response to non-small-cell lung cancer or lung adenocarcinoma, in particular, advanced non-small-cell lung cancer or lung adenocarcinoma.

The composition for inducing an immune response of the present invention can induce the production of an anti-XAGE1 antibody. In particular, the composition can induce the production of XAGE1-IgG. An XAGE1-IgG-positive patient or object to be treated has a favorable prognosis and is treatment-responsive, and hence the composition for inducing an immune response of the present invention can lead, for example, a patient expected to have a poor prognosis or be non-responsive to treatment even for each of chemotherapy, immunotherapy, and treatment with immune checkpoint inhibitors to have a favorable prognosis or be treatment-responsive.

The inventors of the present invention have previously prepared an epitope vaccine containing 16 or 17 amino acids that are part of XAGE1. However, the peptide of the present invention is a long-chain peptide unlike an epitope vaccine to be recognized by T-cells, and hence contains various epitopes. Further, the combination of at least one peptide selected from the group consisting of the above-mentioned items a) to c) and at least one peptide selected from the group consisting of the above-mentioned items d) to f) can induce a more potent immune response than a related-art epitope vaccine.

The composition for inducing an immune response of the present invention may contain an adjuvant in order to enhance the immune response. In addition, the composition may contain a pharmacologically acceptable support or stabilizing agent. The composition for inducing an immune response of the present invention is produced in accordance with known means generally used in a production method for a pharmaceutical formulation, and may be safely administered, for example, as an injection by a parenteral route (e.g., intravenous injection or intramuscular injection).

Examples of the pharmacologically acceptable support that may be used for the production of the composition for inducing an immune response of the present invention include various organic or inorganic support substances commonly used as formulation materials, and examples thereof include: an excipient, a lubricant, a binder, and a disintegrant in a solid formulation; and a solvent, a solubilizing agent, a suspending agent, a tonicity agent, a buffer, and a soothing agent in a liquid formulation. Further, as required, a general additive, such as an antiseptic agent, an antioxidant, a colorant, a sweetening agent, an adsorbent, or a humectant, may also be appropriately used in an appropriate amount.

The prepared injection may be a solution, or may be a solid formulation to be dissolved before use. At the time of administration, in the case of the solid formulation, the solid formulation may be dissolved in a commonly used aqueous diluent and used as a solution. The aqueous diluent encompasses an aqueous glucose solution, physiological saline, Ringer's solution, a nutritional supplement solution, and the like.

In the composition for inducing an immune response of the present invention, the content of the peptide of the present invention varies depending on the form of the formulation, but is generally from about 0.1 wt % to about 100 wt %, preferably from about 10 wt % to about 99.9 wt %, more preferably from about 20 wt % to about 90 wt % with respect to the entirety of the formulation. A ratio between the contents of at least one peptide selected from the above-mentioned items a) to c) and at least one peptide selected from the above-mentioned items d) to f) is appropriately adjusted. The ratio is, for example, from 1:9 to 9:1, from 3:7 to 7:3, or 5:5. The dose of the composition for inducing an immune response of the present invention varies depending on, for example, an administration route, symptoms, and the age of a patient. For example, when the composition is parenterally administered by intravenous administration or the like, the composition may be administered at a daily dose in terms of the peptide of from about 0.005 mg to about 50 mg, preferably from about 0.05 mg to about 10 mg per kg body weight.

The composition for inducing an immune response according to one aspect of the present invention may be administered before other chemotherapy, immunotherapy, or administration of an immune checkpoint inhibitors. When the composition for inducing immune responses of the present invention is administered in advance, effect of chemotherapy, immunotherapy, or immune checkpoint inhibitors can be enhanced. For example, the composition may be administered from 1 day to a half year, preferably from 1 week to 3 months, more preferably from 2 weeks to 2 months before the administration of any such pharmaceutical agent. In one preferred embodiment, the composition may be administered from 28 days to 3 months before the administration of immune checkpoint inhibitors.

The present invention is also directed to a method of preparing activated CD4-positive T-cells or activated CD8-positive T-cells, including a step of subjecting CD4-positive T-cells or CD8-positive T-cells obtained from peripheral blood of a patient to stimulated culture with SLP1 having an amino acid sequence set forth in SEQ ID NO: 1 and SLP2 having an amino acid sequence set forth in SEQ ID NO: 2.

More specifically, CD4-positive T-cells or CD8-positive T-cells are separated from peripheral blood mononuclear cells, and subjected to stimulated culture in the presence of SLP1 and SLP2 for from 3 days to 21 days, preferably from 7 days to 18 days. After that, the cells are restimulated with SLP1 and/or SLP2 in the presence of antigen-presenting cells for from 3 hours to 24 hours, preferably from 6 hours to 18 hours. Thus, activated CD4-positive T-cells or activated CD8-positive T-cells may be obtained. The concentration of each of SLP1 and SLP2 at the time of the stimulated culture is from 0.1 μM to 10 μM, preferably from 0.1 μM to 1 μM.

The obtained activated CD4-positive T-cells and activated CD8-positive T-cells may be used for cell therapy. For example, the activated CD4-positive T-cells and activated CD8-positive T-cells may be utilized for adoptive immunotherapy by being administered to the patient who donated the peripheral blood himself/herself.

Now, the present invention is more specifically described by way of Examples and Test Examples. However, the present invention is by no means limited thereto.

EXAMPLES

Blood used in Examples was donated from patients before cancer treatment with informed consent.

Example 1

<Detection of XAGE1-IgG and XAGE1-IgA>

An XAGE1 protein (81 amino acids, SEQ ID NO: 3) used was synthesized by GL Biochem (Shanghai, China). The synthesized XAGE1 protein was purified with an HPLC column, and the purity was confirmed to be 90% or more.

XAGE1 at a concentration of 1 µg/ml (carbonate buffer, pH 9.6) was immobilized to a 96-well plate (manufactured by Nunc) at 4° C. overnight. After that, the 96-well plate was washed with a washing solution (PBS/0.1% TWEEN), 5% FCS/PBS was added, and blocking was performed at 37° C. for 1 hour. After the completion of the blocking, serum diluted 100-fold, 400-fold, 1,600-fold, or 6,400-fold was added, and a reaction was performed at 37° C. for 2 hours. Then, after washing with a washing solution, a peroxidase-conjugated goat anti-human IgG antibody (5,000-fold diluted) (manufactured by Jackson ImmunoResearch) or a peroxidase-conjugated goat anti-human IgA antibody (8,000-fold diluted) (manufactured by Jackson ImmunoResearch) was added, and a reaction was performed at 37° C. for 1 hour. After the completion of the reaction, the resultant was washed with a washing solution, and a substrate solution (solution obtained by dissolving o-phenylenediamine in 0.05 M citrate buffer (pH 5.0)) having added thereto hydrogen peroxide was added for color development. After the color development, 6N sulfuric acid was added to stop the reaction, and absorbances (wavelength: 490 nm) were measured using a microplate reader (manufactured by Bio-Rad). On the basis of those absorbances, antibody titers were calculated by a general method of determining antibody titers (Autoantibodies Against Cancer Antigens: Sacha Gnjatic, Lloyd J. Old, Yao-Tseng Chen). For both IgG and IgA, 100-fold or more with respect to the antibody titer of healthy individual control serum was defined as positive, and less than 100-fold was defined as negative.

<Detection of NY-ESO-1-IgG>

NY-ESO-1 (180 amino acids, SEQ ID NO: 4) was prepared by a general method using *Escherichia coli*. NY-ESO-1-IgG was detected by a method similar to the detection method for XAGE1-IgG described above.

<Detection of Antibody against CT Antigens or p53>

Each CT antigen or p53 was obtained from Okayama University in a state of being immobilized to beads (Bioconjugate Chem. 2015, 26, 2076-2084). Each CT antigen or p53 was detected by a method similar to the detection method for the XAGE1 antibody described above.

Test Example 1

<XAGE1-IgG and XAGE1-IgA Reactions>

Sera collected from 145 advanced (cStageIIIB-IV) lung adenocarcinoma patients were examined for specific IgG and IgA against cancer antigens XAGE1, MAGE-A3, SSX-2, NY-ESO-1, and TP53.

MAGE-A3 was obtained from ATgen (South Korea), SSX-2 was obtained from ATgen (South Korea), and TP53 was obtained from RayBiotech (US). NY-ESO-1 (180 amino acids, SEQ ID NO: 4) was prepared by a general method using *Escherichia coli*. Specific IgG and IgA against each antigen were detected by a method similar to the detection method for XAGE1-IgG and XAGE1-IgA described above.

Figure 2:
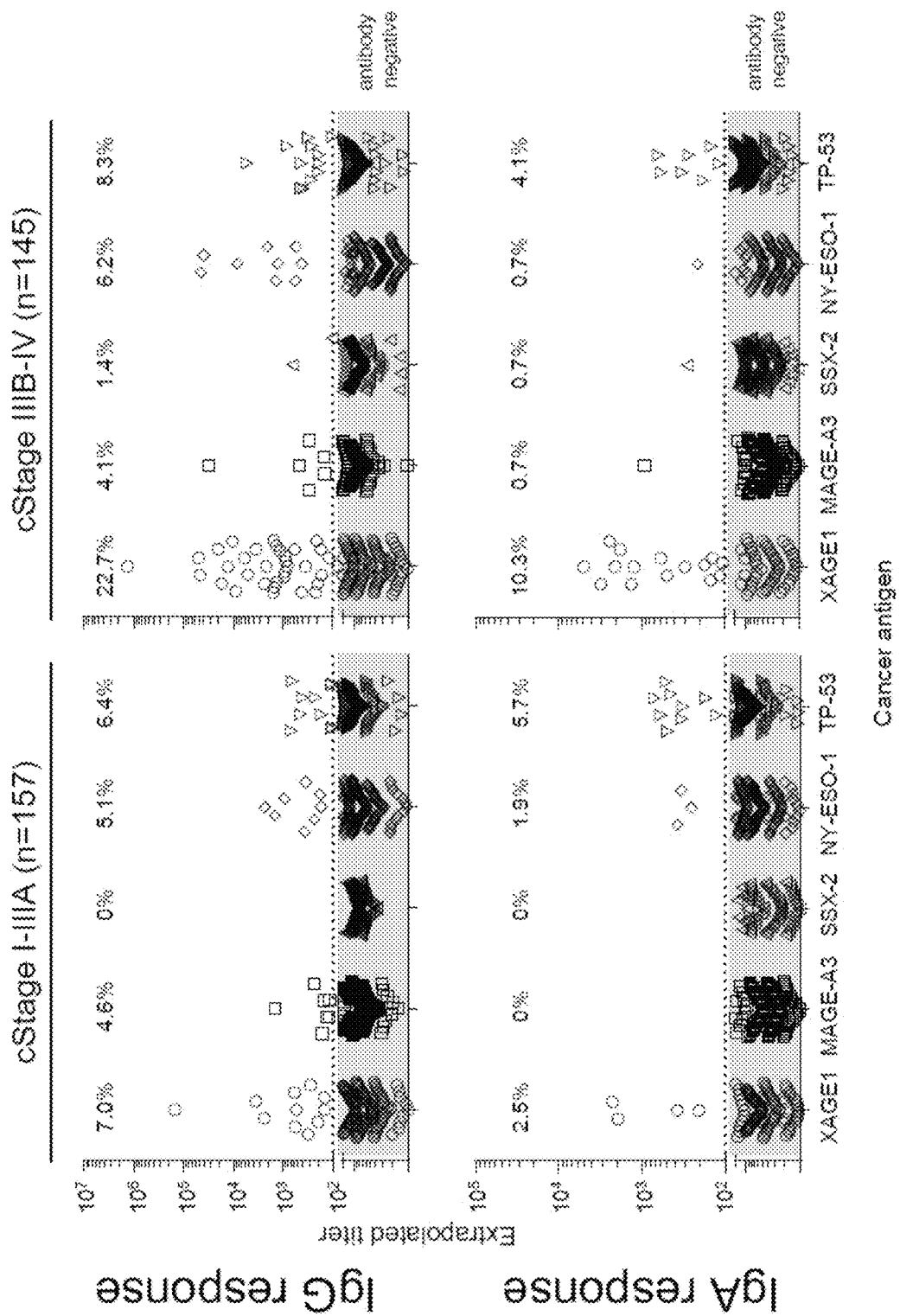
FIG. 2 shows the frequencies of patients positive for specific IgG against cancer-associated antigens XAGE1, MAGE-A3, SSX-2, NY-ESO-1, and TP53 and the frequencies of patients positive for specific IgA there against, which are the results of examination of sera collected from 157 early or locally advanced lung adenocarcinoma (cStage I-IIIA) patients and 145 advanced (cStage IIIB-IV) lung adenocarcinoma patients.

There were 33 XAGE1-IgG-positive individuals (22.7%), and an XAGE1-IgA immune response was confirmed in about a half, 15, of the cases (10.3%) (FIG. 1). This was a much higher frequency than immune responses against the MAGE-A3, SSX-2, NY-ESO-1, and TP53 antigens said to have high immunogenicity in lung cancer (IgG reactions against respective antigens: 4.1%, 1.4%, 6.2%, and 8.3%, IgA reactions: 0.7%, 0.7%, 0.7%, and 4.1%) (FIG. 2). All the XAGE1-IgA-positive patients were XAGE1-IgG-positive.

Test Example 2

<XAGE1-IgG and XAGE1-IgA Reactions as Surrogate Markers>

Sera obtained from 55 XAGE1 antigen-positive lung adenocarcinoma patients were examined for autoantibody reactions against 51 kinds of cancer antigens, and as a result (FIG. 3A), immune responses against various cancer antigens were observed in an XAGE1-IgG-positive and XAGE1-IgA-negative group, revealing that XAGE1-IgG and XAGE1-IgA served as surrogate markers for an immune response against an autologous tumor. Meanwhile, with the appearance of an XAGE1-IgA immune response, the immune response against an autologous tumor was reduced (XAGE1-IgG-positive and XAGE1-IgA-positive group). Further, in XAGE1 immunity-negative cases (XAGE1-IgG-negative and XAGE1-IgA-negative group), the immune response against an autologous tumor was hardly observed.

Figure 3A:
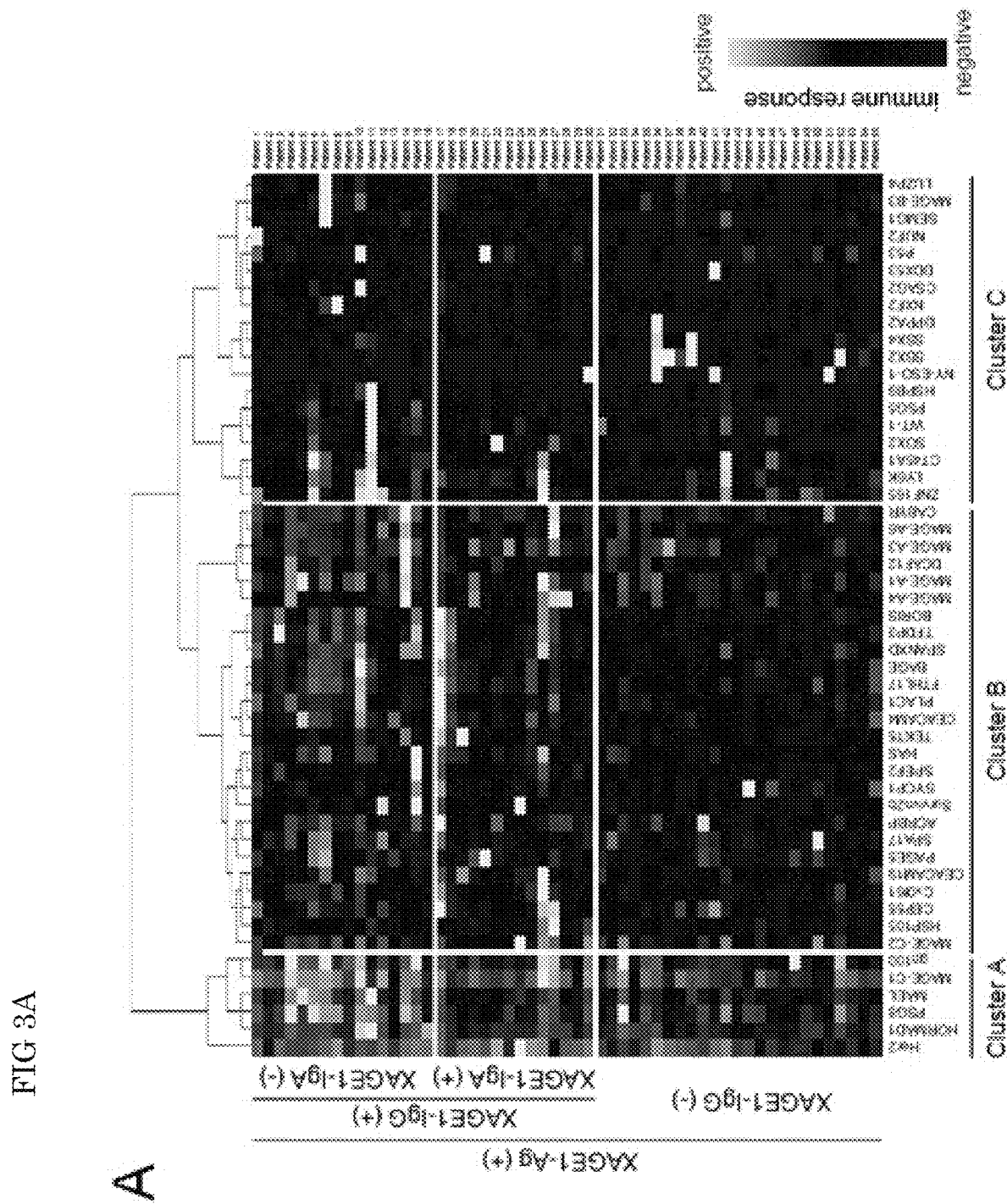
FIG. 3A shows the results of examination of sera obtained from 55 XAGE1 antigen-positive lung adenocarcinoma patients for autoantibody responses against 51 cancer antigens. It is shown that XAGE1-IgG and XAGE1-IgA serve as surrogate markers for an immune response against an autologous tumor. In an XAGE1-IgG-positive and XAGE1-IgA-negative group, immune responses against various cancer antigens are observed. Meanwhile, the appearance of an IgA-type anti-XAGE1 antibody (XAGE1-IgG-positive and XAGE1-IgA-positive group) indicates that the immune response against an autologous tumor is reduced. It is shown that, in XAGE1 immunity-negative patients (XAGE1-IgG-negative and XAGE1-IgA-negative group), the immune responses against autologous tumors is hardly observed.
Figure 3B:
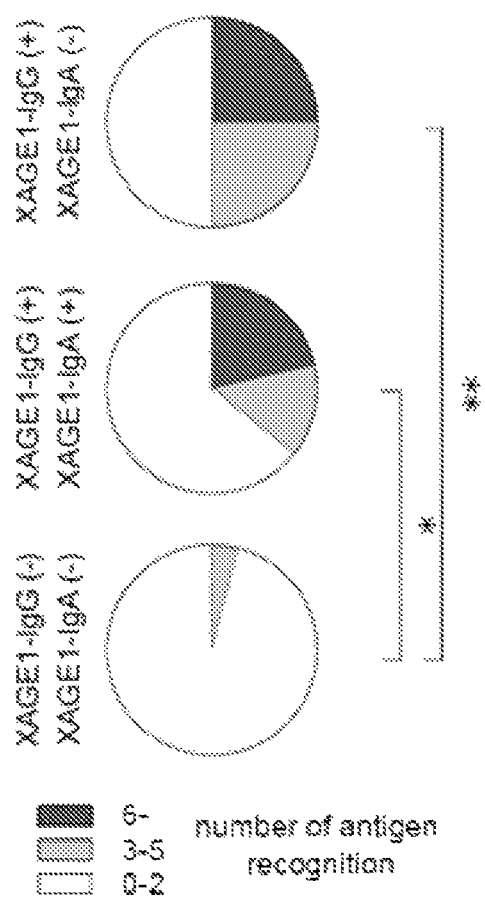
FIG. 3B shows that XAGE1-IgG-positive and XAGE1-IgA-negative patients have immune responses against a plurality of cancer antigens and are in a state of having a potentially high immune response against cancer (immune-activated state), and XAGE1-IgG-positive and XAGE1-IgA-positive patients are in a state of having higher immune activity than XAGE1-IgG-negative and XAGE1-IgA-negative patients, but are in a state of having more suppressed immune activity than XAGE1-IgG-positive and XAGE1-IgA-negative patients.

As shown in FIG. 3B, XAGE1-IgG-positive and XAGE1-IgA-negative individuals have immune reactions against a plurality of cancer antigens and are in a state of having a potentially high immune response against cancer (immune-activated state) as compared to XAGE1-IgG-positive and XAGE1-IgA-positive individuals. Meanwhile, the XAGE1-IgG-positive and XAGE1-IgA-positive individuals are in a state of having higher immune activity than XAGE1-IgG-negative and XAGE1-IgA-negative individuals, but are in a state of having more suppressed immune activity than the XAGE1-IgG-positive and XAGE1-IgA-negative individuals.

Figure 4:
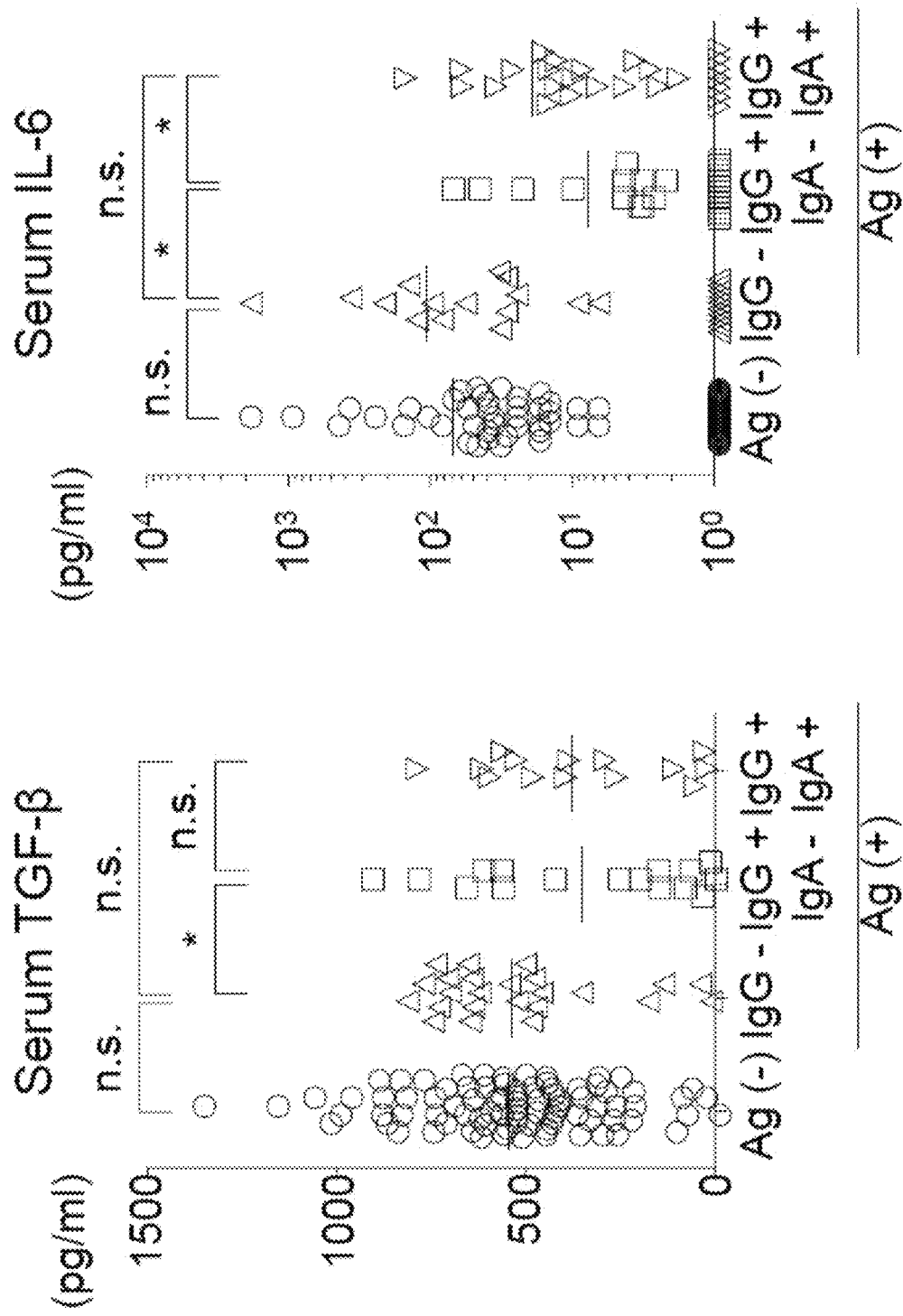
FIG. 4 shows the results of measurement of immunosuppressive cytokines in sera of 145 advanced lung adenocarcinoma patients.

As causes for an immune-activated state and an immunosuppressed state, the properties of a tumor itself are conceivable in the first place. The results of measurement of immunosuppressive cytokines in serum of 145 lung adenocarcinoma patients are shown in FIG. 4. The value for an immunosuppressive cytokine TGF-β was significantly low in XAGE1-IgG-positive and XAGE1-IgA-negative individuals as compared to patients having no XAGE1 immunity, and was comparable in XAGE1-IgG-positive and XAGE1-IgA-positive individuals. Further, the value for IL-6, which is a poor prognostic factor and is a cytokine to be increased at the time of immune exhaustion, is significantly high in the XAGE1-IgG-positive and XAGE1-IgA-positive individuals as compared to the XAGE1-IgG-positive and XAGE1-IgA-negative individuals, suggesting that the XAGE1-IgG-positive and XAGE1-IgA-positive individuals are in an immune exhaustion state as compared to the XAGE1-IgG-positive and XAGE1-IgA-negative individuals.

Figure 5:
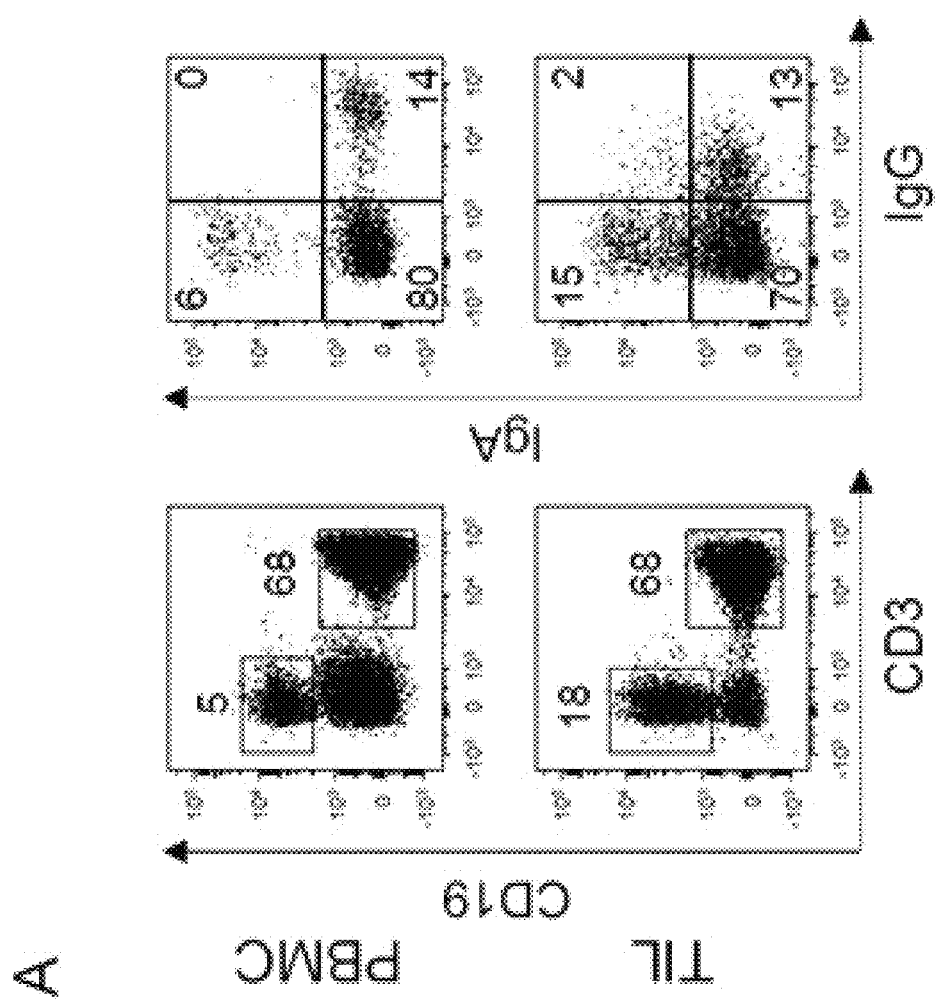
FIG. 5 shows the results of analysis of B-cells and T-cells in tumor site of early or locally advanced lung adenocarcinoma patients.
Figure 5:
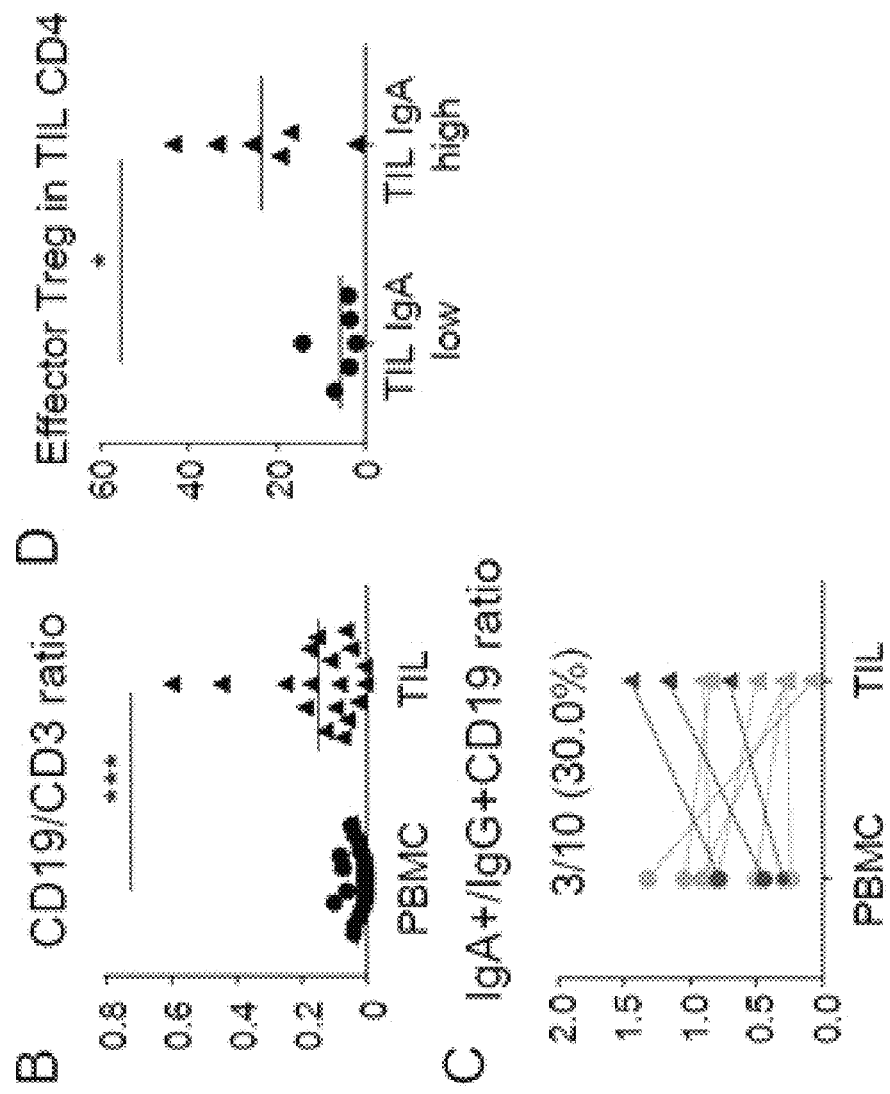
Figure 5:
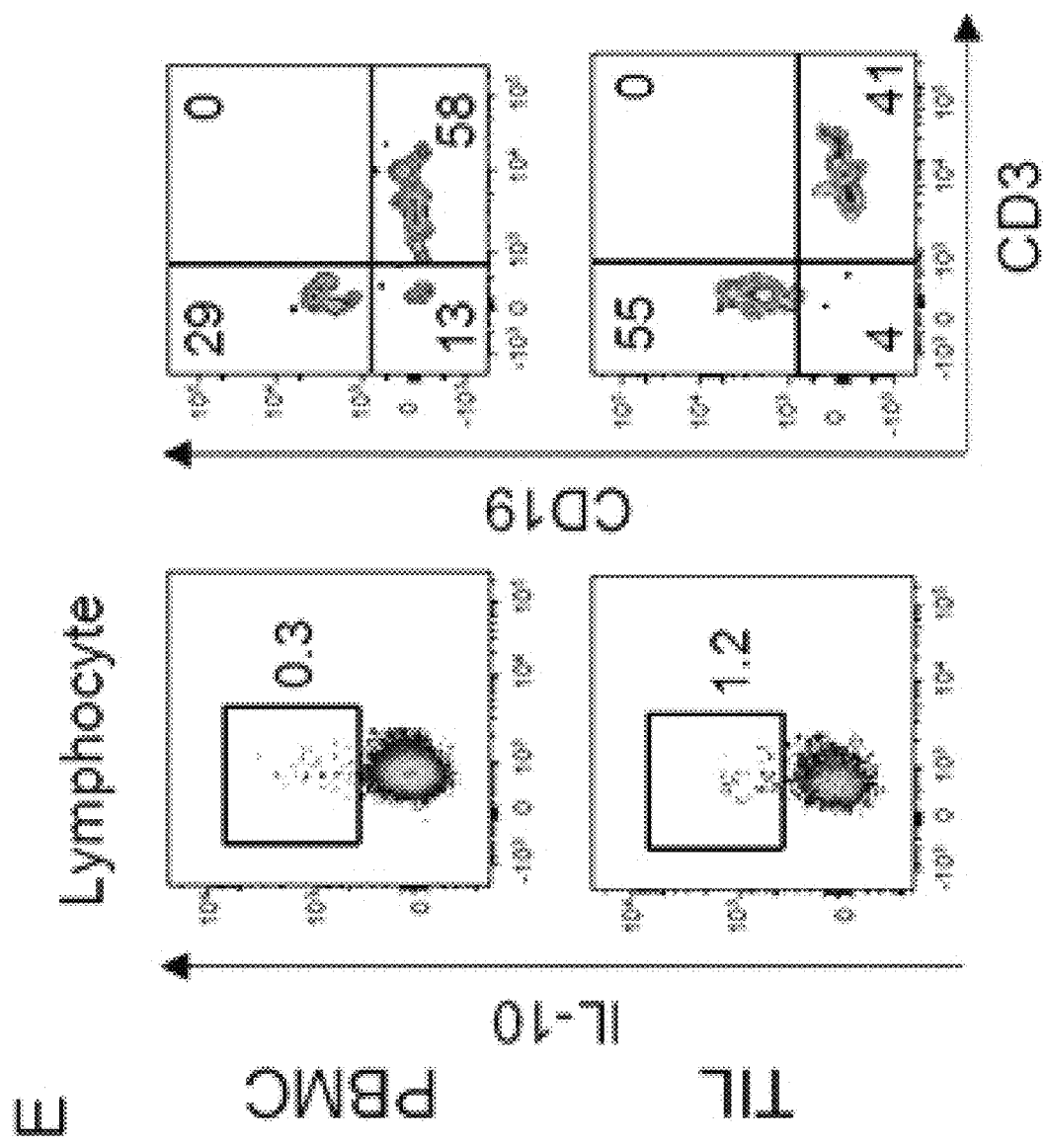
Figure 5:
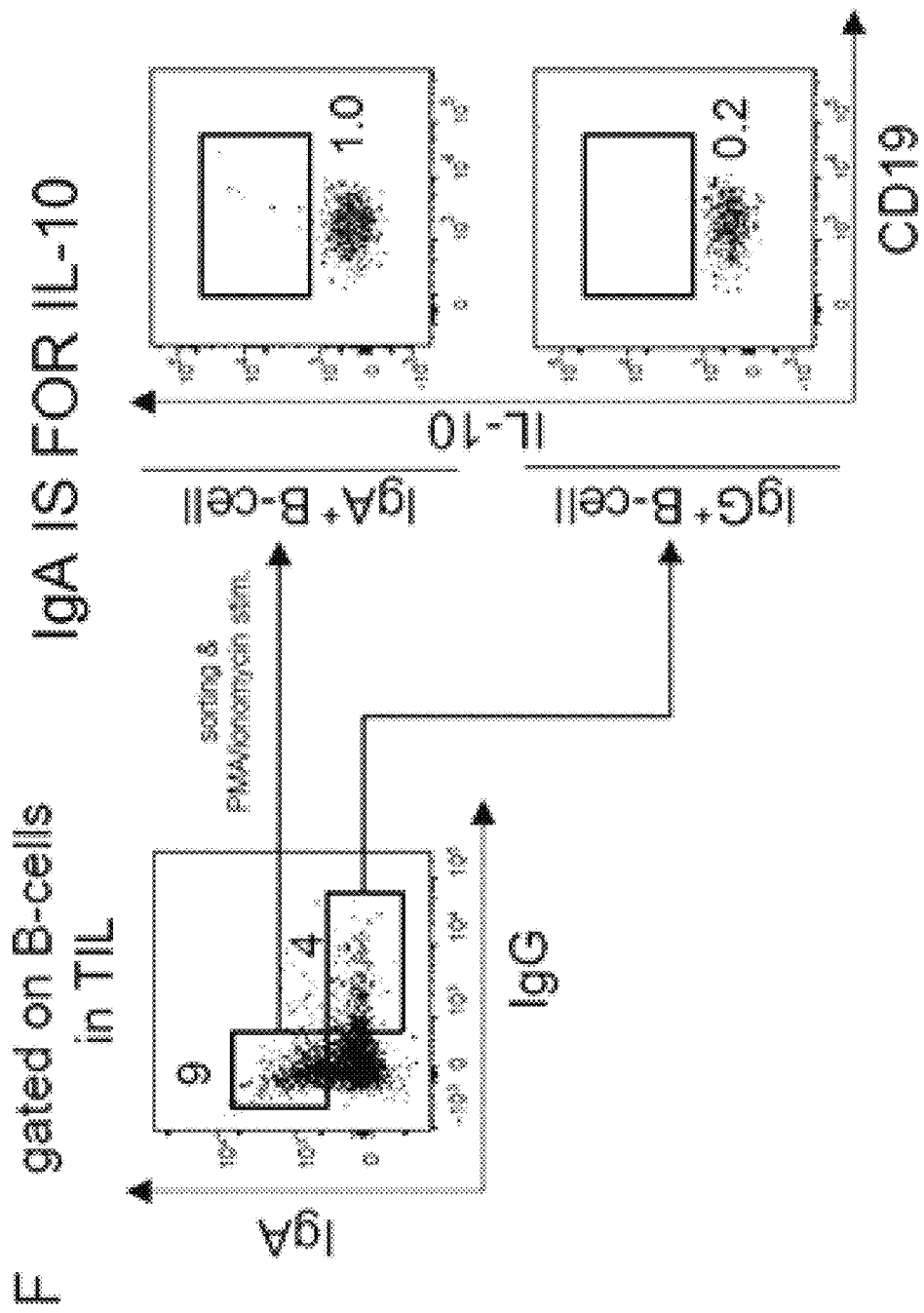
Figure 6:
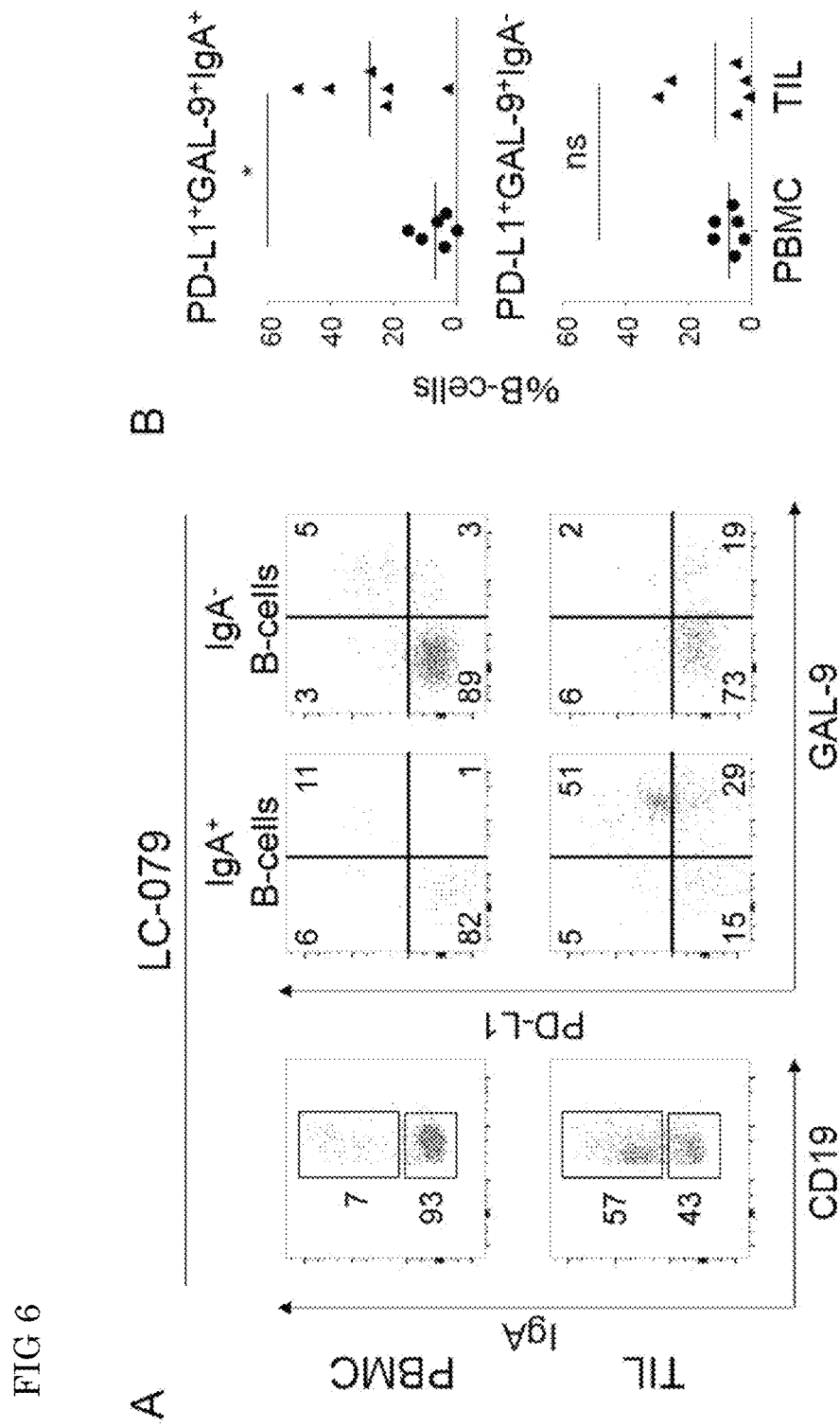
FIG. 6 shows the results of analysis of immune checkpoint molecules expressed in IgA$^+$ B-cells of lung adenocarcinoma patients. It is shown that PD-L1$^+$GAL-9$^+$IgA$^+$ B-cells highly expressing PD-L1 and Galectin-9 are significantly accumulated in tumor site.

Further, in the analysis of a cancer local site (FIG. 5), the frequency of regulatory T-cells, which are cells that suppress immunity in cancer locally, was significantly high inpatients with high local accumulation of IgA$^+$ B-cells (FIG. 5D), showing that such locally accumulated IgA+ B-cells themselves produced the immunosuppressive cytokine IL-10 (FIG. 5F). Thus, it is suggested that IgA+ B-cells are involved in local immunosuppression and the accumulation of regulatory T-cells (local IL-10 is involved in the accumulation). In addition, immune checkpoint molecules expressed in the IgA+ B-cells (molecules suppressing a T-cell function) were analyzed, and as a result, it was found that PD-L1+GAL-9+IgA+ B-cells highly expressing t immune checkpoint molecules PD-L1 and Galectin-9 were significantly accumulated in cancer locally (FIG. 6).

The above-mentioned results suggest that, in XAGE1-IgG+IgA+ patients, immunosuppressive cytokines (e.g., IL-6 and IL-10) are produced owing to, for example, a gene abnormality in a tumor, and IgA+ B-cells suppressing immunity in cancer locally (regulatory B-cells) are accumulated. It is considered that the IgA+ B-cells not only directly suppress the function of T-cells with IL-10 they themselves produce and the immune checkpoint molecules, but also indirectly suppress immunity by locally accumulating the regulatory T-cells.

Test Example 3

<Response Rate and Prognosis Prediction of Chemotherapy by XAGE1 Immunity>

Figure 7:
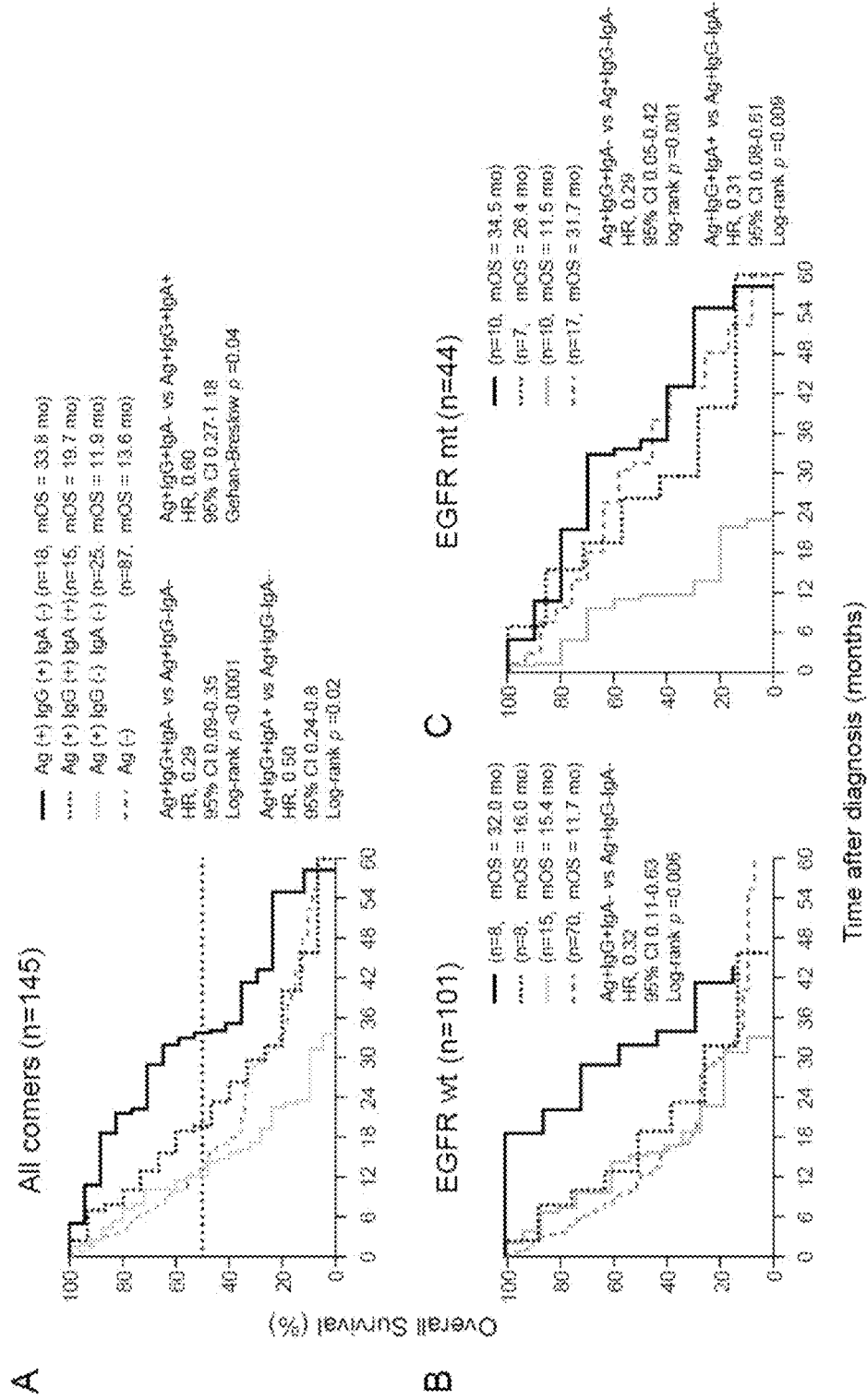
FIG. 7 shows that XAGE1-IgG-positive groups have significantly prolonged median survival times, and that this tendency is remarkable in EGFR gene mutation-negative patients.

In the investigation of 145 cases of advanced lung adenocarcinoma, survival curves were analyzed using XAGE1-IgG, XAGE1-IgA, the absence of any immune response, and the absence of XAGE1 expression as indicators. The results were as follows: an XAGE1-IgG-positive and XAGE1-IgA-negative group had a median survival time of 33.8 months, an XAGE1-IgG-positive and XAGE1-IgA-positive group had a median survival time of 19.7 months, a group without any immune response (XAGE1-IgG-negative and XAGE1-IgA-negative group) had a median survival time of 11.9 months, and a group without XAGE1 expression had a median survival time of 13.6 months, revealing that the XAGE1-IgG-positive groups had significantly prolonged median survival times. In particular, the prolongation of the median survival time was remarkable in the XAGE1-IgG-positive and XAGE1-IgA-negative group (FIG. 7).

Such tendency was remarkable in EGFR gene mutation-negative cases. In the investigation of 101 cases of EGFR gene mutation-negative advanced lung adenocarcinoma, an XAGE1-IgG-positive and XAGE1-IgA-negative group had a median survival time of 32.0 months, an XAGE1-IgG-positive and XAGE1-IgA-positive group had a median survival time of 16.0 months, a group without any immune response (XAGE1-IgG-negative and XAGE1-IgA-negative group) had a median survival time of 15.4 months, and a group without XAGE1 expression had a median survival time of 11.7 months (FIG. 7).

Figure 8:
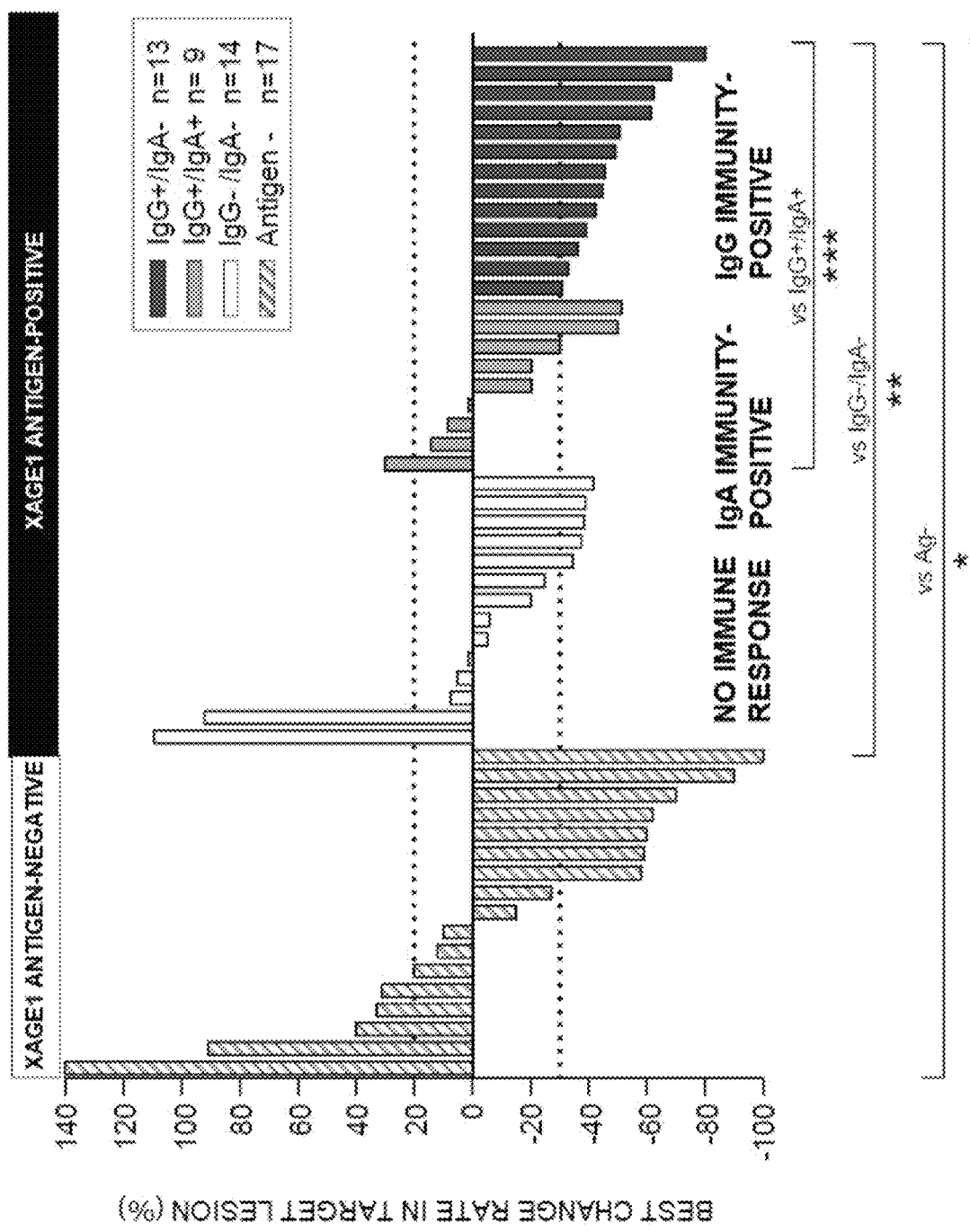
FIG. 8 shows that an XAGE1-IgG-positive and XAGE1-IgA-negative group has a significantly high response rate to initial chemotherapy as compared to an XAGE1-IgG-positive and XAGE1-IgA-positive group and a group without any immune response.

Further, it was revealed that, among 36 advanced lung adenocarcinoma patients who were EGFR gene mutation-negative and measurable for an XAGE1 antigen-expressing lesion, an XAGE1-IgG-positive and XAGE1-IgA-negative group had a significantly high response rate to initial chemotherapy as compared to an XAGE1-IgG-positive and XAGE1-IgA-positive group and a group without any immune response (FIG. 8).

Thus, it was revealed that the response rate and prognosis of chemotherapy were able to be clearly predicted by using immune responses against XAGE1 (XAGE1-IgG, XAGE1-IgA, and the absence of any immune response) as indicators.

Test Example 4

<XAGE1 and NY-ESO-1 Immunity as Biomarkers for Responder Case to Immune Checkpoint Molecule Inhibitor Drug>

The effect of anti-PD-1 antibody therapy serving as immune checkpoint inhibitors was investigated with 53 advanced non-small-cell lung cancer patients using immune responses against highly immunogenic XAGE1 and NY-ESO-1 (presence of an immune response against XAGE1 or NY-ESO-1, and the absence of any immune response) as indicators. Sera of patients were collected about 28 days before anti-PD-1 antibody therapy.

Figure 9:
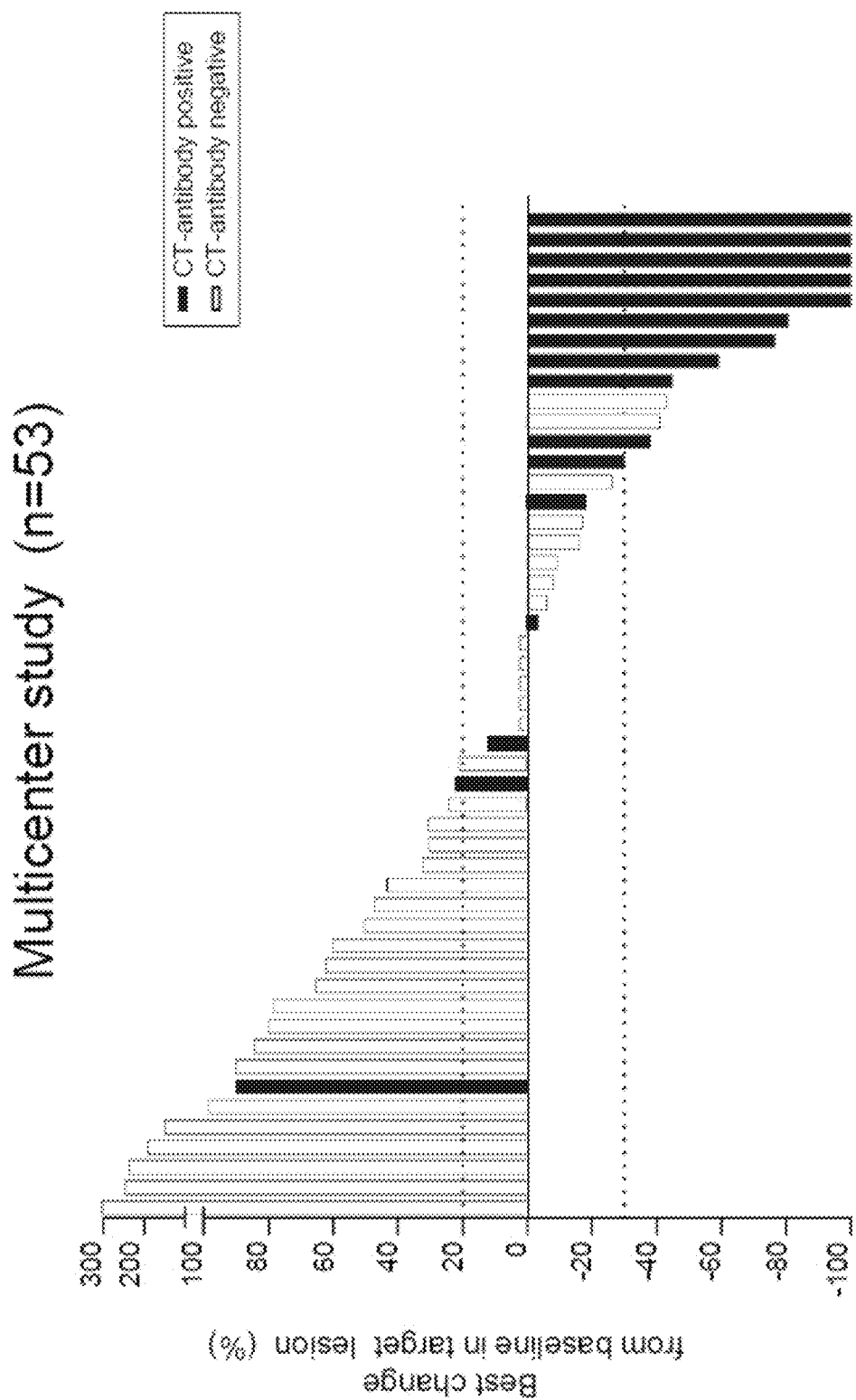
FIG. 9 shows that immune responses against XAGE1 and NY-ESO-1 are useful biomarkers predicting effect of anti-PD-1 antibody therapy of immune checkpoint inhibitors. Best change rates in target lesions in a group with an immune response against XAGE1 or NY-ESO-1 (XAGE1-IgG-positive or NY-ESO-1-IgG-positive group) and a group without any immune response (group without antibodies against XAGE1 and NY-ESO-1) are shown.
Figure 10:
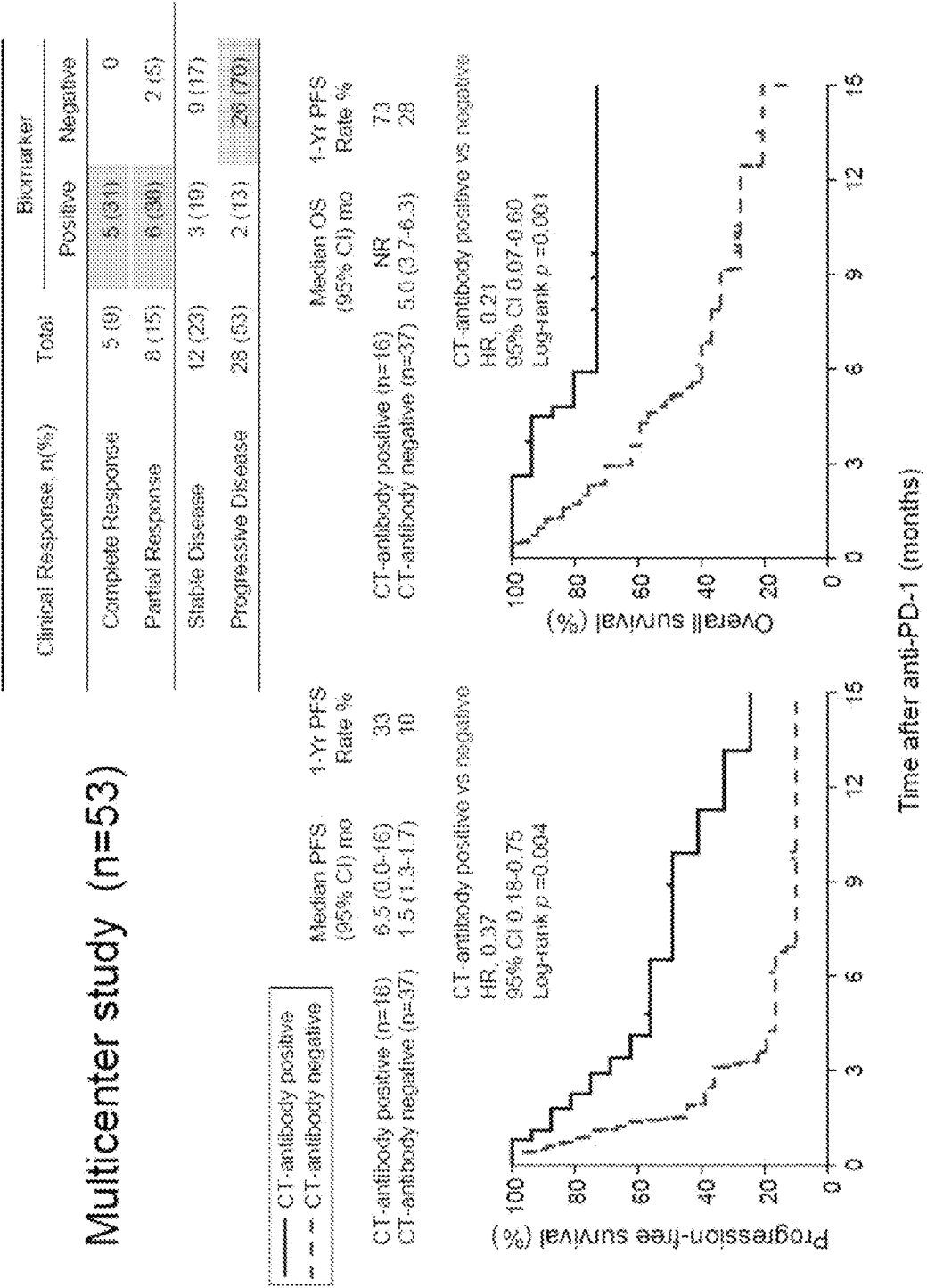
FIG. 10 shows response rates, progression-free survivals, and overall survivals after anti-PD-1 antibody therapy of immune checkpoint inhibitors in a group with an immune response against XAGE1 or NY-ESO-1 (XAGE1-IgG-positive or NY-ESO-1-IgG-positive group) and a group without any immune response (group without antibodies against XAGE1 and NY-ESO-1).

Group with an immune response against XAGE1 (XAGE1-IgG-positive) or with an immune response against NY-ESO-1 (NY-ESO-1-IgG-positive): 16 patients Group without any immune response (group without antibodies against XAGE1 and NY-ESO-1): 37 patients In FIG. 9, best change rates in target lesions are shown. In the group with an immune response against XAGE1 or NY-ESO-1, a marked tumor regression effect in the target lesion was found in most patients, but in the group without any immune response, no marked tumor regression effect was found. Response rates are shown in FIG. 10. In the group with an immune response against XAGE1 or NY-ESO-1, there were 5 complete response (CR), 6 partial response (PR), 3 stable disease (SD), and 2 progressive disease (PD). In the group without any immune response, there were 2 PR, 9 SD, and 26 PD. In addition, progression-free survivals and overall survivals in group with immune response against XAGE1 or NY-ESO-1 and group without any immune response are shown in FIG. 10. It was revealed that there were remarkable differences in progression-free survival and overall survival between group with an immune response and without any immune response.

Test Example 5

Under current guidelines, on the ground that immune checkpoint inhibitors have low immunotherapeutic effects on lung cancer with driver gene mutations, such as EGFR gene mutation or EML-4/ALK fusion gene abnormality, a notification has been issued that application of immunotherapy should be decided with careful consideration (should be avoided). However, as a result of immunotherapy (therapy with an anti-PD-1 antibody serving as an immune checkpoint inhibitors) performed for two XAGE1-IgG-positive and XAGE1-IgA-negative patients, one of whom had EGFR gene mutation, and the other of whom had EML-4/ALK fusion gene abnormality, the one with EGFR gene mutation was SD, and one with EML-4/ALK fusion gene abnormality had a marked response with 90% or more tumor regression. Marked response patients to immunotherapy (therapy with an anti-PD-1 antibody serving as an immune checkpoint inhibitors) to be overlooked under current guidelines can be treated without being overlooked by using XAGE1-IgG and XAGE1-IgA as indicators.

As apparent from the foregoing, the presence or absence of XAGE-IgG and XAGE-IgA is involved in the prognoses of chemotherapy and immunotherapy, and it is suitable that IgG and IgA be examined as a set.

Figure 11:
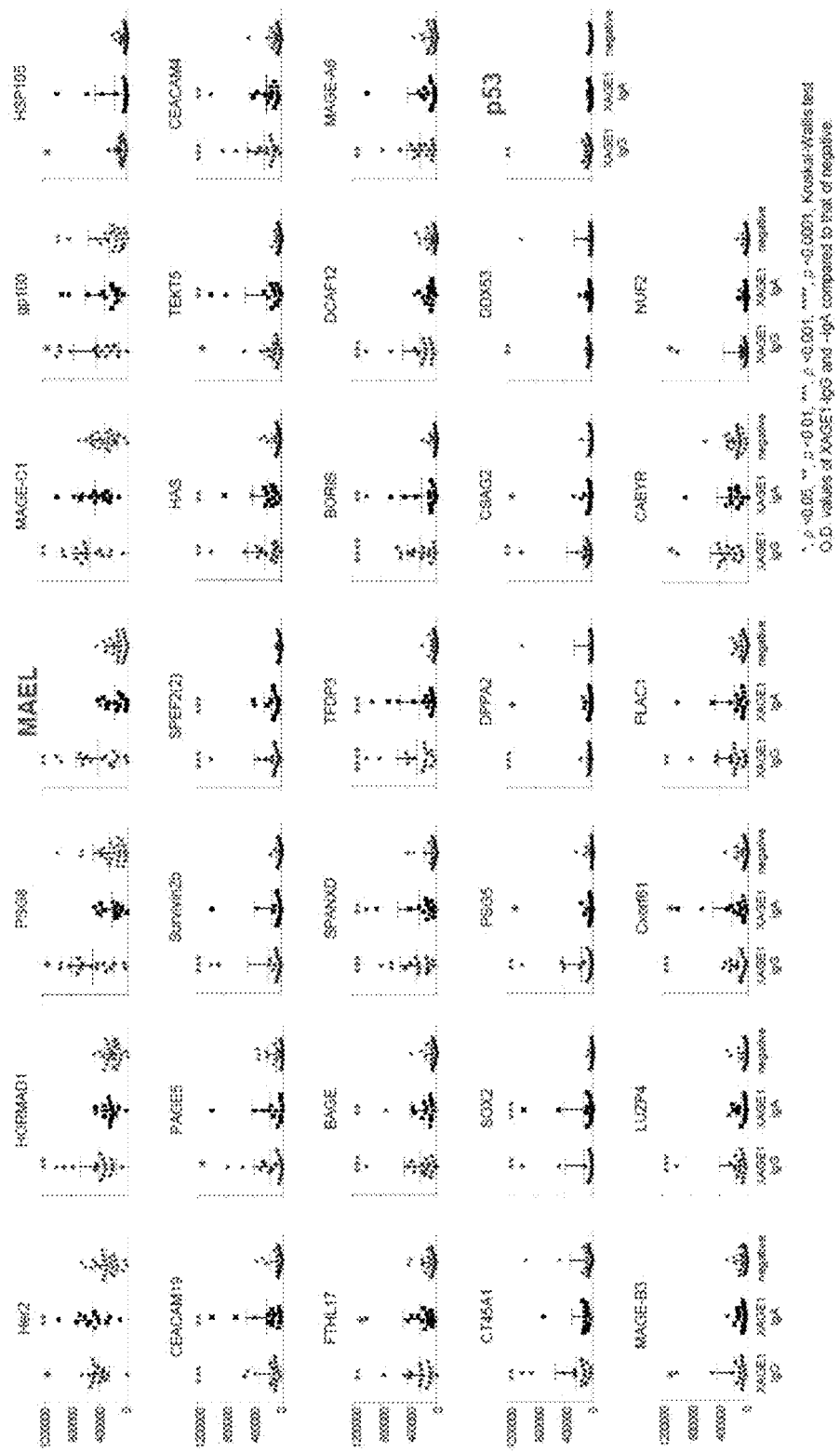
FIG. 11 shows the results of further analysis of the results shown in FIG. 3A for immune responses against cancer antigens in the XAGE1-IgG-positive and XAGE1-IgA-negative group, the XAGE1-IgG-positive and XAGE1-IgA-positive group, and the XAGE1-IgG-negative and XAGE1-IgA-negative group.

In FIG. 11, the results of further analysis of the results shown in FIG. 3A for immune reactions against the cancer antigens in the XAGE1-IgG-positive and XAGE1-IgA-negative group, the XAGE1-IgG-positive and XAGE1-IgA-positive group, and the XAGE1-IgG-negative and XAGE1-IgA-negative group are shown. As shown in FIG. 11, the immune reactions against the MAEL antigen and p53 antigen are specifically found in XAGE1-IgG-positive and XAGE1-IgA-negative individuals. Therefore, anti-MAEL antibody-positive individuals and anti-p53 antibody-positive individuals are XAGE1-IgG-positive and XAGE1-IgA-negative, and are in immune-activated state.

Figure 12:
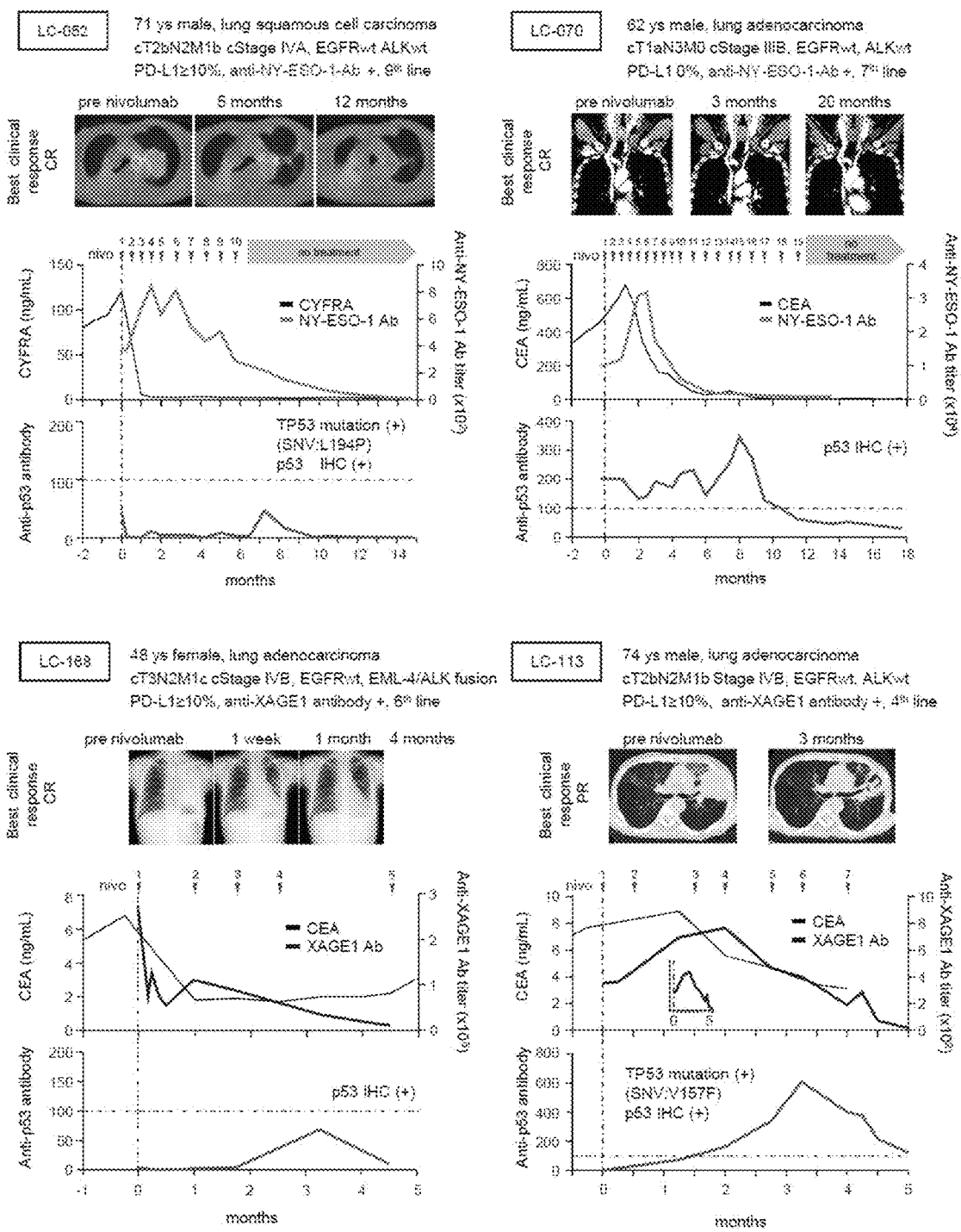
FIG. 12 shows the results of monitoring of anti-NY-ESO-1 antibody, anti-XAGE1 antibody, and anti-p53 antibody in responders to anti-PD-1 antibody therapy.

In addition, the immune response against the anti-p53 antibody predicts effect of chemotherapy and immunotherapy. In FIG. 12, anti-NY-ESO-1 antibody, anti-XAGE1 antibody, and anti-p53 antibody were monitored in responder patients to anti-PD-1 antibody therapy. As a result, enhanced immune responses against p53 antigen were found in responder patients, and hence change of anti-p53 antibody is useful for judging effect of anti-PD-1 antibody therapy.

<Anti-NY-ESO-1 Antibody, Anti-BAGE Antibody, and Anti-BORIS Antibody>

Figure 13A:
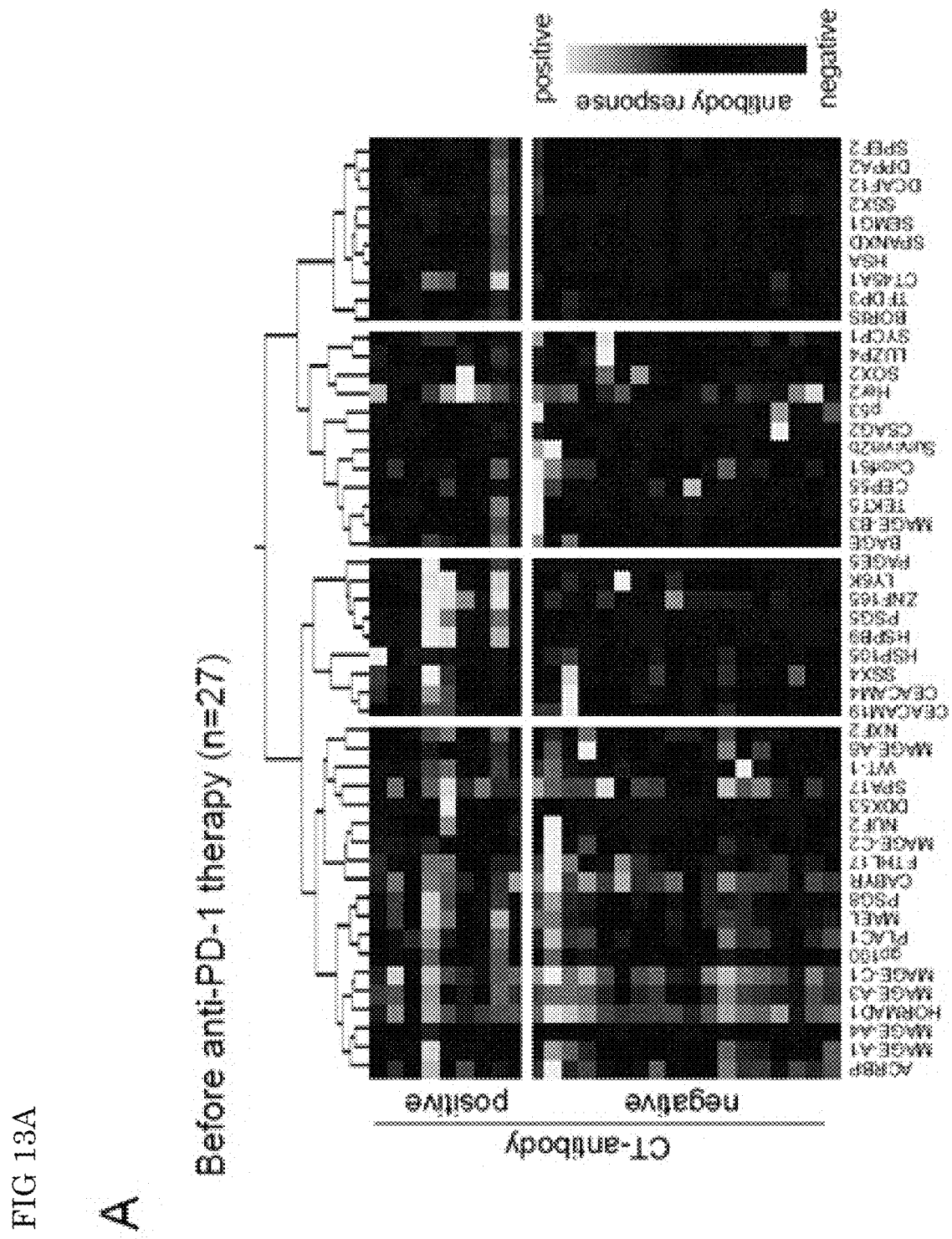
FIG. 13A shows the results of analysis of immune responses against 50 cancer antigens including XAGE1 and NY-ESO-1 antibodies using pre-treatment sera of patients subjected to anti-PD-1 antibody therapy. It is shown that XAGE1-IgG-positive or NY-ESO-1-IgG-positive patients have immune responses against multiple antigens and are in an immune-activated state.
Figure 13B:
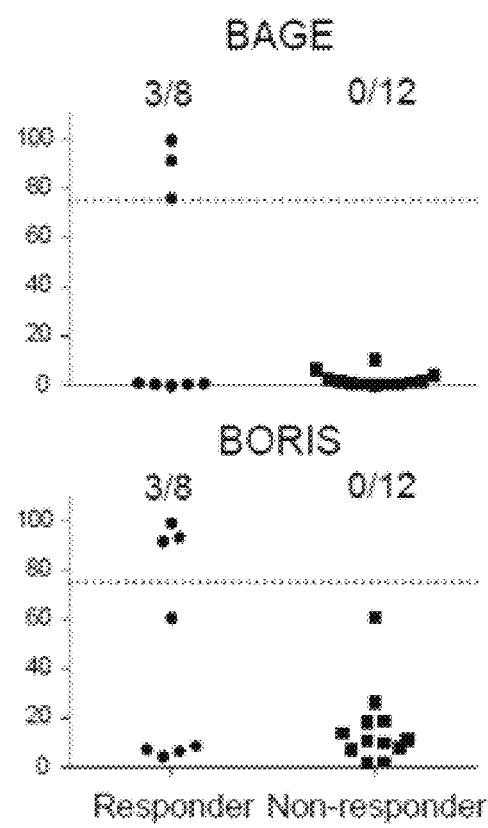
FIG. 13B shows that effect of the anti-PD-1 therapy can be predicted by detecting anti-BADE or an anti-BORIS antibody before anti-PD-1 antibody therapy.

Pre-treatment sera of patients subjected to anti-PD-1 antibody therapy were used to analyze immune responses against 50 cancer antigens including XAGE1 and NY-ESO-1 antibodies. As shown in FIG. 13A, XAGE1-IgG- and NY-ESO-1-IgG-positive individuals have immune responses against multiple antigens and are in an immune-activated state. In addition, as shown in FIG. 13B, three out of eight responder cases to anti-PD-1 antibodies are significantly positive for an immune reaction against BAGE antigen or BORIS antigen (zero out of twelve non-responder cases), and hence effect of anti-PD-1 therapy can be predicted by detection of anti-BAGE antibody or anti-BORIS antibody.

<Antigen Spreading>

Figure 14:
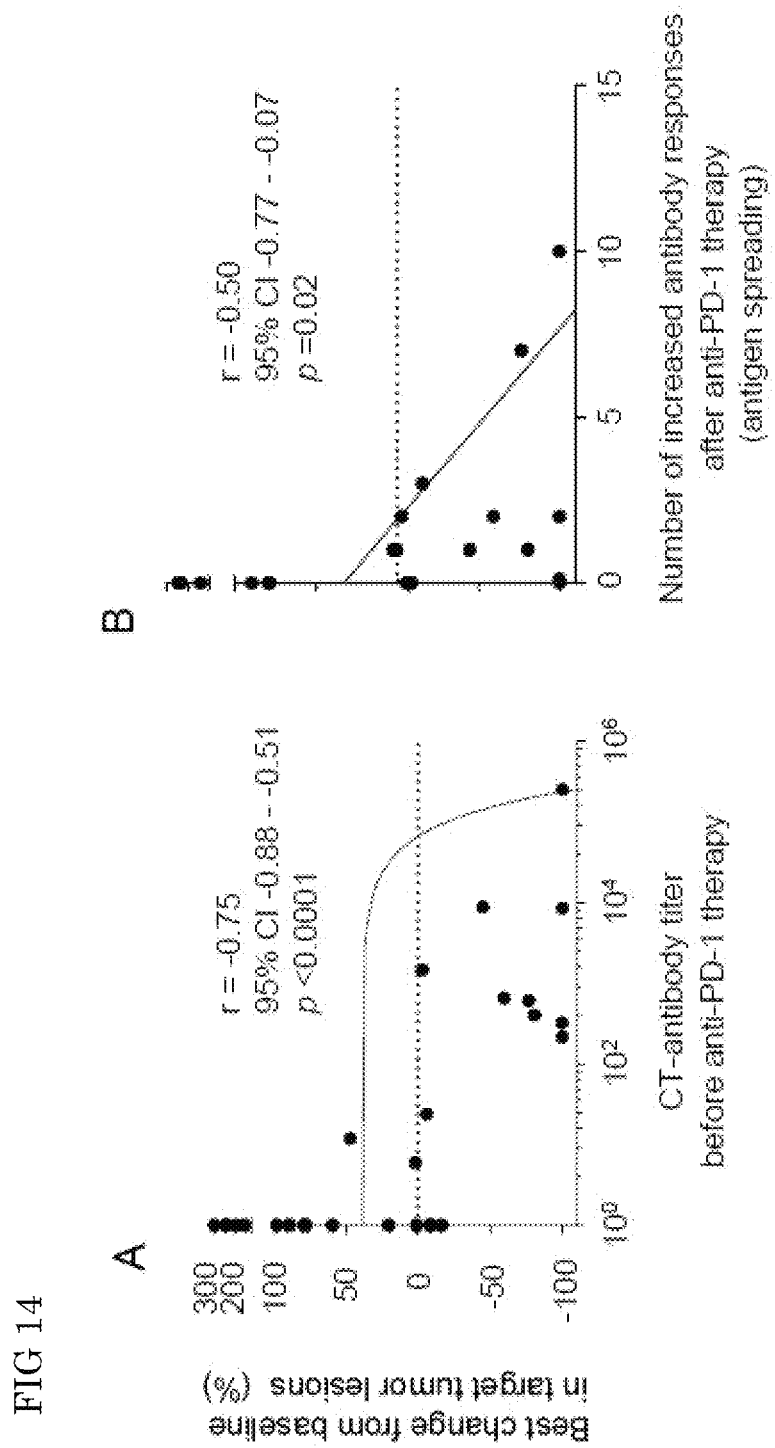
FIG. 14A a relationship between a change rate in a target lesion through anti-PD-1 antibody therapy (a negative value means tumor regression) and the antibody titer of antibodies against CT antigens (XAGE1-IgG and NY-ESO-1-IgG).
FIG. 14B a relationship between the change rate in the target lesion through anti-PD-1 antibody therapy and the number of enhanced immune responses against multiple antigens after anti-PD-1 antibody therapy (antigen spreading).

In FIG. 14A, a relationship between a change rate in a target lesion through anti-PD-1 antibody therapy (a negative value means tumor regression) and antibody titer of antibodies against CT antigens (XAGE1-IgG and NY-ESO-1-IgG) is shown. In FIG. 14B, a relationship between the change rate in the target lesion through anti-PD-1 antibody therapy and the number of enhanced immune responses against multiple antigens after treatment (antigen spreading) is shown. It was revealed that: as antibody titer against CT antigens increased, tumor regression rate of anti-PD-1 therapy became higher; and as the number of immune responses against various CT antigens increased (antigen spreading increased), the tumor regression rate of anti-PD-1 therapy became higher. Accordingly, effect of anti-PD-1 therapy can be predicted by detecting antibodies against a plurality of CT antigens.

<Anti-MAGE-B3 Antibody and Anti-SSX4 Antibody>

Figure 15A:
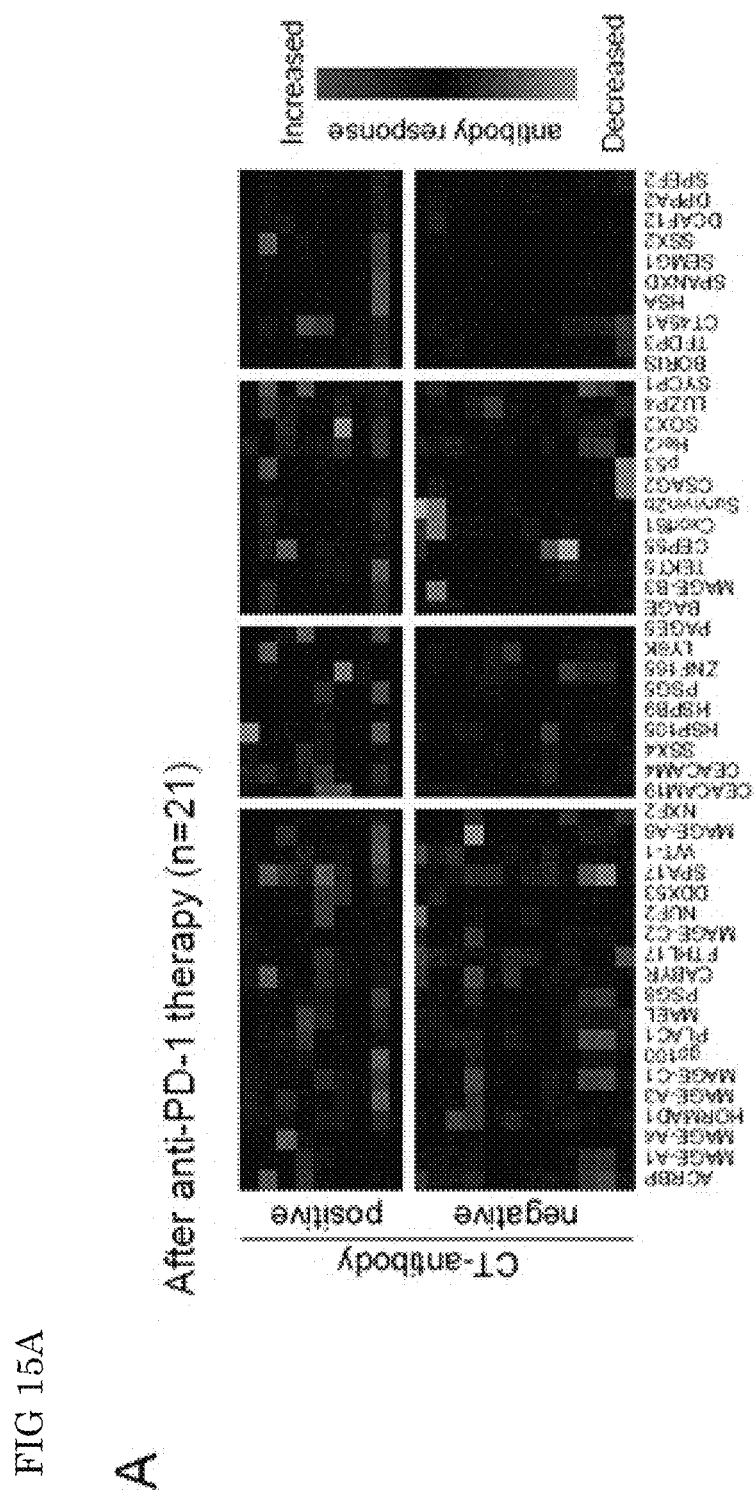
FIG. 15A shows differences between immune responses against multiple antigens before and after anti-PD-1 antibody therapy.

In FIG. 15A, differences between immune responses against multiple antigens before and after anti-PD-1 antibody therapy are shown. In FIG. 15B, it is shown that the spreading of immune responses against MAGE-B3 and SSX4 antigen was found at a high frequency in responder patients to anti-PD-1 antibody therapy, and was not found in non-responder patients. Accordingly, anti-MAGE-B3 antibody and anti-SSX4 antibody are factors actually having significant influences on effect of anti-PD-1 antibody therapy, and are useful for prediction of effect.

Figure 16:
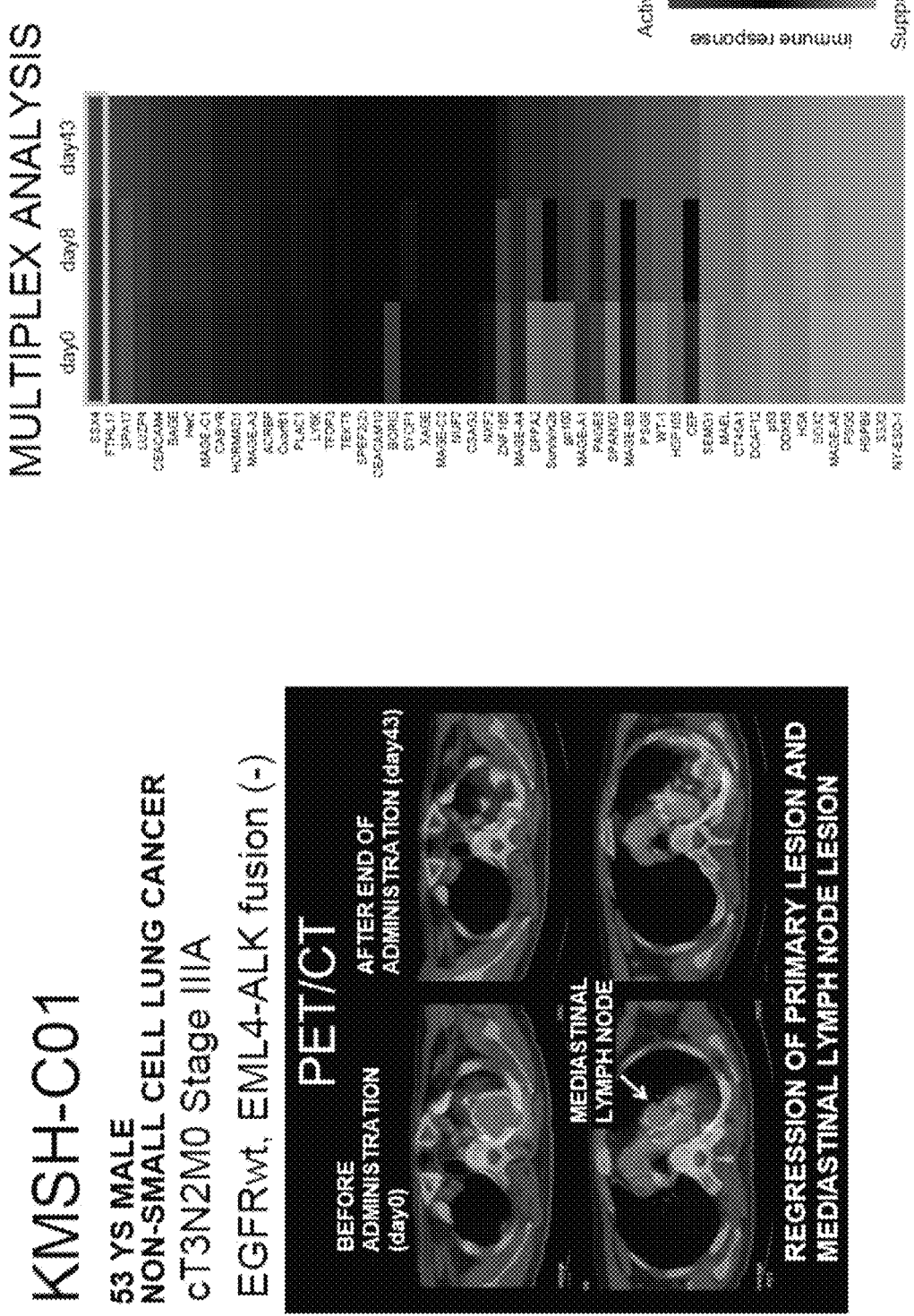
FIG. 16 shows that immune response against SSX4 antigen was actually observed in a complete responder in an investigator-initiated study with preoperative combined use of an anti-CCR4 antibody+an anti-PD-1 antibody.
Figure 17:
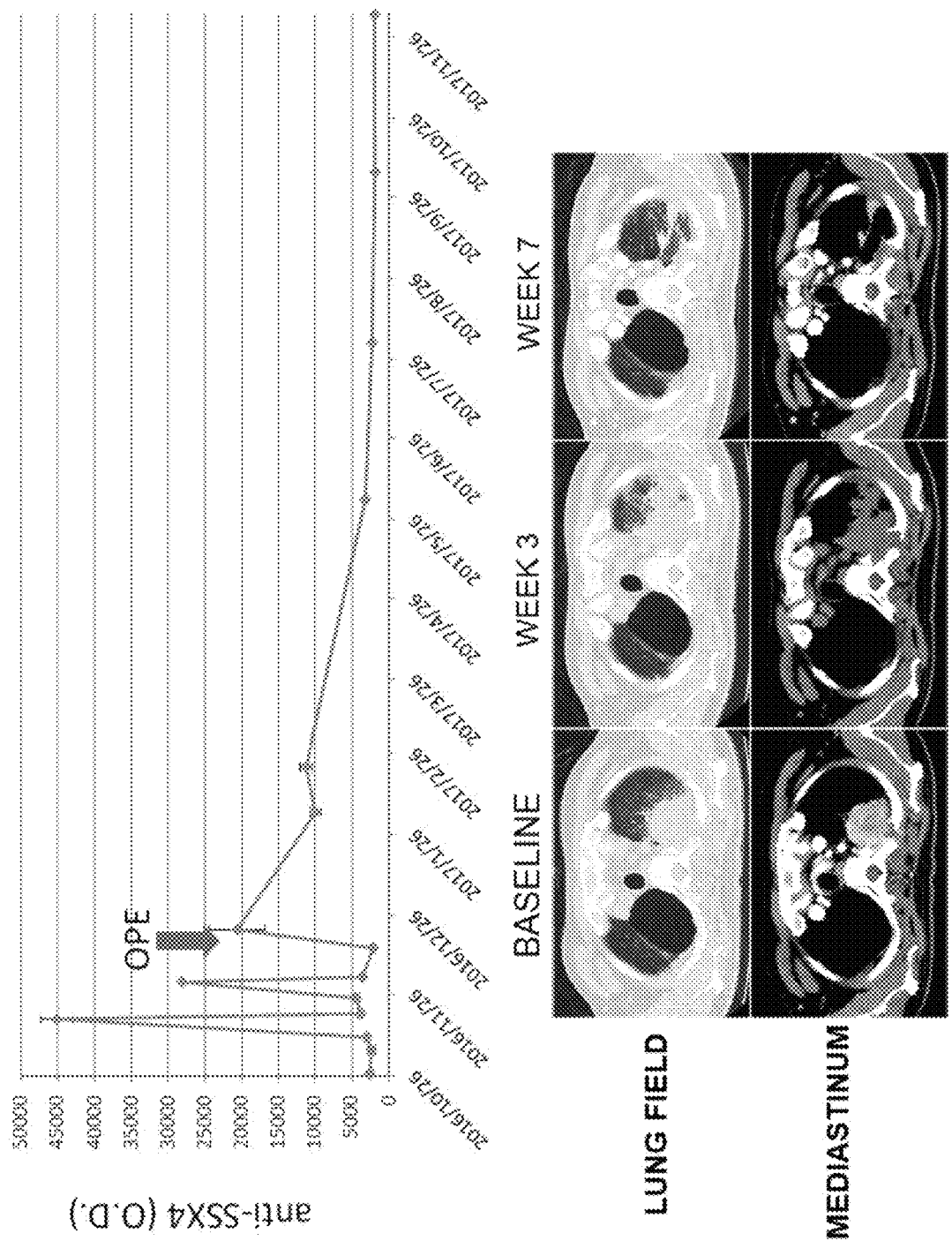
FIG. 17 shows that course of tumor regression and immune responses against SSX4 correlated with each other.
Figure 18A:
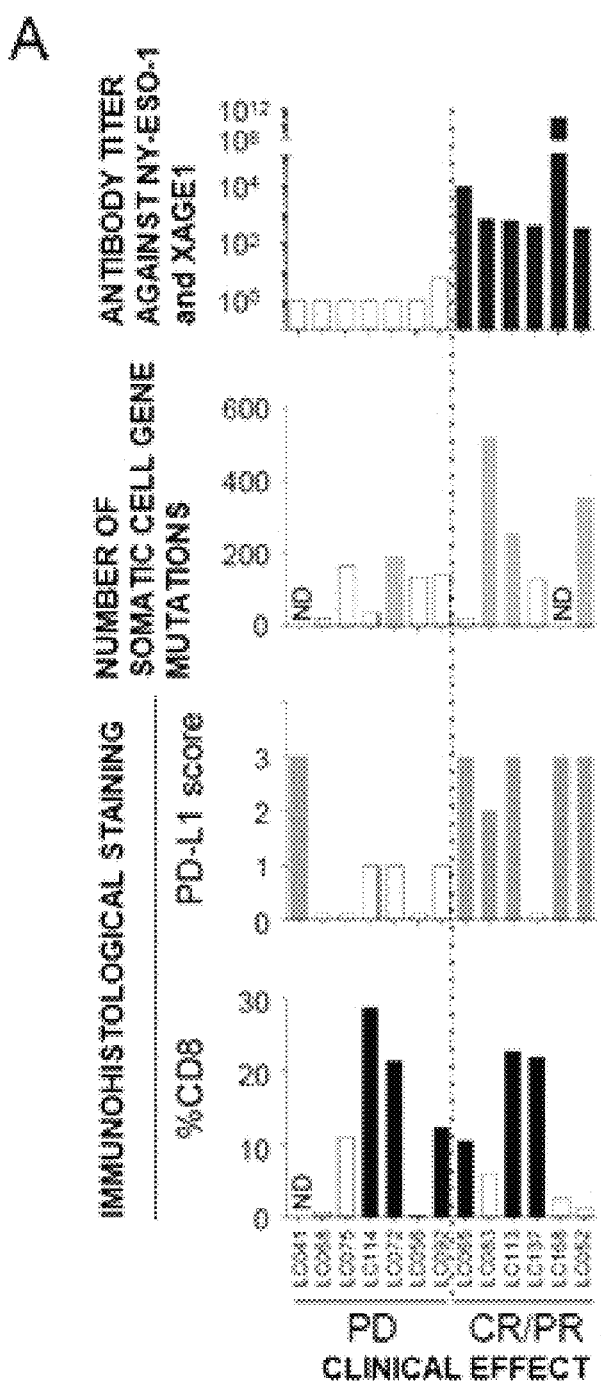
FIG. 18 shows that positivity for antibodies against CT antigens (anti-XAGE1 antibody and anti-NY-ESO-1 antibody) can more accurately predict the effect of anti-PD-1 antibody therapy than known biomarkers.
Figure 18B:
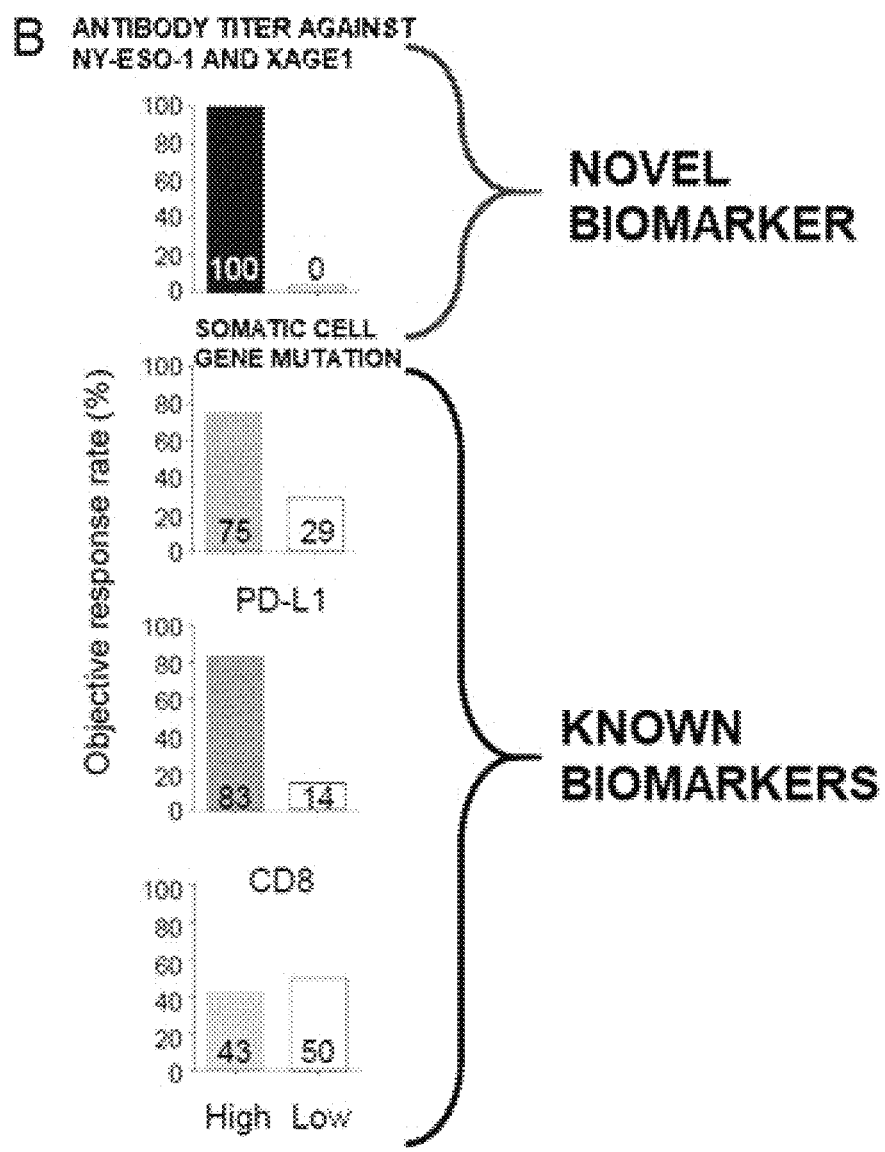

In FIG. 16 and FIG. 17, images and immune responses of the same patient, who is a complete responder in an investigator-initiated study with preoperative combined use of an anti-CCR4 antibody+an anti-PD-1 antibody, are shown. In FIG. 16, it is shown that immune response against SSX4 antigen was observed. The images of FIG. 17 are chest CT images, the "BASELINE" images are CT images before anti-CCR4 antibody plus anti-PD-1 antibody administration, and "WEEK 3" and "WEEK 7" are CT images after investigational drug administration and preoperative. Anti-CCR4 antibody was administered four times preoperatively, anti-PD-1 antibody was administered three times preoperatively, and operation was performed in week 8. The CT images indicate that the tumor regressed through immunotherapy. This patient is anti-SSX4 antibody-positive, and is a patient with a marked response to immunotherapy. As can be seen, the measurement of anti-SSX4 antibody is useful as a method of predicting effect of immunotherapy.

Example 2

<Synthesis of XAGE1 Long-chain Peptides and Production of Composition (Vaccine) for Inducing Immune Response>

Long-chain peptides SLP1 and SLP2 each having 25 amino acid residues, which were partial peptides of XAGE1, were synthesized by a general method at Peptide Institute, Inc. in GMP grade. SLP1 is a peptide formed of amino acids 8 to 32 of XAGE1 (protein formed of 81 amino acids), and SLP2 is a peptide formed of amino acids 44 to 68 thereof. The purity of each of SLP1 and SLP2 was confirmed to be 99% or more.

```
SLP1 amino acid sequence
(SEQ ID NO: 1):
NQQLKVGILHLGSRQKKIRIQLRSQ

SLP2 amino acid sequence
(SEQ ID NO: 2):
ISQTPGINLDLGSGVKVKIIPKEEH
```

SLP1 and SLP2 obtained above were mixed to provide a composition (vaccine) for inducing an immune response.

<Stimulation of Cells with SLP1 and SLP2> a. Separation of Cells

Mononuclear cells were obtained from peripheral blood of XAGE1 antibody-positive patients (XAGE1-IgG-positive and XAGE1-IgA-negative patients) by a density gradient centrifugation method. Then, with the use of anti-CD4 antibody-bound beads and anti-CD8 antibody-bound beads (manufactured by Miltenyi Biotec), CD8-positive cells, CD4-positive cells, and CD4-negative and CD8-negative cells were sequentially separated by a magnetic-activated cell sorting method (MACS, manufactured by Miltenyi Biotec).

b. Establishment of SLP1- or SLP2-Specific CD4-Positive T Cell Clone b1. $1\times10^6$ CD4-positive T-cells and $1\times10^6$ CD4-negative and CD8-negative cells that had been irradiated with a radiation of 40 Gy were subjected to stimulated culture in 200 μl of a 2% serum-containing AIM culture medium (containing IL-2 and IL-7) in a 96-well U-bottom culture plate in the presence of 1 μM each of SLP1 and SLP2 for 14 days.

Also in culture in the following experiments, 200 μl of the 2% serum-containing AIM culture medium (containing IL-2 and IL-7) was used unless otherwise specified.

b2. For use as antigen-presenting cells, part of the CD4-positive T-cells of the patients obtained in the section "a" were stimulated with PHA to prepare T-APC cells.

b3. 30 μl of the cells collected from the 96-well plate after the stimulated culture for 14 days in the section b1 were placed in a fresh 96-well plate for each of restimulation with SLP1 and SLP2 and non-stimulation, and $1\times10^4$ (30 μl) of the T-APCs prepared as antigen-presenting cells were added to each well. Further, SLP1 and SLP2 were each added at 1

μM to the wells for restimulation with SLP1 and SLP2, and restimulation was performed for 12 hours.

b4. After 12 hours, IFNγ in culture supernatants in the 96 wells was detected by an ELISA method.

b5. The IFNγ activities of the culture supernatants stimulated with SLP1 and SLP2 and the unstimulated culture supernatants were compared, and wells with potent activities, in which antigen-specific T-cells were present, were cloned by a limiting dilution method.

b6. The cloned cells were screened again by the method of the sections b3 to b5, and SLP1- or SLP2-specific CD4-positive T-cell clones (hereinafter sometimes referred to as CD4 clones) were selected. Thus, a plurality of T-cell clones were obtained.

b7. The resultant clone T-cells were subjected to PHA stimulation to grow the cells, followed by frozen storage. One of the obtained CD4 clones is 4C34-1.

c. Establishment Method for SLP1- or SLP2-specific CD8-positive T-cell Clone

SLP1- or SLP2-specific CD8-positive T-cell clones (hereinafter sometimes referred to as CD8 clones) were prepared in the same manner as in the section "b". One of the obtained CD8 clones is 8C34TY.

d. Reactions of Obtained Clone T Cells to SLP1 and SLP2 and Epitope Analysis

The CD4 clone 4C34-1 obtained in the section "b", and the CD8 clone 8C34TY obtained in the section "c" were analyzed.

20 peptides each formed of part of the amino acid sequence of XAGE1 were synthesized. Their respective amino acid sequences are set forth in SEQ ID NOS: 5 to 24. In addition, the positions of the peptides on the amino acid sequence of XAGE1 are as shown in the sequence listing and FIG. 19. The peptides were synthesized by a general synthesis method at PH Japan (Japan). The purity of each of the peptides is 95% or more.

$2 \times 10^4$ CD4 clone or CD8 clone T-cells were subjected to stimulated culture with 1 μM of each peptide in the presence of an equal number of T-APCs for 12 hours, and IFNγ in the supernatant was detected by an ELISA method.

Figure 19:
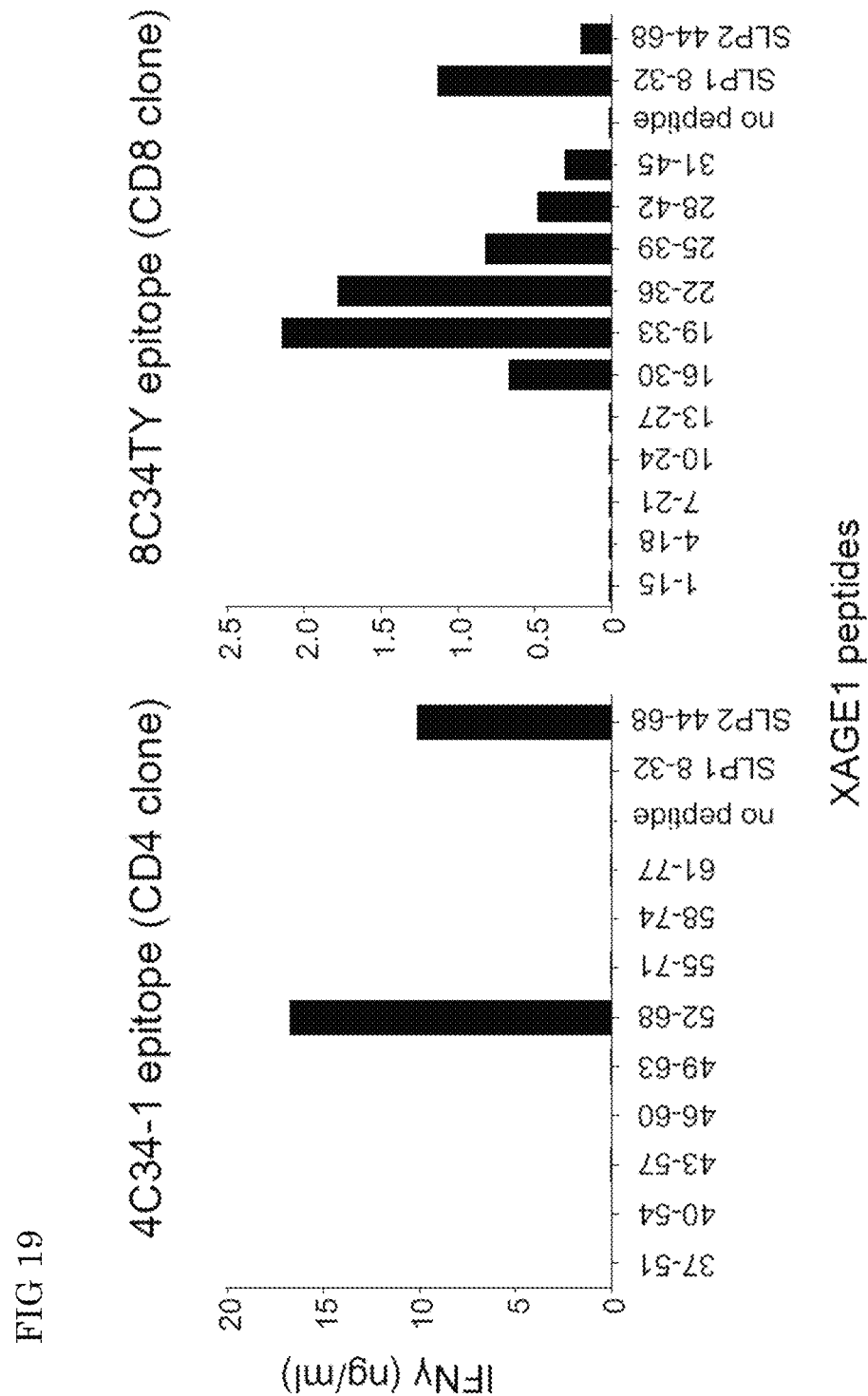
FIG. 19 shows peptides to be recognized by 4C34-1, which is a CD4-positive T-cell clone (hereinafter sometimes referred to as CD4 clone) specific to SLP2, and 8C34TY, which is a CD8-positive T-cell clone (hereinafter sometimes referred to as CD8 clone) specific to SLP1.

The results are shown in FIG. 19. The CD4 clone 4C34-1 recognized amino acids 52 to 68 in SLP2 (44-68). In addition, the CD8 clone 8C34TY recognized SLP1 (8-32) and amino acids 19 to 33, suggesting the presence of epitopes therein.

Through the stimulated culture of peripheral blood mononuclear cells of anti-XAGE1 antibody-positive patients with SLP1 and SLP2, a plurality of CD4 T-cells and CD8 T-cells recognizing SLP1 and SLP2 were successfully detected. This indicates that the SLP1 and SLP2 vaccine is a multi-antigenic cancer vaccine containing various epitopes unlike an epitope vaccine to be recognized by T-cells.

<Usefulness of Combination Therapy of SLP1 and SLP2>

Figure 20:
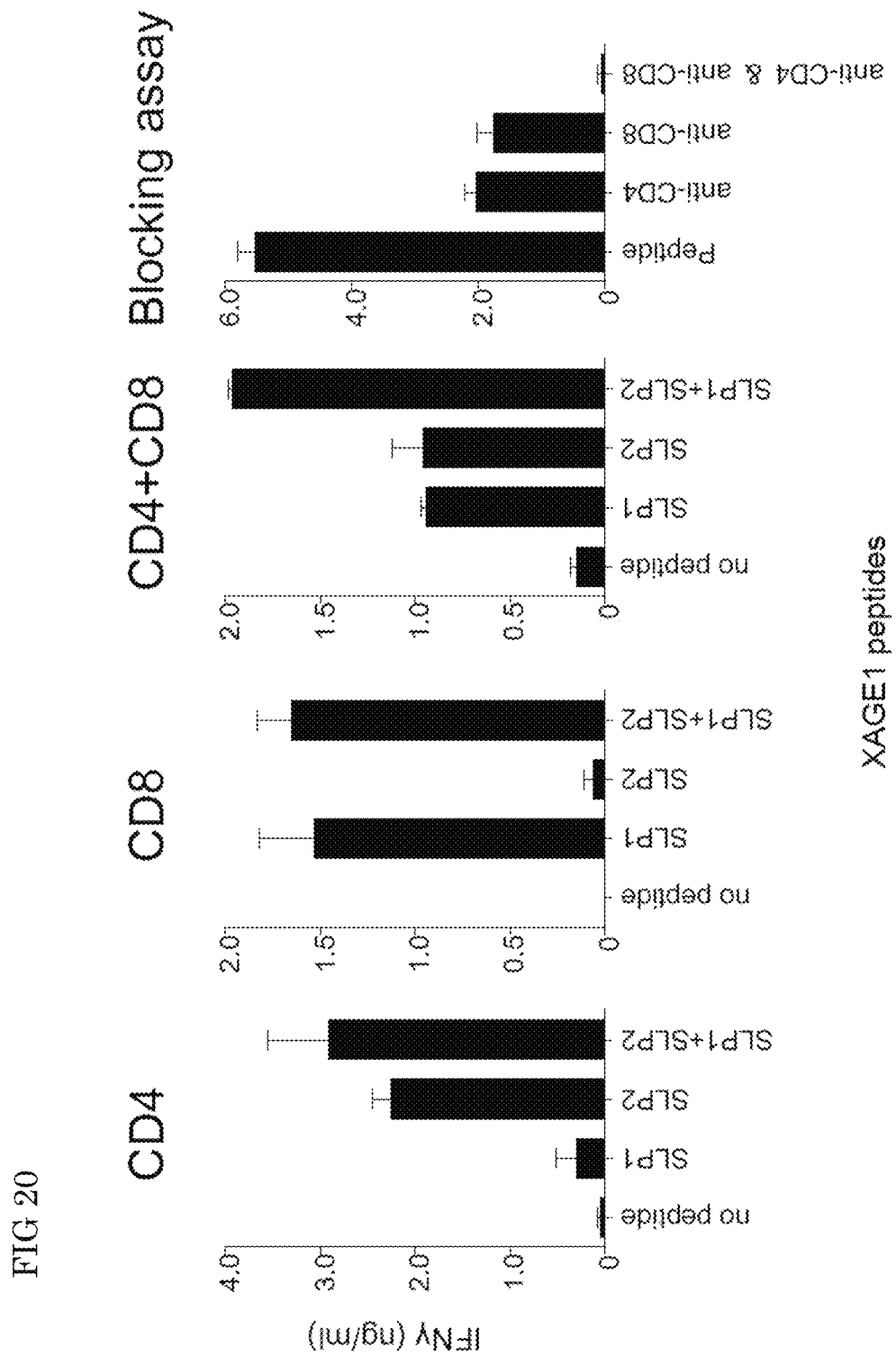
FIG. 20 shows the results of stimulation of CD4 clone (4C34-1) T-cells, CD8 clone (8C34TY) T-cells, and a mixture of these T-cells with SLP1 alone, SLP2 alone, or the combination of SLP1 and SLP2. It is shown that stimulation with the combination of SLP1 and SLP2 induces a more potent immune response.

$1 \times 10^4$ CD4 clone (4C34-1) T-cells were subjected to stimulated culture with SLP1 alone (1 μM), SLP2 alone (1 μM), or the combination of the peptides (1 μM each) in the presence of an equal number of T-APCs for 12 hours, and IFNγ in the supernatant was detected by an ELISA method (FIG. 20). The CD4 clone T-cells recognized SLP2.

In the same manner, $1 \times 10^4$ CD8 clone (8C34TY) T-cells were subjected to stimulated culture with SLP1 alone (1 μM), SLP2 alone (1 μM), or the combination of the peptides (1 μM each) in the presence of an equal number of T-APCs for 12 hours, and IFNγ in the supernatant was detected by an ELISA method (FIG. 20). The CD8 clone T-cells recognized SLP1.

In view of the foregoing, $1 \times 10^4$ CD4 clone (4C34-1) T-cells and $1 \times 10^4$ CD8 clone (8C34TY) T-cells were subjected to stimulated culture with SLP1 alone (1 μM), SLP2 alone (1 μM), or the combination of the peptides (1 μM each) in the presence of an equal number of T-APCs for 12 hours, and IFNγ in the supernatant was detected by an ELISA method. As a result, the combination of SLP1 and SLP2 increased the reaction.

Human peripheral blood does not contain CD4-positive T-cells alone or CD8-positive T-cells alone, and hence the combination of SLP1 and SLP2 can induce a more potent immune response than SLP1 alone or SLP2 alone.

<Ability to Induce IgG Immunity>

$1 \times 10^5$ of peripheral blood mononuclear cells obtained in the section "a" were subjected to stimulated culture with SLP1 alone (1 μM), SLP2 alone (1 μM), or the combination of the peptides (1 μM each) for 12 hours in the presence of $2 \times 10^4$ CD4 clone 4C34-1 T-cells, $2 \times 10^4$ CD8 clone C34TY T-cells, and Protein Transport Inhibitor Cocktail (eBioscienc, US) (500-fold diluted).

Figure 21A:
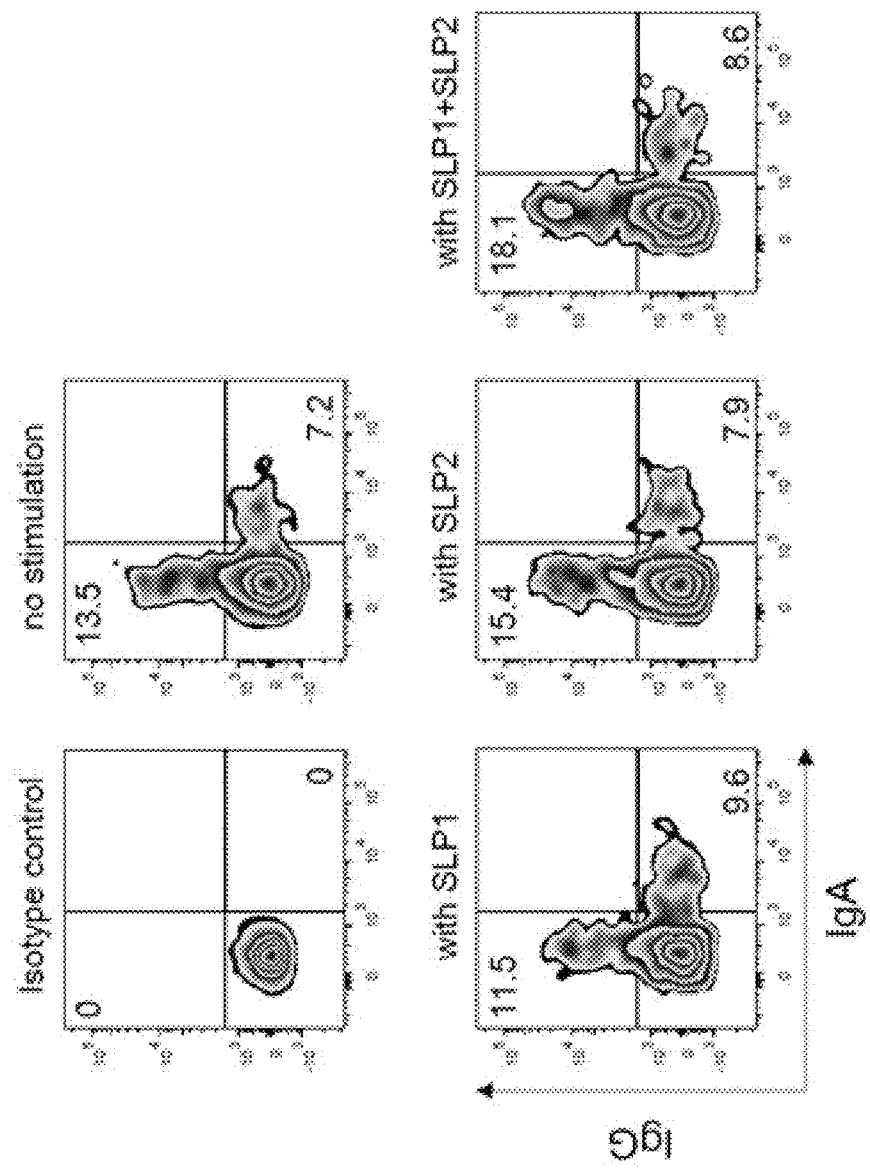
FIG. 21 shows the results of detection of IgG and IgA on B-cell surfaces after stimulation of peripheral blood mononuclear cells with SLP1 alone, SLP2 alone, or the combination of the peptides in the presence of CD4 clone T-cells and CD8 clone T-cells. The expression of IgG on the B-cell surfaces was found to be increased by the combination of SLP1 and SLP2. Meanwhile, there was no change in expression amount of IgA.
Figure 21B:
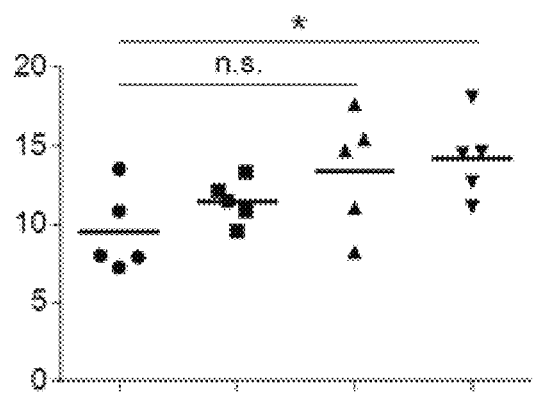
Figure 21B:
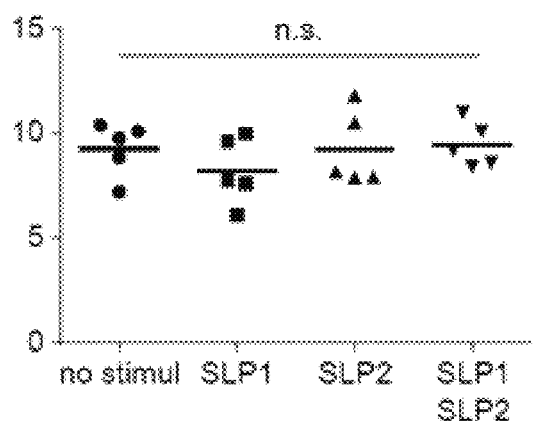

Gating on B-cells was performed by a flow cytometry method, and IgG or IgA on B-cell surfaces under stimulation with each peptide was detected (FIG. 21). The expression of IgG on B-cell surfaces was found to be increased by the combination of SLP1 and SLP2. Meanwhile, there was no change in expression amount of IgA.

Next, $1 \times 10^5$ of B-cells separated from the serum of the same patients as in the section "a" were subjected to stimulated culture with SLP1 alone (1 μM), SLP2 alone (1 μM), or the combination of the peptides (1 μM each) for 72 hours in the presence of $2 \times 10^4$ CD4 clone 4C34-1 T-cells and $2 \times 10^4$ CD8 clone 8C34TY T-cells.

Figure 22:
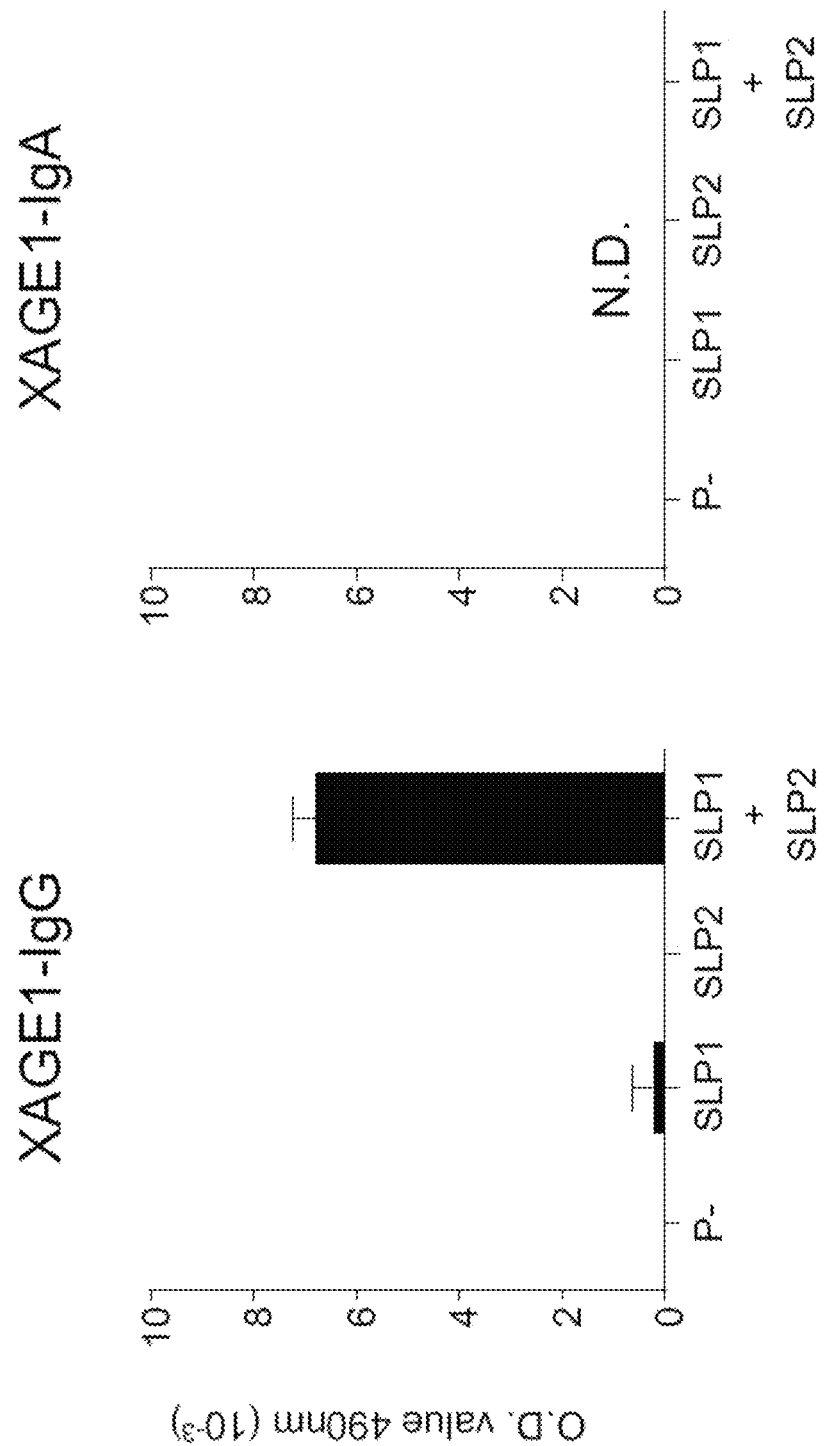
FIG. 22 shows the results of detection of XAGE1-specific antibodies in culture supernatants after stimulation of B-cells with SLP1 alone, SLP2 alone, or the combination of the peptides in the presence of CD4 clone T-cells and CD8 clone T-cells. In the case of the combination of SLP1 and SLP2, XAGE1-IgG was produced, and the production of IgA was not found.

XAGE1-specific antibodies present in the culture supernatant were detected. As a result, in the case of the combination of SLP1 and SLP2, the detection of XAGE1-IgG was found, and IgA was not found (FIG. 22).

As described above, antigen-specific IgG was detected from B-cells by stimulating peripheral blood mononuclear cells of anti-XAGE1 antibody-positive patients with the combination of SLP1 and SLP2 in vitro. Accordingly, a composition containing SLP1 and SLP2 is a cancer vaccine capable of inducing the production of XAGE1-IgG, and capable of inducing an immune response against cancer. XAGE1-IgG positivity indicates a treatment-responsive group and a favorable prognosis group, and hence the composition containing SLP1 and SLP2 can lead a patient to be treatment-responsive and to have a favorable prognosis.

<Safety>

A toxicity trial was performed in which a mixture of SLP1 and SLP2 was repeatedly administered for 10 weeks (intermittently administered five times every 14 days) with an adjuvant into the dorsal skin of Sprague-Dawley rats (Crl: CD(SD), 6-week-old at the start of administration, a group of 10 males and 10 females).

The following two doses were adopted as the doses of the test substances: 0.2 mg/kg (SLP1: 0.2 mg/kg+SLP2: 0.2 mg/kg) and 2 mg/kg (SLP1: 2 mg/kg+SLP2: 2 mg/kg). SLP1 and SLP2 dissolved in water for injection and Picibanil were mixed with an equal amount of an oil adjuvant MONTANIDE ISA 51 VG (ISA51) to provide an emulsion, which was administered into the dorsal skin in an administration volume of 1 mL/kg. Further, a vehicle control group to be administered an emulsion of water for injection and Picibanil with ISA51 and a physiological saline control group to be administered physiological saline were formed.

During the administration period, general condition observation, body weight measurement, and food intake measurement were performed, and urine examination and ophthalmologic examination were performed in week 10 of the administration. At the end of the administration period, hematological examination, blood chemical examination, an autopsy, organ weight measurement, and histopathological examination were performed.

No death resulting from the test substance administration was observed, and no change due to the test substance administration was observed in any of the examinations.

At the administration site (under the dorsal skin), in almost all male and female cases of the vehicle control group and the test substance administration group, a white focus probably due to the retention of the administered substances was observed in the autopsy, and infiltration of lymphocytes/plasma cells and histiocytes, and fibrosis were histopathologically observed in addition to the retention of the administered substances. In addition, neutrophil infiltration was also observed in a few of the female cases of the vehicle control group. However, all changes in the test substance administration group were comparable to those in the vehicle administration group, and no enhancement in change due to SLP1 and SLP2 was found.

An inflammatory reaction under the skin at the administration site resulting from the adjuvant was observed, but no enhancement due to SLP1 and SLP2 was found, and no toxicologically significant change resulting from the test substance administration was observed. Therefore, it was considered that the no-observed-adverse-effect levels of SLP1 and SLP2 in this trial were more than 2 mg/kg for both males and females.

<Production of Vaccine for Humans>

SLP1 and SLP2 were emulsified together with an adjuvant OK432 Picibanil in Montanide (ISA51, manufactured by SEPPIC) to provide a composition for inducing an immune response (hereinafter sometimes referred to as XAGE1 vaccine). More specifically, peptide mixtures formed of two kinds of long-chain peptides prepared in GMP grade were prepared in three levels of doses.

Low-dose: 500 μg (SLP1: 250 μg+SLP2: 250 μg)
Middle-dose: 1 mg (SLP1: 500 μg+SLP2: 500 μg)
High-dose: 2 mg (SLP1: 1 mg+SLP2: 1 mg)

Each of those peptide mixtures was mixed into 1.25 ml of a raw diet together with 0.2 KE of OK432 (Chugai Pharmaceutical Co., Ltd.), and emulsified in 1.25 ml of Montanide.

<Safety (Phase I Clinical Trial)>

The XAGE1 vaccine was administered to advanced lung adenocarcinoma patients. This trial is a phase I clinical trial involving confirming safety as a primary purpose, and investigating a change in XAGE1 antibody titer caused by the administration of a trial drug as a secondary purpose. This clinical trial was performed in accordance with "the Declaration of Helsinki", "Ethical Guidelines for Medical and Health Research Involving Human Subjects", and an XAGE1 vaccine clinical trial implementation planning worksheet, and in conformity with ICH E6(R1)—Guideline for Good Clinical Practice (GCP) as much as possible.

The trial was performed targeting advanced or postoperatively recurring lung adenocarcinoma using the XAGE1 vaccine in the three levels of doses described above. The XAGE1 vaccine was administered to two different limb sites every time. The administration was performed a total of four times at intervals of 2 weeks. Each dose was administered to three patients each.

With regard to safety, the kind, frequency, and degree of an adverse event were observed. For the grading of the adverse event, Common Terminology Criteria for Adverse Events (CTCAE) v4.0 Japanese Translation JCOG Version is used. The adverse event was judged in accordance with CTCAE v4.0. An observation period for the adverse event was set to be from the day of the initial administration of the trial drug to 6 weeks after final administration (end of an individual trial).

Evaluation for safety was finished in a total of 7 patients, i.e., 3 patients in the low-dose group, 3 patients in the middle-dose group, and 1 patient in the high-dose group. As shown in Table 1, all adverse events due to the XAGE1 vaccine were mild, and no serious adverse event was observed.

TABLE 1

| Subject identification code | Event name | Severity | Seriousness | Treatment | Outcome |
|---|---|---|---|---|---|
| KMX-01 | Myalgia | G2 | Non-serious | None | Recovered |
| KMX-01 | Skin induration | G1 | Non-serious | None | Unrecovered |
| KMX-03 | Fever | G1 | Non-serious | Prescription of other agent (CALONAL) | Recovered |
| KMX-03 | Loss of appetite | G1 | Non-serious | None | Remitted |
| KMX-01 | Headache | G1 | Non-serious | None | Recovered |
| KMX-01 | Nausea | G1 | Non-serious | None | Recovered |
| KMX-02 | Pain (injection site) | G1 | Non-serious | None | Recovered |
| KMX-02 | Skin induration | G1 | Non-serious | None | Unrecovered |
| KMX-02 | Increase in white blood cells | G1 | Non-serious | None | Unrecovered |
| KMX-03 | Malaise | G1 | Non-serious | None | Remitted |
| KMX-03 | Chills | G1 | Non-serious | None | Recovered |
| KMX-03 | Increase in white blood cells | G1 | Non-serious | None | Recovered |
| KMX-03 | Skin induration | G1 | Non-serious | None | Unrecovered |
| KMX-03 | Itch (injection site) | G1 | Non-serious | Topical steroid | Recovered |
| KMX-02 | Fever | G1 | Non-serious | Prescription of other agent (CALONAL) | Recovered |
| KMX-02 | Pneumonitis | G2 | Non-serious | Prescription of other agent (Prednisolone) | Recovered |
| KMX-04 | Increase in white blood cells | G1 | Non-serious | None | Unrecovered |
| KMX-05 | Skin induration | G1 | Non-serious | None | Unrecovered |

TABLE 1-continued

| Subject identification code | Event name | Severity | Seriousness | Treatment | Outcome |
|---|---|---|---|---|---|
| KMX-05 | Fever | G1 | Non-serious | Prescription of other agent (CALONAL) | Remitted |
| KMX-06 | Dyspnea | G1 | Non-serious | None | Recovered |
| KMX-06 | Fever | G1 | Non-serious | Prescription of other agent (CALONAL) | Recovered |
| KMX-06 | Skin induration | G1 | Non-serious | None | Unrecovered |
| KMX-07 | Skin induration | G1 | Non-serious | None | Unrecovered |

<With regard to Effectiveness of XAGE1 Vaccine>
1. Induction of XAGE1-IgG

Figure 23:
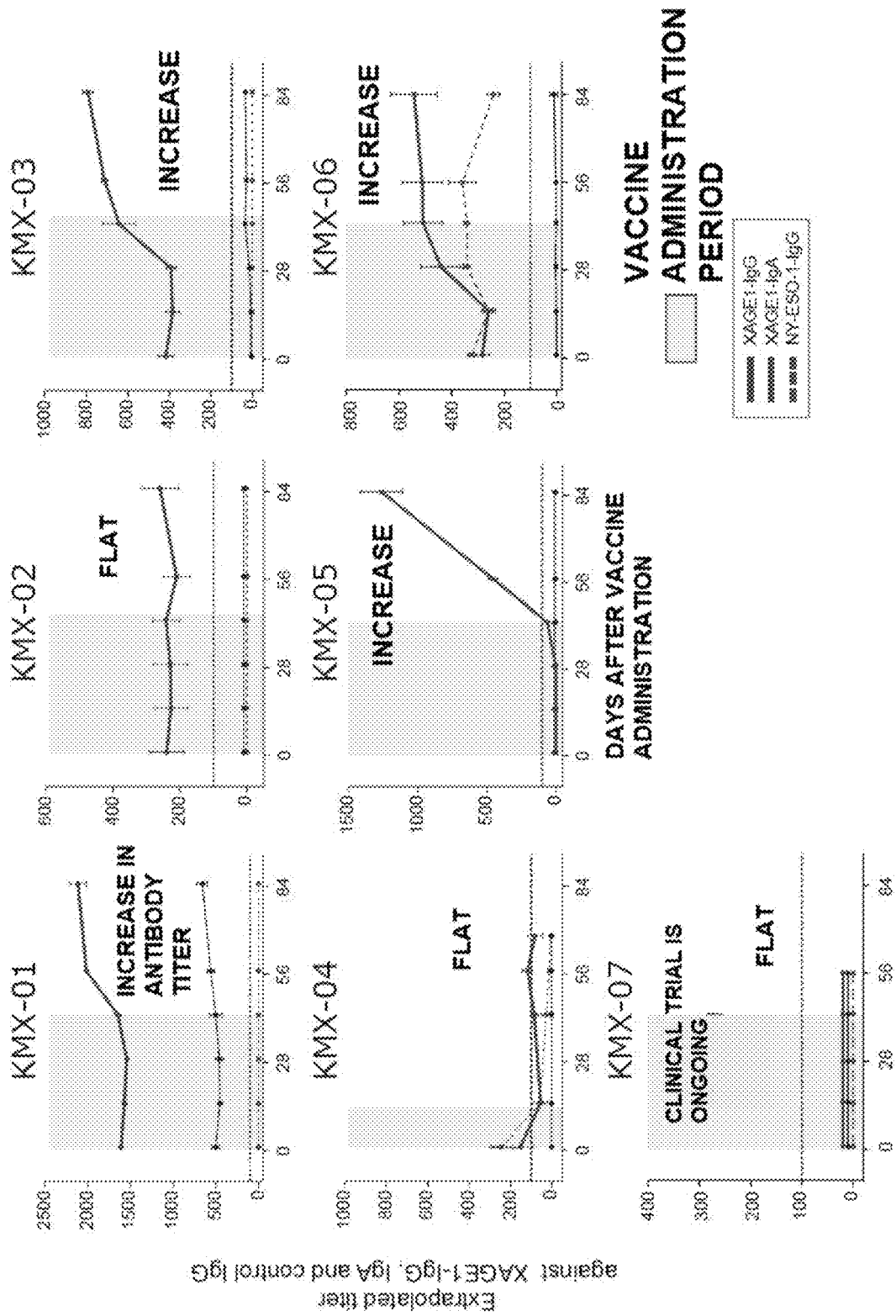
FIG. 23 shows that the administration of an XAGE1 vaccine containing SLP1 and SLP2 was found to increase an XAGE1-IgG antibody titer in four out of seven cases, and did not induce XAGE1-IgA and NY-ESO-1-IgG.

The administration of the XAGE1 vaccine was found to increase XAGE1-IgG antibody titer in four out of seven patients, and did not induce XAGE1-IgA and NY-ESO-1-IgG (FIG. 23).
a. An increase in XAGE1-IgG antibody titer was found in two out of three patients in XAGE1 vaccine low-dose group.
b. An increase in XAGE1-IgG antibody titer was found in two out of three patients in XAGE1 vaccine middle-dose group.
c. XAGE1-IgA was positive (KMX-01) in one out of seven patients since before treatment, but was negative in the other patients. The XAGE1 vaccine was not found to increase XAGE1-IgA antibody titer.

Thus, specific induction of XAGE1-IgG immunity with SLP1 and SLP2, which had been observed in vitro, was also observed in vivo.

2. Tumor Marker

Figure 24:
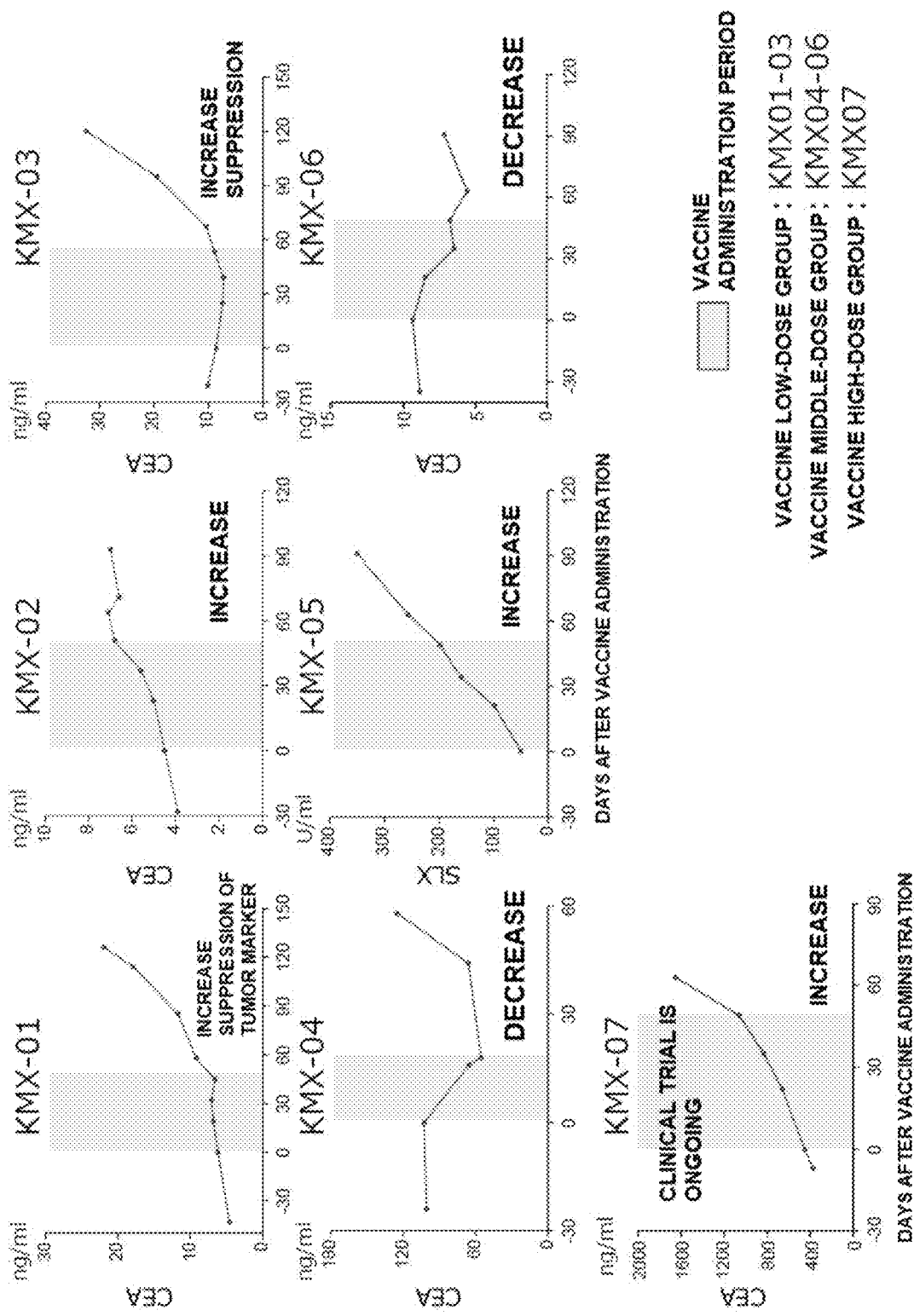
FIG. 24 shows that the increased suppression or decrease of a tumor marker was observed in four out of seven patients through the administration of XAGE1 vaccine.

As shown in FIG. 24, the increase suppression or decrease of a tumor marker was observed in four out of seven patients.
a. The increase suppression of the tumor marker was found in two out of three patients in XAGE1 vaccine low-dose group.
b. The decrease of the tumor marker was found in two out of three patients in the XAGE1 vaccine middle-dose group.
c. The increase suppression or decrease of tumor marker was found in three out of four patients in which XAGE1-IgG antibody titer was increased. Meanwhile, the increase of tumor marker was observed in two out of three patients in which an increase in XAGE1-IgG antibody titer was not found.

Thus, through the use of XAGE1 vaccine, the increase suppression or decrease of tumor marker was observed.

2. Induction of Antigen-Specific T Cells

Figure 25:
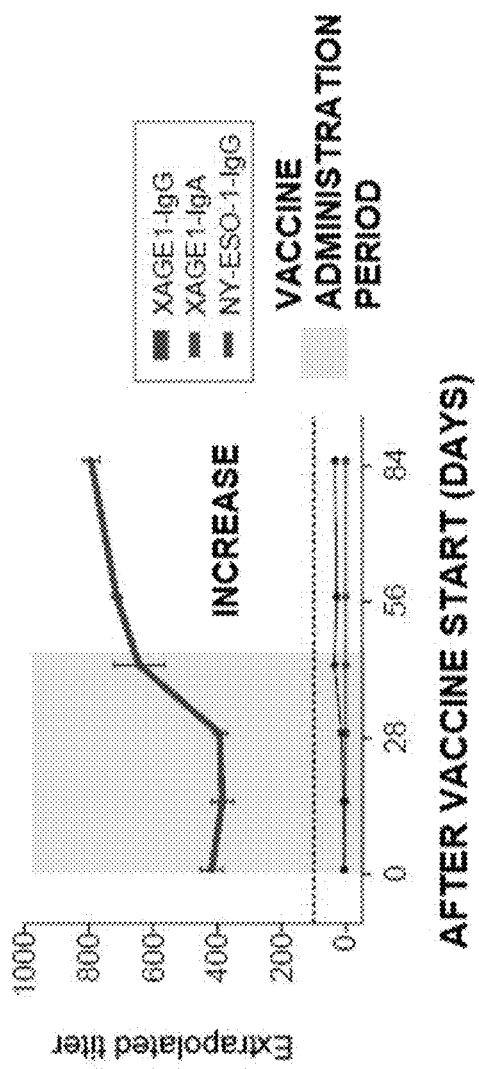
FIG. 25 shows that low-dose administration of XAGE1 vaccine was able to induce immune responses. It is shown that CD4-positive T-cells obtained from patients mainly respond to SLP1, and the combination of SLP1 and SLP2 enhances the immune responses.
Figure 25:
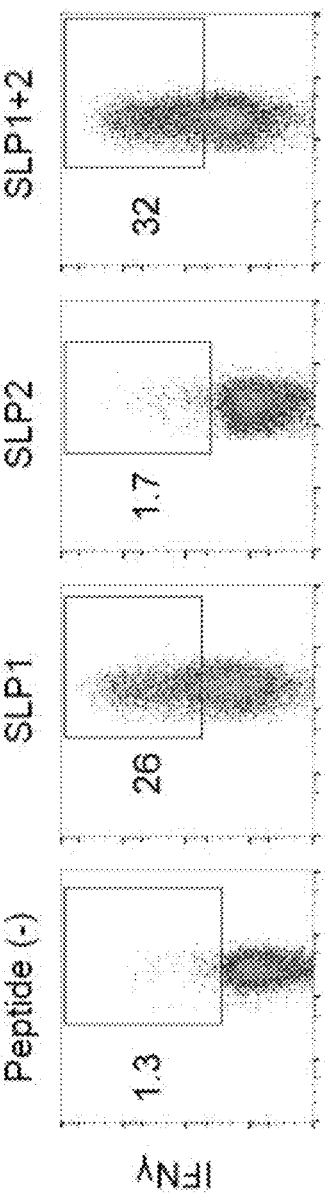
Figure 26:
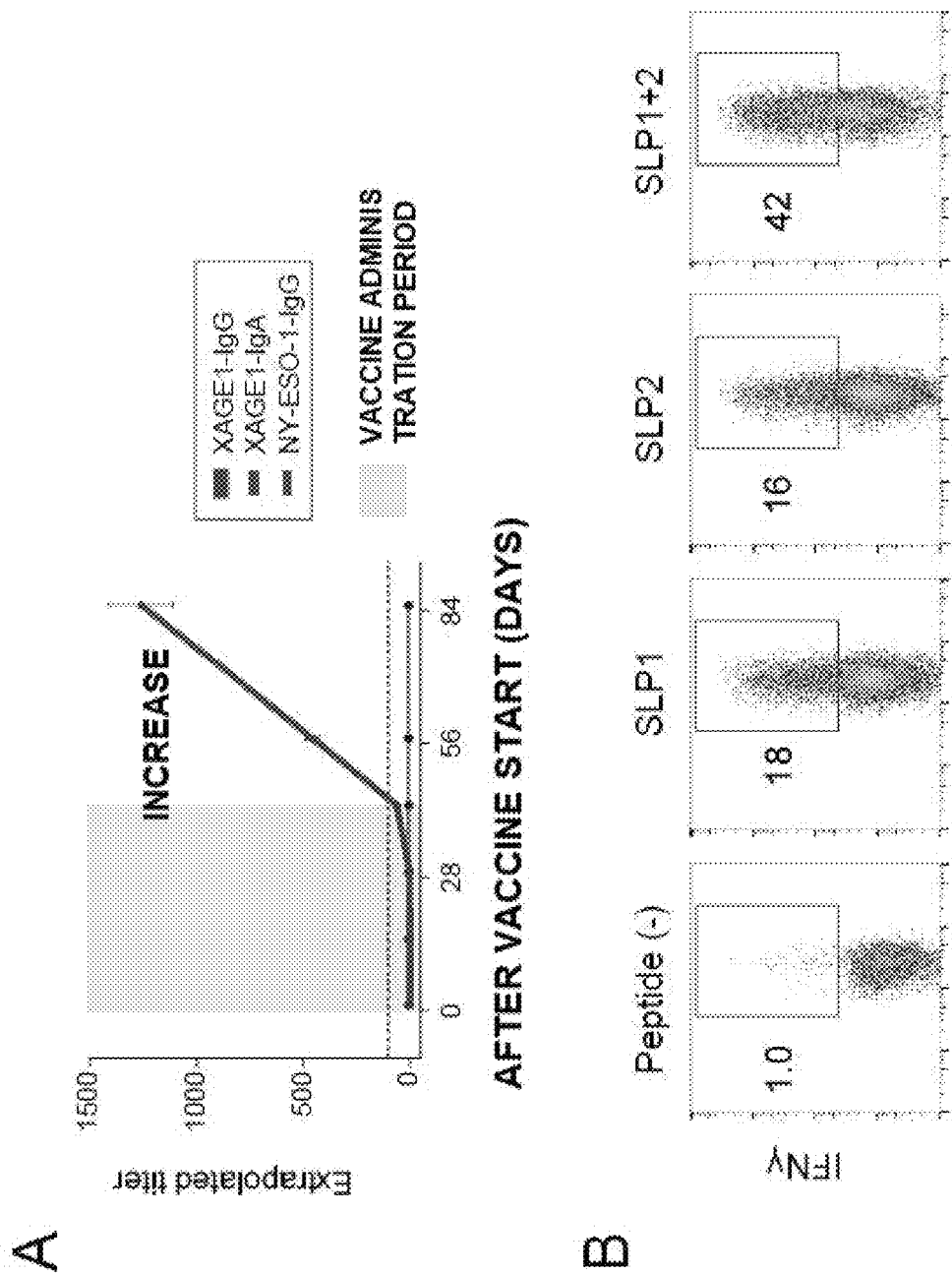
FIG. 26 shows that middle-dose administration of XAGE1 vaccine was able to induce the immune responses. It is shown that CD4-positive T-cells obtained from patients react to SLP1 and SLP2, and the combination of SLP1 and SLP2 enhances the immune responses.

CD4-positive T-cells were separated from peripheral blood of low-dose administered patients and middle-dose administered patients, and the induction of antigen-specific T-cells by XAGE1 vaccine administration was investigated. In both the low-dose administered patients and the middle-dose administered patients, IFN-γ was produced through the stimulation with the combination of SLP1 and SLP2, proving that T-cells reactive to the SLP1 antigen and the SLP2 antigen were induced (FIG. 25 and FIG. 26).

In the middle-dose administered patients, stimulation with SLP1 and SLP2 alone was found to cause the production of IFNγ. This proves that SLP1 and SLP2 contain a plurality of epitopes, and demonstrates that the XAGE1 vaccine is more useful than the vaccine of SLP1 alone and the vaccine of SLP2 alone. In addition, through stimulation with the combination of SLP1 and SLP2, more potent production of IFNγ was able to be confirmed (FIG. 26).

Thus, it was proved in vivo that the XAGE1 vaccine containing SLP1 and SLP2 was a vaccine capable of inducing antigen-specific T-cells in cancer patients, and was also a multi-antigenic vaccine containing a plurality of epitopes, thus being a vaccine capable of inducing a more potent immune response by virtue of the mixing of SLP1 and SLP2.

An experimental protocol is as described below. a) A mononuclear cell fraction was obtained from peripheral blood in week 12 after the start of vaccine administration by a density gradient centrifugation method. Then, with the use of anti-CD4 antibody-bound beads, anti-CD8 antibody-bound beads, and anti-CD19 antibody-bound beads (manufactured by Miltenyi Biotec), a CD8-positive fraction, a CD4-positive fraction, a CD19-positive fraction, and a $CD4^-CD8^-CD19^-$ fraction were sequentially separated by a magnetic-activated cell sorting method (MACS, manufactured by Miltenyi Biotec).

b) $1 \times 10^6$ CD4-positive T-cells, and an equal number of X-ray irradiated (60 Gy) $CD4^-CD8^-$ T-cells serving as antigen-presenting cells were cocultured in the presence of 1 μM each of SLP1 and SLP2 using a 96-well plate in a $CO_2$ incubator for 12 days. As a medium for culturing T-cells, 5% pooled serum/AIM-V (IL-2 10 IU/ml, IL-7 10 ng/ml) was used unless otherwise specified.

c) Detection of IFN-γ-Producing Cells

The cell population including antigen-specific T-cells grown by the stimulated culture was subjected to secondary stimulation as described below, and antigen-specific cytokine production was detected.

To the cells that had been subjected to the stimulated culture, an equal number of autologous EBV-B-cells (Epstein-Barr virus-infected B-cells: used as antigen-presenting cells) and a peptide (SLP1, SLP2, or SLP1+SLP2) were added, and secondary stimulation was performed in a $CO_2$ incubator at 37° C. for 4 hours. As a control, secondary stimulation was performed in a $CO_2$ incubator at 37° C. for 4 hours without the addition of any peptide.

After that, in order to label the cultured cells using 2 μl of a human IFN-γ catch antibody (manufactured by Miltenyi Biotec), the cultured cells were suspended in 10 ml of an AIM-V medium and subjected to a reaction in a $CO_2$ incubator at 37° C. for 45 minutes while being suspended using a rotator (MACSmix, manufactured by Miltenyi Biotec). After having been washed, the cells were stained by adding 2 μl of a PE-labeled human IFN-γ antibody (manufactured by Miltenyi Biotec), 2 μl of 7AAD (manufactured by BD), and 1 μl of an FITC-labeled anti-human CD4 antibody or an FITC-labeled anti-human CD8 antibody (manufactured by Miltenyi Biotec).

After the staining, a FACS buffer (1% FCS/PBS, 0.02% sodium azide) was added to wash the cells, and flow cytometry was performed using FACS Calibur (manufactured by BD) to detect IFN-γ-producing cells. The frequency of the IFN-γ-producing cells was analyzed using data analysis software (FlowJo, manufactured by Tree Star). The results are shown in FIG. 25 and FIG. 26.

INDUSTRIAL APPLICABILITY

The detection method of the present invention can predict the effect of cancer treatment, thus expanding the possibilities of cancer treatment. In addition, the detection method contributes to medical economy as well. In addition, the composition for inducing an immune response of the present invention can be directly used for the treatment of cancer, and besides, can enhance the effect of chemotherapy, immunotherapy, or immune checkpoint inhibitors to lead a treatment non-responder to be treatment-responsive.

SEQUENCE LIST

Sequence List GP18-1007PCT.txt

The invention claimed is:

1. An examination method for prediction of effect of treatment of cancer for increased median survival time of overall survival or progression-free survival (PFS) over untreated subject in a subject suffering from cancer with immune checkpoint molecule inhibitor drug, comprising detecting antibody against a cancer/testis antigen in clinical samples, wherein the cancer/testis antigen is selected from the group consisting of XAGE1, NY-ESO-1, MAEL, BAGE, BORIS, MAGE-B3, and SSX4, wherein the detecting comprises detecting IgG-type antibody against the cancer/testis antigen, or IgG-type antibody against the cancer/testis antigen and IgA-type antibody against the cancer/testis antigen, wherein presence of IgG-type antibody is indicative of therapeutically effective condition for treatment with the checkpoint molecule inhibitor, and administering the checkpoint molecule inhibitor to the subject exhibiting positive anti-cancer/testis antigen antibody in the sample, wherein the immune checkpoint molecule is PD-1.

2. The method according to claim 1, wherein clinical samples are samples collected from patients before cancer treatment.

3. The method according to claim 1, further comprising judging that treatment with immune checkpoint molecule inhibitor drug has effects in at least one patient selected from the group consisting of the following cases 1) or 2):
   1) IgG-type antibodies against cancer/testis antigens are positive; or
   2) IgG-type antibodies against cancer/testis antigens are positive, and IgA-type antibodies against cancer/testis antigens are negative.

4. The method of claim 1, which is carried out without determining PD-L1 expression.

5. The method of claim 1, wherein the cancer/testis antigen is XAGE1.

6. A method for treating a patient with an immune checkpoint molecule inhibitor drug, wherein the patient is suffering from cancer, the method comprising the steps of: determining whether the patient exhibits antibody to cancer/testis antigen comprising: obtaining or having obtained a biological sample from the patient; and performing or having performed an antibody detection assay on the biological sample to determine if the patient exhibits antibody to cancer/testis antigen; wherein in the following resultant cases 1) or 2):
   1) IgG-type antibodies against cancer/testis antigens are positive; or
   2) IgG-type antibodies against cancer/testis antigens are positive, and IgA-type antibodies against cancer/testis antigens are negative, administering immune checkpoint molecule inhibitor drug to the patient, wherein the cancer/testis antigen is XAGE1.

7. The method of claim 6, which is carried out without determining PD-L1 expression.

8. The method of claim 1, wherein the detecting comprises detecting IgG-type antibody against the cancer/testis antigen and IgA-type antibody against the cancer/testis antigen, wherein positive IgG-type antibody and negative IgA-type is indicative of therapeutically effective condition.

9. The method of claim 1, wherein the inhibitor of PD-1 is anti-PD-1 antibody.

10. An examination method for prediction of effect of treatment of cancer for increased median survival time of overall survival or progression-free survival (PFS) over untreated subject in a subject suffering from cancer with immune checkpoint molecule inhibitor drug, comprising detecting antibody against a cancer/testis antigen in clinical samples, wherein the cancer/testis antigen is selected from the group consisting of XAGE1, NY-ESO-1, MAEL, BAGE, BORIS, MAGE-B3, and SSX4, wherein the detecting comprises detecting IgG-type antibody against the cancer/testis antigen, or IgG-type antibody against the cancer/testis antigen and IgA-type antibody against the cancer/testis antigen, wherein presence of IgG-type antibody is indicative of therapeutically effective condition for treatment with the checkpoint molecule inhibitor, and administering the checkpoint molecule inhibitor to the subject exhibiting positive anti-cancer/testis antigen antibody in the sample, wherein the detecting comprises detecting IgG-type antibody against the cancer/testis antigen and IgA-type antibody against the cancer/testis antigen, wherein positive IgG-type antibody and negative IgA-type is indicative of therapeutically effective condition.

11. The method according to claim 10, wherein clinical samples are samples collected from patients before cancer treatment.

12. The method of claim 10, which is carried out without determining PD-L1 expression.

13. The method of claim 10, wherein the cancer/testis antigen is XAGE1.

14. An examination method for prediction of effect of treatment of cancer for increased median survival time of overall survival or progression-free survival (PFS) over untreated subject in a subject suffering from cancer with immune checkpoint molecule inhibitor drug, comprising detecting antibody against a cancer/testis antigen in clinical samples, wherein the cancer/testis antigen is selected from the group consisting of XAGE1, NY-ESO-1, MAEL, BAGE, BORIS, MAGE-B3, and SSX4, wherein the detecting comprises detecting IgG-type antibody against the cancer/testis antigen, or IgG-type antibody against the cancer/testis antigen and IgA-type antibody against the cancer/testis antigen, wherein presence of IgG-type antibody is indicative of therapeutically effective condition for treatment with the checkpoint molecule inhibitor, and administering the checkpoint molecule inhibitor to the subject exhibiting positive anti-cancer/testis antigen antibody in the sample, wherein the cancer/testis antigen is XAGE1.

15. The method according to claim 14, wherein clinical samples are samples collected from patients before cancer treatment.

16. The method according to claim 14, further comprising judging that treatment with immune checkpoint molecule inhibitor drug has effects in at least one patient selected from the group consisting of the following cases 1) or 2):
   1) IgG-type antibodies against cancer/testis antigens are positive; or
   2) IgG-type antibodies against cancer/testis antigens are positive, and IgA-type antibodies against cancer/testis antigens are negative.

17. The method of claim 1, which is carried out without determining PD-L1 expression.

* * * * *

```
SEQUENCE LISTING

<160> NUMBER OF SEQ ID NOS: 24

<210> SEQ ID NO 1
<211> LENGTH: 25
<212> TYPE: PRT
<213> ORGANISM: Artificial Sequence
<220> FEATURE:
<223> OTHER INFORMATION: A part of XAGE1

<400> SEQUENCE: 1

Asn Gln Gln Leu Lys Val Gly Ile Leu His Leu Gly Ser Arg Gln Lys
1               5                   10                  15

Lys Ile Arg Ile Gln Leu Arg Ser Gln
            20                  25

<210> SEQ ID NO 2
<211> LENGTH: 25
<212> TYPE: PRT
<213> ORGANISM: Artificial Sequence
<220> FEATURE:
<223> OTHER INFORMATION: A part of XAGE1

<400> SEQUENCE: 2

Ile Ser Gln Thr Pro Gly Ile Asn Leu Asp Leu Gly Ser Gly Val Lys
1               5                   10                  15

Val Lys Ile Ile Pro Lys Glu Glu His
            20                  25

<210> SEQ ID NO 3
<211> LENGTH: 81
<212> TYPE: PRT
<213> ORGANISM: Homo sapiens

<400> SEQUENCE: 3

Met Glu Ser Pro Lys Lys Lys Asn Gln Gln Leu Lys Val Gly Ile Leu
1               5                   10                  15

His Leu Gly Ser Arg Gln Lys Lys Ile Arg Ile Gln Leu Arg Ser Gln
            20                  25                  30

Cys Ala Thr Trp Lys Val Ile Cys Lys Ser Cys Ile Ser Gln Thr Pro
        35                  40                  45

Gly Ile Asn Leu Asp Leu Gly Ser Gly Val Lys Val Lys Ile Ile Pro
    50                  55                  60

Lys Glu Glu His Cys Lys Met Pro Glu Ala Gly Glu Glu Gln Pro Gln
65                  70                  75                  80

Val

<210> SEQ ID NO 4
<211> LENGTH: 180
<212> TYPE: PRT
<213> ORGANISM: Homo sapiens
```

<400> SEQUENCE: 4

Met Gln Ala Glu Gly Arg Gly Thr Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Ala Pro Arg Gly Pro
    50                  55                  60

His Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 5
<211> LENGTH: 15
<212> TYPE: PRT
<213> ORGANISM: Artificial Sequence
<220> FEATURE:
<223> OTHER INFORMATION: A part of XAGE1 1-15

<400> SEQUENCE: 5

Met Glu Ser Pro Lys Lys Lys Asn Gln Gln Leu Lys Val Gly Ile
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: A part of XAGE1 4-18

<400> SEQUENCE: 6

Pro Lys Lys Lys Asn Gln Gln Leu Lys Val Gly Ile Leu His Leu
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: A part of XAGE1 7-21

<400> SEQUENCE: 7

Lys Asn Gln Gln Leu Lys Val Gly Ile Leu His Leu Gly Ser Arg
1               5                   10                  15

-continued

```
<210> SEQ ID NO 8
<211> LENGTH: 15
<212> TYPE: PRT
<213> ORGANISM: Artificial Sequence
<220> FEATURE:
<223> OTHER INFORMATION: A part of XAGE1 10-24

<400> SEQUENCE: 8

Gln Leu Lys Val Gly Ile Leu His Leu Gly Ser Arg Gln Lys Lys
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: A part of XAGE1 13-27

<400> SEQUENCE: 9

Val Gly Ile Leu His Leu Gly Ser Arg Gln Lys Lys Ile Arg Ile
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: A part of XAGE1 16-30

<400> SEQUENCE: 10

Leu His Leu Gly Ser Arg Gln Lys Lys Ile Arg Ile Gln Leu Arg
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: A part of XAGE1 19-33

<400> SEQUENCE: 11

Gly Ser Arg Gln Lys Lys Ile Arg Ile Gln Leu Arg Ser Gln Cys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: A part of XAGE1 22-36

<400> SEQUENCE: 12

Gln Lys Lys Ile Arg Ile Gln Leu Arg Ser Gln Cys Ala Thr Trp
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: A part of XAGE1 25-39

<400> SEQUENCE: 13

Ile Arg Ile Gln Leu Arg Ser Gln Cys Ala Thr Trp Lys Val Ile
1               5                   10                  15

<210> SEQ ID NO 14
```

```
<211> LENGTH: 15
<212> TYPE: PRT
<213> ORGANISM: Artificial Sequence
<220> FEATURE:
<223> OTHER INFORMATION: A part of XAGE1 28-42

<400> SEQUENCE: 14

Gln Leu Arg Ser Gln Cys Ala Thr Trp Lys Val Ile Cys Lys Ser
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: A part of XAGE1 31-45

<400> SEQUENCE: 15

Ser Gln Cys Ala Thr Trp Lys Val Ile Cys Lys Ser Cys Ile Ser
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: A part of XAGE1 37-51

<400> SEQUENCE: 16

Lys Val Ile Cys Lys Ser Cys Ile Ser Gln Thr Pro Gly Ile Asn
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: A part of XAGE1 40-54

<400> SEQUENCE: 17

Cys Lys Ser Cys Ile Ser Gln Thr Pro Gly Ile Asn Leu Asp Leu
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: A part of XAGE1 43-57

<400> SEQUENCE: 18

Cys Ile Ser Gln Thr Pro Gly Ile Asn Leu Asp Leu Gly Ser Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: A part of XAGE1 46-60

<400> SEQUENCE: 19

Gln Thr Pro Gly Ile Asn Leu Asp Leu Gly Ser Gly Val Lys Val
1               5                   10                  15

<210> SEQ ID NO 20
<211> LENGTH: 15
```

```
<212> TYPE: PRT
<213> ORGANISM: Artificial Sequence
<220> FEATURE:
<223> OTHER INFORMATION: A part of XAGE1 49-63

<400> SEQUENCE: 20

Gly Ile Asn Leu Asp Leu Gly Ser Gly Val Lys Val Lys Ile Ile
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: A part of XAGE1 52-68

<400> SEQUENCE: 21

Leu Asp Leu Gly Ser Gly Val Lys Val Lys Ile Ile Pro Lys Glu Glu
1               5                   10                  15

His

<210> SEQ ID NO 22
<211> LENGTH: 17
<212> TYPE: PRT
<213> ORGANISM: Artificial Sequence
<220> FEATURE:
<223> OTHER INFORMATION: A part of XAGE1 55-71

<400> SEQUENCE: 22

Gly Ser Gly Val Lys Val Lys Ile Ile Pro Lys Glu Glu His Cys Lys
1               5                   10                  15

Met

<210> SEQ ID NO 23
<211> LENGTH: 17
<212> TYPE: PRT
<213> ORGANISM: Artificial Sequence
<220> FEATURE:
<223> OTHER INFORMATION: A part of XAGE1 58-74

<400> SEQUENCE: 23

Val Lys Val Lys Ile Ile Pro Lys Glu Glu His Cys Lys Met Pro Glu
1               5                   10                  15

Ala

<210> SEQ ID NO 24
<211> LENGTH: 17
<212> TYPE: PRT
<213> ORGANISM: Artificial Sequence
<220> FEATURE:
<223> OTHER INFORMATION: A part of XAGE1 61-77

<400> SEQUENCE: 24

Lys Ile Ile Pro Lys Glu Glu His Cys Lys Met Pro Glu Ala Gly Glu
1               5                   10                  15

Glu
```